United States Patent
Gross et al.

(10) Patent No.: US 7,803,825 B2
(45) Date of Patent: Sep. 28, 2010

(54) AMINOALKYLAZOLE DERIVATIVES AS HISTAMINE-3 ANTAGONISTS

(75) Inventors: Jonathan Laird Gross, Cranbury, NJ (US); Albert Jean Robichaud, Ringoes, NJ (US); Marla Jean Williams, Flemington, NJ (US); Alessandro Mazzacani, Reggio Emilia (IT)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/173,255

(22) Filed: Jul. 15, 2008

(65) Prior Publication Data

US 2009/0023707 A1 Jan. 22, 2009

Related U.S. Application Data

(60) Provisional application No. 60/959,741, filed on Jul. 16, 2007.

(51) Int. Cl.
A61K 31/42 (2006.01)
(52) U.S. Cl. .................. 514/374; 540/603; 544/137; 546/209; 548/235; 548/304.7; 548/362.5; 548/518
(58) Field of Classification Search .................. 514/374; 540/603; 544/137; 546/209; 548/235, 304.7, 548/362.5, 518
See application file for complete search history.

(56) References Cited

U.S. PATENT DOCUMENTS

| | | | |
|---|---|---|---|
| 3,933,829 | A | 1/1976 | Archibald et al. |
| 4,159,331 | A | 6/1979 | McCall |
| 4,166,853 | A | 9/1979 | McCall |
| 5,883,096 | A | 3/1999 | Lowe et al. |
| 6,541,499 | B1 | 4/2003 | Bastian et al. |
| 2005/0256102 | A1 | 11/2005 | Claiborne et al. |
| 2006/0014733 | A1 | 1/2006 | Howard, Jr. et al. |
| 2006/0089496 | A1 | 4/2006 | Lam et al. |
| 2006/0166960 | A1 | 7/2006 | Aslanian et al. |
| 2007/0032475 | A1 | 2/2007 | Ye et al. |

FOREIGN PATENT DOCUMENTS

| | | |
|---|---|---|
| GB | 1416872 | 12/1975 |
| WO | WO 94/22826 | 10/1994 |
| WO | WO 98/48800 | 11/1998 |
| WO | WO 01/42224 A1 | 6/2001 |
| WO | WO 01/74773 A2 | 10/2001 |
| WO | WO 03/004467 A2 | 1/2003 |
| WO | WO 03/082272 A1 | 10/2003 |
| WO | WO 2004/081011 A1 | 9/2004 |
| WO | WO 2005/115977 A1 | 12/2005 |
| WO | WO 2006/011042 A1 | 2/2006 |
| WO | WO 2006/019833 A1 | 2/2006 |
| WO | WO 2006/023462 A1 | 3/2006 |
| WO | WO 2006/040281 A1 | 4/2006 |
| WO | WO 2007/107539 A1 | 9/2007 |
| WO | WO 2007/108936 A | 9/2007 |
| WO | WO 2007/115933 A1 | 10/2007 |
| WO | WO 2008/045371 A | 4/2008 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Blandina, P. et al., "Inhibition of cortical acetylcholine release and cognitive performance by histamine H3 receptor activation in rats", Br J Pharmacol. Dec. 1996;119(8):1656-64.
Database Chemcats [Online] chemical abstract service. Ambinter Stock Screening Collection; Feb. 13, 2008.
Esbenshade et al., "Histamine H3 receptor antagonists: preclinical promise for treating obesity and cognitive disorders", Mol Interv. Apr. 2006;6(2):77-88.
Fox, G. B. et al., "Effects of histamine H(3) receptor ligands GT-2331 and ciproxifan in a repeated acquisition avoidance response in the spontaneously hypertensive rat pup", Behav Brain Res. Apr. 1, 2002;131(1-2):151-61.
Hancock et al., Perspectives on cognitive domains, H3 receptor ligands and neurological disease, Expert Opin Investig Drugs. Oct. 2004;13(10):1237-48.
Koh et al. "Conformational and structural features determining in vitro antimalarial activity in some indolo 3, 2-couinolines, anilinoquinolines and tetrahydroindolo3, 2-dbenzazepines". European Journal of Medicinal Chemistry. vol. 29, No. 2, 1994, p. 107-113.
Komater, V.A., et al., "H3 receptor blockade by thioperamide enhances cognition in rats without inducing locomotor sensitization", Psychopharmacology (Berl). Jun. 2003;167(4):363-72.

(Continued)

*Primary Examiner*—James O Wilson
*Assistant Examiner*—Douglas M Willis
(74) *Attorney, Agent, or Firm*—Gregg C. Benson; Robert T. Ronau

(57) ABSTRACT

The present invention provides a compound of formula Ia:

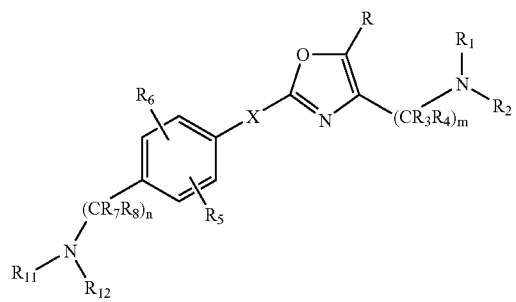

and the use thereof for the treatment of a central nervous system disorder related to or affected by the histamine-3 receptor.

26 Claims, No Drawings

OTHER PUBLICATIONS

Meguro, K. et al., "Effects of thioperamide, a histamine H3 antagonist, on the step-through passive avoidance response and histidine decarboxylase activity in senescence-accelerated mice", Pharmacol Biochem Behav. Mar. 1995;50(3):321-5.

Miyazaki, S. et al., "Effects of clobenpropit (VUF-9153), a histamine H3-receptor antagonist, on learning and memory, and on cholinergic and monoaminergic systems in mice", Life Sci. 1997;61(4):355-61.

PCT International Search Report, Written Opinion of the International Searching Authority for corresponding PCT/US2008/070048, International filing date Jul. 15, 2008.

Prast, H. et al., "Histaminergic neurons facilitate social memory in rats", Brain Res. Sep. 23, 1996;734(1-2):316-8.

* cited by examiner

AMINOALKYLAZOLE DERIVATIVES AS HISTAMINE-3 ANTAGONISTS

CROSS-REFERENCE TO RELATED APPLICATIONS

This application claims the benefit under 35 U.S.C. §119 (e) to co-pending U.S. provisional application No. 60/959,741, filed Jul. 16, 2007, which is hereby incorporated by reference in its entirety.

FIELD OF THE INVENTION

The current invention relates to aminoalkylazole compounds, their use in modulation of the histamine-3 ($H_3$) receptor and treatment of a variety of central nervous system disorders related to or affected by the $H_3$ receptor. The invention also provides methods of synthesis and pharmaceutical compositions comprising the aminoalkylazole compounds.

BACKGROUND OF THE INVENTION

The histamine-3 ($H_3$) receptor is one of four histamine receptor subtypes ($H_1$-$H_4$), all of which are members of the G-protein-coupled receptor (GPCR) superfamily. The $H_3$ receptor is predominantly expressed in the central nervous system. In the brain, it is located in regions associated with learning and memory such as the cerebral cortex, hippocampus and striatum.

The $H_3$ receptor acts as both an auto- and hetero-receptor to regulate the release of histamine and other neurotransmitters. Within the cortex, the $H_3$ receptor appears to directly modify GABA release from cortical interneurons. Antagonism of the $H_3$ receptor produces a decrease in GABA release and disinhibition of the cortical cholinergic system, resulting in increased acetylcholine levels (Bacciottini, L. et al, Behavioral Brain Research, 124, 2001, 183-194). In addition to direct regulation of cholinergic neurotransmission, the $H_3$ receptor has been shown to modulate the release of dopamine, serotonin and norepinephrine (Leurs, R., et al, Trends in Pharmacological Sciences, 19, 1998, 177-183). Thus, $H_3$ receptor blockade is able to elevate concentrations of a number of neurotransmitters, including: histamine, acetylcholine, dopamine, serotonin, norepinephrine, and glutamate, and thus offers a means for targeting cognitive processes, which often rely on the integration of multiple neurotransmitter systems.

$H_3$ agonists have been reported to impair memory in various tasks, such as object recognition, passive avoidance (Blandina, P., et al, British Journal of Pharmacology, 119(8), 1996, 1656-1664) and social olfactory memory (Prast, H., et al, 734, 1996, 316-318), whereas $H_3$ antagonists have been reported to rescue impairments produced pharmacologically or genetically. Miyazaki, S., et al, Life Sciences, 61, 1997, 355-361; Meguro, K., et al, Pharmacology, Biochemistry and Behavior, 50, 1995, 321-325; Fox, G. B., et. al, Behavioral Brain Research, 131, 2002, 151-161; and Komater, V. A., et al, Psychopharmacology, 167, 2003, 363-372.

$H_3$ receptors are targets for the control of arousal and vigilance as well as for the treatment of sleep disorders because they colocalize with histaminergic neurons in brain regions that regulate the sleep-wake cycle and they modulate histamine release and levels in the CNS. Passani et al. Trends Pharmacol. Sci. 25, 618-25, 2004. The administration of selective $H_3$ receptor agonists, such as R-α-methylhistamine, increases sleep time and slow wave sleep in cats and rodents and produces sedation in the guinea pig, whereas $H_3$ antagonists such as thioperamide increase wakefulness in cats and rats and decrease slow wave sleep and REM sleep in rats. Monti et al. Eur. J. Pharmacol. 205, 283-287, 1991 and Esbenshade et al. Molecular Interventions 6:77-88, 2006.

Studies on memory consolidation and spatial memory impairments, which are particularly prevelant in AD and dementia, have revealed that the $H_3$ antagonist thioperamide improves recall in a mouse model of premature senescence as well as in spontaneously hypertensive rat pups, and also prevents scopolamine-induced amnesia. Meguro et al. Pharmacol. Biochem. Behav. 50, 321-325, 1995 and Hancock et al. Expert Opin. Investig. Drugs 13, 1237-1248, 2004. Further, $H_3$ receptor knockout mice are insensitive to the effects of scopolamine in an inhibitory avoidance paradigm, supporting a role for $H_3$ receptor modulation of cholinergic function in memory acquisition. Toyota et al. Mol. Pharmacol. 62, 389-397, 2002.

Impairments in social recognition memory are apparent in AD, but may also be relevant to social cognitive impairment in schizophrenia and ADHD. Esbenshade et al. Molecular Interventions 6:77-88, 2006. Social recognition tests have been used to show that the administration of selective histaminergic agonists enhances social memory, whereas recall is disrupted by the inhibition of histamine synthesis. Prast et al. Brain Res. 734, 316-318, 1996. In particular, thioperamide as well as several other $H_3$ receptor antagonists have been attributed with pro-cognitive effects. Id. In working memory impairments, prevalent in AD, ADHD, and schizophrenia, thioperamide reverses scopolamine-induced deficits. Barbier et al. Br. J. Pharmacol. 143, 649-661, 2004 and Fox et al. J. Pharmacol. Exp. Ther. 305, 897-908, 2003. Thioperamide, ciproxifan, and GT-2331, all $H_3$ antagonists, are also efficacious in treating impulsivity associated with ADHD in spontaneous hypertensive rat pups. Fox et al. Behav. Brain Res. 131, 151-161, 2002.

The $H_3$ receptor is also involved in pathological processes in the 6-OHDA (6-hydroxydopamine) lesioned rat brain, a well-characterized model of Parkinson's disease. Increased $H_3$ receptor mRNA expression and binding may, for example, modulate GABAergic neuronal activity in dopamine-depleted striatum. Anichtchik et al., European Journal of Neuroscience, 12 (11), 3823-3832 2000.

Methamphetamine-induced hyperlocomotor activity, a behaviorally relevant model for psychosis, can be attenuated by ciproxifan in mice (Morisset et al. J. Pharmacol. Exp. Ther. 300, 621-628, 2002), as well as by the antipsychotic drug risperidone and the $H_3$ receptor antagonist ABT-239. Fox et al. *J. Pharmacol. Exp. Ther.* 313, 176-190 (2005). $H_3$ antagonists, such as thioperamide, have also been shown to reduce cumulative food consumption, weight gain and are suggested to have antidepressant activity. Esbenshade et al. supra and Perez-Garcia et al. Psychopharmacologia, 142(2) 215-220. 1999.

Accordingly, there is significant neuroanatomical, neurochemical, pharmacological and behavioral data to support the use of $H_3$ receptor antagonists for improving cognitive performance in disease states such as neurodegeneration, cognitive impairment, Alzheimer's disease, Parkinson's disease, dementia, psychosis, depression, attention deficit disorder (ADD)/attention deficit hyperactivity disorder (ADHD), schizophrenia, obesity and sleep disorders.

Accordingly, compounds which are inhibitors of the $H_3$ receptor find use as potential therapeutic agents in the treat-

SUMMARY OF THE INVENTION

The present invention provides an aminoalkylazole compound of formula I

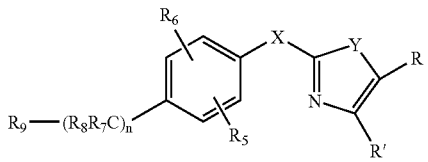

wherein
- X is $NR_{13}$ or $(CH_2)_p$;
- Y is $NR_{14}$, O or S;
- m is an integer of 1, 2 or 3;
- n is 0 or an integer of 1, 2 or 3;
- p is 0 or an integer of 1 or 2;
- R is $-(CR_3R_4)_m NR_1R_2$ and R' is H, halogen or an optionally substituted $C_1$-$C_6$ alkyl group; or
- R' is $-(CR_3R_4)_m NR_1R_2$ and R is H, halogen or an optionally substituted $C_1$-$C_6$ alkyl group;
- $R_1$ and $R_2$ are each independently H or an optionally substituted $C_1$-$C_6$ alkyl group or $R_1$ and $R_2$ may be taken together with the atom to which they are attached to form an optionally substituted 5-14 membered cycloheteroalkyl;
- $R_3$, $R_4$, $R_7$ and $R_8$ are each independently H, or an $C_1$-$C_6$ alkyl, $C_3$-$C_{10}$ cycloalkyl, or $C_6$-$C_{10}$ aryl group each optionally substituted;
- $R_5$ and $R_6$ are each independently H, halogen, $OR_{10}$ or an $C_1$-$C_6$ alkyl, $C_2$-$C_6$ alkenyl, $C_2$-$C_6$ alkynyl, $C_3$-$C_{10}$ cycloalkyl, 5-14 membered cycloheteroalkyl, $C_6$-$C_{10}$ aryl or 5-14 membered heteroaryl group each optionally substituted;
- $R_9$ is $NR_{11}R_{12}$ or $C_6$-$C_{10}$ aryl or 5-14 membered heteroaryl group each group optionally substituted, provided that if n is 0 then $R_9$ is $NR_{11}R_{12}$ or optionally substituted benzimidazolyl;
- $R_{10}$ is H or an optionally substituted $C_1$-$C_6$ alkyl group;
- $R_{11}$ and $R_{12}$ are taken together with the atom to which they are attached to form an optionally substituted fused bicyclic 9- to 11-membered ring system optionally containing one to three additional heteroatoms selected from N, O or S; and
- $R_{13}$ and $R_{14}$ are each independently H or an optionally substituted $C_1$-$C_6$ alkyl group; or a stereoisomer or a pharmaceutically acceptable salt thereof.

The present invention also provides methods and compositions useful for the therapeutic treatment of central nervous system disorders related to or affected by the Histamine-3 receptor.

Another embodiment of the present invention provides use of a composition of any one of the embodiments described herein for the treatment of a central nervous system disorder related to or affected by the $H_3$ receptor. More particularly, the present invention provides for use of a compound of any one of the embodiments described herein for the manufacture of a medicament for the treatment of a central nervous system disorder related to or affected by the $H_3$ receptor.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Alzheimer's disease (AD) is characterized by a progressive loss of memory and cognitive function and is the most common cause of dementia in the elderly. AD is believed to affect approximately 15-20 million people worldwide. The goal of treatment in AD, in addition to reversing the disease process, is to improve or at least slow the loss of memory and cognition and to maintain independent function in patients with mild to moderate disease. AD is characterized by numerous deficits in neurotransmitter function (Möller, H.-J., European Neuropsychopharmacology, 9, 1999, S53-S59), further a postmortem study in humans suggests that a decrease in brain histamine levels may contribute to the cognitive decline associated with AD, directly or through the cholinergic system (Panula, P., et al., Neuroscience, 82, 1998, 993-997). Histamine-3 ($H_3$) receptor antagonists have been reported to rescue impairments produced pharmacologically or genetically (Miyazaki, S., et al, Life Sciences, 61, 1997, 355-361; Meguro, K., et al, Pharmacology, Biochemistry and Behavior, 50, 1995, 321-325; Fox, G. B., et. al, Behavioral Brain Research, 131, 2002, 151-161; and Komater, V. A., et al, Psychopharmacology, 167, 2003, 363-372). Neuroanatomical, neurochemical, pharmacological and behavioral data support the belief that $H_3$ receptor antagonists may improve cognitive performance in disease states such as mild cognitive impairment and Alzheimer's disease and may have therapeutic value in the treatment of attention deficit disorder (ADD)/attention deficit hyperactivity disorder (ADHD), schizophrenia, particularly cognitive dysfunction in schizophrenia, dementia, psychosis, depression, Parkinson's disease, obesity, eating disorders, sleep disorders and neuropathic pain. To that end, compounds which inhibit the $H_3$ receptor and act as $H_3$ antagonists are earnestly sought.

Surprisingly it has now been found that aminoalkylazole compounds of formula I demonstrate $H_3$ affinity along with significant sub-type selectivity and function as $H_3$ antagonists. Advantageously, said formula I compounds are effective therapeutic agents for the treatment of central nervous system (CNS) disorders associated with or affected by the $H_3$ receptor. Accordingly, the present invention provides an an aminoalkylazole compound of formula I:

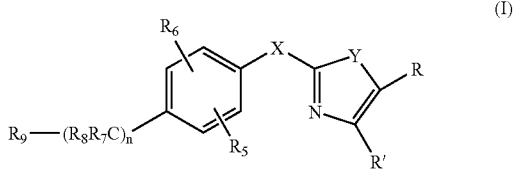

wherein
- X is $NR_{13}$ or $(CH_2)_p$;
- Y is $NR_{14}$, O or S;
- m is an integer of 1, 2 or 3;

n is 0 or an integer of 1, 2 or 3;

p is 0 or an integer of 1 or 2;

R is —$(CR_3R_4)_m NR_1R_2$ and R' is H, halogen or an optionally substituted $C_1$-$C_6$ alkyl group; or R' is —$(CR_3R_4)_m NR_1R_2$ and R is H, halogen or an optionally substituted $C_1$-$C_6$ alkyl group;

$R_1$ and $R_2$ are each independently H or an optionally substituted $C_1$-$C_6$ alkyl group or $R_1$ and $R_2$ may be taken together with the atom to which they are attached to form an optionally substituted 5-14 membered cycloheteroalkyl;

$R_3$, $R_4$, $R_7$ and $R_8$ are each independently H, or an $C_1$-$C_6$ alkyl, $C_3$-$C_{10}$ cycloalkyl, or $C_6$-$C_{10}$ aryl group each optionally substituted;

$R_5$ and $R_6$ are each independently H, halogen, $OR_{10}$ or an $C_1$-$C_6$ alkyl, $C_2$-$C_6$ alkenyl, $C_2$-$C_6$ alkynyl, $C_3$-$C_{10}$ cycloalkyl, 5-14 membered cycloheteroalkyl, $C_6$-$C_{10}$ aryl or 5-14 membered heteroaryl group each optionally substituted;

$R_9$ is $NR_{11}R_{12}$ or $C_6$-$C_{10}$ aryl or 5-14 membered heteroaryl group each group optionally substituted, provided that if n is 0 then $R_9$ is $NR_{11}R_{12}$ or optionally substituted benzimidazolyl;

$R_{10}$ is H or an optionally substituted $C_1$-$C_6$ alkyl group;

$R_{11}$ and $R_{12}$ are taken together with the atom to which they are attached to form an optionally substituted fused bicyclic 9- to 11-membered ring system optionally containing one to three additional heteroatoms selected from N, O or S; and $R_{13}$ and $R_{14}$ are each independently H or an optionally substituted $C_1$-$C_6$ alkyl group; or a stereoisomer or a pharmaceutically acceptable salt thereof.

A more particular embodiment provides a compound having the structure of formula Ia

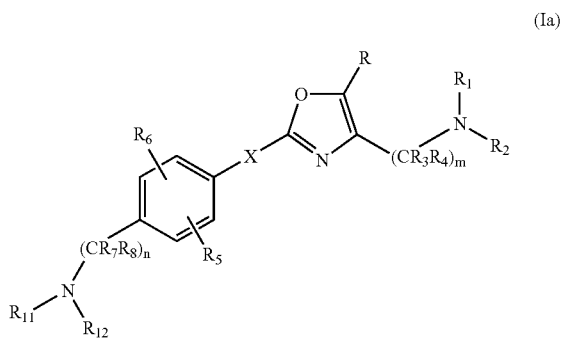

(Ia)

or a stereoisomer or pharmaceutically acceptable salt thereof.

Preferred compounds of formula Ia include those compounds wherein $R_1$ and $R_2$ are taken together with the atom to which they are attached to form a 5-membered ring and $R_{11}$ and $R_{12}$ are taken together with the atom to which they are attached to form an optionally substituted benzimidazole ring.

In another embodiment, X is $(CH_2)_p$. More particularly, p is 0.

In another embodiment, m is 1. In another embodiment, n is 1. Alternatively, n is 0.

In another embodiment, $R_3$, $R_4$, $R_7$ and $R_8$ are each independently H or optionally substituted methyl.

In another embodiment, $R_1$ and $R_2$ are taken together with the atom to which they are attached to form an optionally substituted 5-membered ring. In another embodiment, $R_1$ and $R_2$ are taken together with the atom to which they are attached to form an optionally substituted 5-membered ring; and $R_{11}$ and $R_{12}$ are taken together with the atom to which they are attached to form an optionally substituted benzimidazole ring.

In another embodiment, $R_{11}$ and $R_{12}$ are taken together with the atom to which they are attached to form an optionally substituted indole, indazole or benzimidazole ring.

In another embodiment, Y is O. Alternatively, Y is S.

In another embodiment, R is H.

In another embodiment, $NR_{11}R_{12}$ has the following structure:

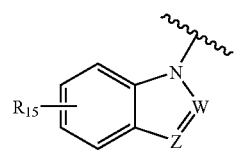

wherein,

W and Z are each independently N or $CR_{16}$; and $R_{15}$ and $R_{16}$ are each independently H, $C_1$-$C_6$ alkyl, $C_1$-$C_6$ alkoxy, $C_6$-$C_{10}$ aryl or $C_3$-$C_{10}$ cycloalkyl, each optionally substituted with halo;

with the proviso that W and Z are not both N;

or a stereoisomer or pharmaceutically acceptable salt thereof.

In a more particular embodiment, W is $CR_{16}$ and Z is N. Alternatively, W is N and Z is $CR_{16}$. Alternatively, both W and Z are independently $CR_{16}$. In another embodiment, $R_{16}$ is H and $R_{15}$ is H.

In another embodiment, $R_9$ has the following structure:

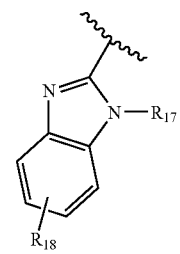

wherein, $R_{17}$ is H or $C_1$-$C_6$ alkyl or $C_3$-$C_{10}$ cycloalkyl each substituted with 0-4 substituents independently selected from the group consisting of $C_1$-$C_4$ alkyl, $C_3$-$C_6$ cycloalkyl, $C_2$-$C_6$ alkenyl, $C_2$-$C_6$ alkynyl, halo, nitro, cyano, hydroxy, phenyl, 5-14 membered heterocyclyl, —$N(R^a)_2$, —$C(O)R^b$, —$OR^c$ and —$S(O)_q R^d$;

$R_{18}$ is H, halo, nitro, cyano, hydroxy, $S(O)_q R^d$, —$N(R^a)_2$, or $C_1$-$C_6$ alkyl, $C_1$-$C_6$ acyl, $C_1$-$C_6$ alkoxy, $C_6$-$C_{10}$ aryl, 5-14 membered heteroaryl, 5-14 membered heterocyclyl, or $C_3$-$C_{10}$ cycloalkyl, each substituted with 0-4 substituents independently selected from the group consisting of $C_1$-$C_4$ alkyl, $C_3$-$C_6$ cycloalkyl, $C_2$-$C_6$ alkenyl, $C_2$-$C_6$ alkynyl, halo, nitro, cyano, hydroxy, phenyl, 5-14 membered heterocyclyl, —$N(R^a)_2$, —$C(O)R^b$, —$OR^c$ and —$S(O)_q R^d$;

each $R^a$ is independently H, $C_1$-$C_4$ alkyl optionally substituted with halo, —CHO, —$C(O)(C_1$-$C_4$ alkyl) or —$CO_2(C_1$-$C_4$ alkyl);

each $R^b$ is independently H, —OH, —O($C_1$-$C_4$), $C_1$-$C_4$ alkyl optionally substituted with halo, —$NH_2$, —NH($C_1$-$C_4$ alkyl) or —N($C_1$-$C_4$ alkyl)$_2$;

each $R^c$ is independently H, $C_1$-$C_4$ alkyl optionally substituted with halo, —CHO or —C(O)($C_1$-$C_4$ alkyl);

each $R^d$ is independently $C_1$-$C_4$ alkyl optionally substituted with halo, or —OH; and each q is independently 0, 1 or 2;

or a stereoisomer or pharmaceutically acceptable salt thereof.

In a more particular embodiment, $R_{18}$ is H. In another embodiment $R_{17}$ is H or methyl.

In another embodiment, $NR_1R_2$ has the following structure:

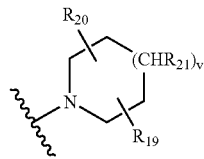

v is 0, 1 or 2;

$R_{19}$, $R_{20}$ and $R_{21}$ are each independently H, halo, nitro, cyano, hydroxy, $S(O)_qR^d$, $N(R^a)_2$, or $C_1$-$C_6$ alkyl, $C_1$-$C_6$ acyl, $C_1$-$C_6$ alkoxy, $C_6$-$C_{10}$ aryl, 5-14 membered heteroaryl, 5-14 membered heterocyclyl, or $C_3$-$C_{10}$ cycloalkyl, each substituted with 0-4 substituents independently selected from the group consisting of $C_1$-$C_4$ alkyl, $C_3$-$C_6$ cycloalkyl, $C_2$-$C_6$ alkenyl, $C_2$-$C_6$ alkynyl, halo, nitro, cyano, hydroxy, phenyl, 5-14 membered heterocyclyl, —N($R^a$)$_2$, —C(O)$R^b$, —O$R^c$ and —S(O)$_qR^d$; $R^a$ is independently H, $C_1$-$C_4$ alkyl optionally substituted with halo, —CHO, —C(O)($C_1$-$C_4$ alkyl) or —$CO_2$($C_1$-$C_4$ alkyl);

each $R^a$ is independently H, $C_1$-$C_4$ alkyl optionally substituted with halo, —CHO, —C(O)($C_1$-$C_4$ alkyl) or —$CO_2$($C_1$-$C_4$ alkyl);

each $R^b$ is independently H, —OH, —O($C_1$-$C_4$), $C_1$-$C_4$ alkyl optionally substituted with halo, —$NH_2$, —NH($C_1$-$C_4$ alkyl) or —N($C_1$-$C_4$ alkyl)$_2$;

each $R^c$ is independently H, $C_1$-$C_4$ alkyl optionally substituted with halo, —CHO or —C(O)($C_1$-$C_4$ alkyl);

each $R^d$ is independently $C_1$-$C_4$ alkyl optionally substituted with halo, or —OH; and each q is independently 0, 1 or 2;

or a stereoisomer or pharmaceutically acceptable salt thereof.

In another embodiment, v is absent. More particularly, $R_{20}$ and $R_{19}$ are H. In another embodiment, v is 1 and $R_{21}$ is H. In another embodiment, v is 2 and $R_{21}$ is H. In another embodiment, $R_{19}$ and $R_{20}$ are independently H or methyl.

In another embodiment, n is 1, Y is O, W is CH, Z is N, and $NR_1R_2$ is a pyrrolidine.

In another embodiment, —$NR_1R_2$ is selected from the group consisting of piperidinyl, dimethylamino, methylethylamino, morpholin-4-yl, 4-methylpiperazinyl, diethylamino, 2-methylpyrrolidinyl, azepanyl, 2-methylpiperidinyl, 3-methylpiperidinyl, 4-methylpiperidinyl, (S)-2-(hydroxymethyl) pyrrolidinyl, (R)-2-methylpyrrolidinyl, (S)-2-methylpyrrolidinyl, (R)-3-fluoropyrrolidinyl, (S)-3-fluoropyrrolidinyl, pyrrolidinyl, and 1,3,3-trimethyl-6-azabicyclo[3.2.1]octane.

In another embodiment, $R_{15}$ is selected from the group consisting of H, 5-$OCH_3$, 6-$OCH_3$, 5-$CH_3$ and 6-$CH_3$.

In another embodiment, $R_{16}$ is $CF_3$, phenyl, H or $CH_3$.

In another embodiment, $NR_{11}R_{12}$ is indazole, 5-fluoro-indazole, 6-fluoro-indazole or 5-aminomethyl-indazole.

In another embodiment, $R_{17}$ is H, cyclobutylmethyl or 2-cyclohexylethyl.

In another aspect of the invention, the compound is selected from the group consisting of:

1-{4-[4-(pyrrolidin-1-ylmethyl)-1,3-oxazol-2-yl]benzyl}-1H-benzimidazole;

1-{4-[4-(piperidin-1-ylmethyl)-1,3-oxazol-2-yl]benzyl}-1H-benzimidazole;

1-{2-[4-(1H-benzimidazol-1-ylmethyl)phenyl]-1,3-oxazol-4-yl}-N,N-dimethylethanamine;

N-({2-[4-(1H-benzimidazol-1-ylmethyl)phenyl]-1,3-oxazol-4-yl}methyl)-N-methylmethanamine;

1-{4-[4-(morpholin-4-ylmethyl)-1,3-oxazol-2-yl]benzyl}-1H-benzimidazole;

1-(4-{4-[(4-(methylpiperazin-1-yl)methyl]-1,3-oxazol-2-yl}benzyl)-1H-benzimidazole;

N-({2-[4-(1H-benzimidazol-1-ylmethyl)phenyl]-1,3-oxazol-4-yl}methyl)-N-ethylethanamine;

1-(4-{4-[(2-methylpyrrolidin-1-yl)methyl]-1,3-oxazol-2-yl}benzyl)-1H-benzimidazole;

1-{4-[4-(azepan-1-ylmethyl)-1,3-oxazol-2-yl]benzyl}-1H-benzimidazole;

1-(4-{4-[(2-methylpiperidin-1-yl)methyl]-1,3-oxazol-2-yl}benzyl)-1H-benzimidazole;

1-(4-{4-[(3-(methylpiperidin-1-yl)methyl]-1,3-oxazol-2-yl}benzyl)-1H-benzimidazole;

1-(4-{4-[(4-(methylpiperidin-1-yl)methyl]-1,3-oxazol-2-yl}benzyl)-1H-benzimidazole;

[(2S)-1-({2-[4-(1H-benzimidazol-1-ylmethyl)phenyl]-1,3-oxazol-4-yl}methyl)pyrrolidin-2-yl]methanol;

1-[4-(4-{[(2R)-2-methylpyrrolidin-1-yl]methyl}-1,3-oxazol-2-yl)benzyl]-1H-benzimidazole;

1-[4-(4-{[(2S)-2-methylpyrrolidin-1-yl]methyl}-1,3-oxazol-2-yl)benzyl]-1H-benzimidazole;

1-[4-(4-{[(3R)-3-fluoropyrrolidin-1-yl]methyl}-1,3-oxazol-2-yl)benzyl]-1H-benzimidazole;

1-[4-(4-{[(3S)-3-fluoropyrrolidin-1-yl]methyl}-1,3-oxazol-2-yl)benzyl]-1H-benzimidazole;

1-{4-[5-methyl-4-(pyrrolidin-1-ylmethyl)-1,3-oxazol-2-yl]benzyl}-1H-benzimidazole;

1-{4-[5-bromo-4-(pyrrolidin-1-ylmethyl)-1,3-oxazol-2-yl]benzyl}-1H-benzimidazole;

1-{4-[4-(pyrrolidin-1-ylmethyl)-1,3-oxazol-2-yl]phenyl}-1H-benzimidazole;

1-{4-[4-(piperidin-1-ylmethyl)-1,3-oxazol-2-yl]benzyl}-1H-benzimidazole;

1-{2-[4-(1H-benzimidazol-1-yl)phenyl]-1,3-oxazol-4-yl}-N,N-dimethylethanamine;

N-({2-[4-(1H-benzimidazol-1-yl)phenyl]-1,3-oxazol-4-yl}methyl)-N-methylmethanamine;

1-{4-[4-morpholin-4-ylmethyl)-1,3-oxazol-2-yl]phenyl}-1H-benzimidazole;

1-(4-{4-[(4-methylpiperidin-1-yl)methyl]-1,3-oxazol-2-yl}phenyl)-1H-benzimidazole;

N-({2-[4-(1H-benzimidazol-1-yl)phenyl]-1,3-oxazol-4-yl}methyl)-N-ethylethanamine;

1-(4-{4-[(2-methylpyrrolidin-1-yl)methyl]-1,3-oxazol-2-yl}phenyl)-1H-benzimidazole;

1-{4-[4-(azepan-1-ylmethyl)-1,3-oxazol-2-yl]phenyl}-1H-benzimidazole;

1-(4-{4-[(2-methylpiperidin-1-yl)methyl]-1,3-oxazol-2-yl}phenyl)-1H-benzimidazole;

1-(4-{4-[(3-methylpiperidin-1-yl)methyl]-1,3-oxazol-2-yl}phenyl)-1H-benzimidazole;

1-(4-{4-[(4-methylpiperazin-1-yl)methyl]-1,3-oxazol-2-yl}phenyl)-1H-benzimidazole;
[(2S)-1-({2-[4-(1H-benzimidazol-1-yl)phenyl]-1,3-oxazol-4-yl}methyl)pyrrolidin-2-yl]methanol;
1-methyl-2-{4-[4-(pyrrolidin-1-ylmethyl)-1,3-oxazol-2-yl]phenyl}-1H-benzimidazole;
1-methyl-2-{4-[4-(piperidin-1-ylmethyl)-1,3-oxazol-2-yl]phenyl}-1H-benzimidazole;
N-methyl-N-({2-[4-(1-methyl-1H-benzimidazol-2-yl)phenyl]-1,3-oxazol-4-yl}methyl)ethanamine;
N,N-dimethyl-1-{2-[4-(1-methyl-1H-benzimidazol-2-yl)phenyl]-1,3-oxazol-4-yl}methanamine;
1-(cyclobutylmethyl)-2-{4-[4-(pyrrolidin-1-ylmethyl)-1,3-oxazol-2-yl]phenyl}-1H-benzimidazole;
1-(cyclobutylmethyl)-2-[4-(4-{[(2S)-2-methylpyrrolidin-1-yl]methyl}-1,3-oxazol-2-yl)phenyl]-1H-benzimidazole;
1-(2-cyclohexylethyl)-2-{4-[4-(pyrrolidin-1-ylmethyl)-1,3-oxazol-2-yl]phenyl}-1H-benzimidazole;
1-methyl-2-{4-[4-(pyrrolidin-1-ylmethyl)-1,3-oxazol-2-yl]benzyl}-1H-benzimidazole;
1-{4-[4-(pyrrolidin-1-ylmethyl)-1,3-thiazol-2-yl]benzyl}-1H-benzimidazole;
1-(4-{4-[(2-methylpyrrolidin-1-yl)methyl]-1,3-thiazol-2-yl}benzyl)-1H-benzimidazole;
1-{4-[4-(piperidin-1-ylmethyl)-1,3-thiazol-2-yl]benzyl}-1H-benzimidazole;
1-{4-[4-(azepan-1-ylmethyl)-1,3-thiazol-2-yl]benzyl}-1H-benzimidazole;
1-{4-[4-(pyrrolidin-1-ylcarbonyl)-1,3-oxazol-2-yl]benzyl}-1H-indole;
1-{4-[4-(pyrrolidin-1-ylmethyl)-1,3-oxazol-2-yl]benzyl}-1H-indole;
6-fluoro-1-[4-(4-{[(2S)-2-methylpyrrolidin-1-yl]carbonyl}-1,3-oxazol-2-yl)benzyl]-1H-indazole;
6-fluoro-1-[4-(4-{[(2S)-2-methylpyrrolidin-1-yl]methyl}-1,3-oxazol-2-yl)benzyl]-1H-indazole;
1-{4-[4-(pyrrolidin-1-ylcarbonyl)-1,3-oxazol-2-yl]benzyl}-1H-indazole
1-{4-[4-(pyrrolidin-1-ylmethyl)-1,3-oxazol-2-yl]benzyl}-1H-indazole;
1-[4-(4-{[(2R)-2-methylpyrrolidin-1-yl]methyl}-1,3-oxazol-2-yl)benzyl]-1H-indazole;
5-fluoro-1-[4-(4-{[(2R)-2-methylpyrrolidin-1-yl]methyl}-1,3-oxazol-2-yl)benzyl]-1H-indazole;
6-fluoro-1-[4-(4-{[(2R)-2-methylpyrrolidin-1-yl]methyl}-1,3-oxazol-2-yl)benzyl]-1H-indazole;
5-fluoro-1-{4-[4-(pyrrolidin-1-ylmethyl)-1,3-oxazol-2-yl]benzyl}-1H-indazole;
6-fluoro-1-{4-[4-(pyrrolidin-1-ylmethyl)-1,3-oxazol-2-yl]benzyl}-1H-indazole;
1-[4-(4-{[(2S)-2-methylpyrrolidin-1-yl]methyl}-1,3-oxazol-2-yl)benzyl]-1H-indazole;
1-(1-{4-[4-(pyrrolidin-1-ylmethyl)-1,3-oxazol-2-yl]benzyl}-1H-indazol-5-yl)methanamine;
5-fluoro-1-[4-(4-{[(2S)-2-methylpyrrolidin-1-yl]methyl}-1,3-oxazol-2-yl)benzyl]-1H-indazole;
1-{4-[5-(pyrrolidin-1-ylmethyl)-1,3-oxazol-2-yl]benzyl}-1H-benzimidazole;
1-(4-{5-[(2-methylpyrrolidin-1-yl)methyl]-1,3-oxazol-2-yl}benzyl)-1H-benzimidazole;
1-{4-[5-(piperidin-1-ylmethyl)-1,3-oxazol-2-yl]benzyl}-1H-benzimidazole;
1-[4-(5-{[(2R)-2-methylpyrrolidin-1-yl]methyl}-1,3-oxazol-2-yl)benzyl]-1H-benzimidazole;
1-(4-{5-[(3-methylpiperidin-1-yl)methyl]-1,3-oxazol-2-yl}benzyl)-1H-benzimidazole;
1-{4-[5-(azepan-1-ylmethyl)-1,3-oxazol-2-yl]benzyl}-1H-benzimidazole;
N-({2-[4-(1H-benzimidazol-1-ylmethyl)phenyl]-1,3-oxazol-5-yl}methyl)-N-methylmethanamine;
N-({2-[4-(1H-benzimidazol-1-ylmethyl)phenyl]-1,3-oxazol-5-yl}methyl)-N-ethylethanamine;
1-[4-(5-{[(2S)-2-methylpyrrolidin-1-yl]methyl}-1,3-oxazol-2-yl)benzyl]-1H-benzimidazole;
1-(4-{5-[(1,3,3-trimethyl-6-azabicyclo[3.2.1]oct-6-yl)methyl]-1,3-oxazol-2-yl}benzyl)-1H-benzimidazole;
2-phenyl-1-{4-[4-(pyrrolidin-1-ylmethyl)-1,3-oxazol-2-yl]benzyl}-1H-benzimidazole;
1-[4-(4-{[(2R)-2-methylpyrrolidin-1-yl]methyl}-1,3-oxazol-2-yl)benzyl]-2-(trifluoromethyl)-1H-benzimidazole;
1-[4-(4-{[(2S)-2-methylpyrrolidin-1-yl]methyl}-1,3-oxazol-2-yl)benzyl]-2-(trifluoromethyl)-1H-benzimidazole;
1-[4-(4-{[(2R)-2-methylpyrrolidin-1-yl]methyl}-1,3-oxazol-2-yl)benzyl]-2-phenyl-1H-benzimidazole;
1-[4-(4-{[(2S)-2-methylpyrrolidin-1-yl]methyl}-1,3-oxazol-2-yl)benzyl]-2-phenyl-1H-benzimidazole;
1-{4-[4-(azepan-1-ylmethyl)-1,3-oxazol-2-yl]benzyl}-2-(trifluoromethyl)-1H-benzimidazole;
1-{4-[4-(azepan-1-ylmethyl)-1,3-oxazol-2-yl]benzyl}-2-phenyl-1H-benzimidazole;
1-{4-[4-(azepan-1-ylmethyl)-1,3-oxazol-2-yl]benzyl}-5-methoxy-1H-benzimidazole;
1-{4-[4-(azepan-1-ylmethyl)-1,3-oxazol-2-yl]benzyl}-6-methoxy-1H-benzimidazole;
1-{4-[4-(azepan-1-ylmethyl)-1,3-oxazol-2-yl]benzyl}-5-methyl-1H-benzimidazole;
1-{4-[4-(azepan-1-ylmethyl)-1,3-oxazol-2-yl]benzyl}-6-methyl-1H-benzimidazole;
2-phenyl-1-{4-[4-(piperidin-1-ylmethyl)-1,3-oxazol-2-yl]benzyl}-1H-benzimidazole;
1-{4-[4-(piperidin-1-ylmethyl)-1,3-oxazol-2-yl]benzyl}-2-(trifluoromethyl)-1H-benzimidazole;
1-{4-[4-(azepan-1-ylmethyl)-1,3-oxazol-2-yl]benzyl}-2,5-dimethyl-1H-benzimidazole; 1-{4-[4-(azepan-1-ylmethyl)-1,3-oxazol-2-yl]benzyl}-2,6-dimethyl-1H-benzimidazole;
2,5-dimethyl-1-[4-(4-{[(2S)-2-methylpyrrolidin-1-yl]methyl}-1,3-oxazol-2-yl)benzyl]-1H-benzimidazole;
2,6-dimethyl-1-[4-(4-{[(2S)-2-methylpyrrolidin-1-yl]methyl}-1,3-oxazol-2-yl)benzyl]-1H-benzimidazole;
2,5-dimethyl-1-{4-[4-(pyrrolidin-1-ylmethyl)-1,3-oxazol-2-yl]benzyl}-1H-benzimidazole; 2,6-dimethyl-1-{4-[4-(pyrrolidin-1-ylmethyl)-1,3-oxazol-2-yl]benzyl}-1H-benzimidazole;
5-methoxy-1-{4-[4-(pyrrolidin-1-ylmethyl)-1,3-oxazol-2-yl]benzyl}-1H-benzimidazole;
6-methoxy-1-{4-[4-(pyrrolidin-1-ylmethyl)-1,3-oxazol-2-yl]benzyl}-1H-benzimidazole;
5-methyl-1-{4-[4-(pyrrolidin-1-ylmethyl)-1,3-oxazol-2-yl]benzyl}-1H-benzimidazole;
6-methyl-1-{4-[4-(pyrrolidin-1-ylmethyl)-1,3-oxazol-2-yl]benzyl}-1H-benzimidazole;
5-methoxy-1-[4-(4-{[(2S)-2-methylpyrrolidin-1-yl]methyl}-1,3-oxazol-2-yl)benzyl]-1H-benzimidazole;
6-methoxy-1-[4-(4-{[(2S)-2-methylpyrrolidin-1-yl]methyl}-1,3-oxazol-2-yl)benzyl]-1H-benzimidazole;
5-methyl-1-[4-(4-{[(2S)-2-methylpyrrolidin-1-yl]methyl}-1,3-oxazol-2-yl)benzyl]-1H-benzimidazole;
6-methyl-1-[4-(4-{[(2S)-2-methylpyrrolidin-1-yl]methyl}-1,3-oxazol-2-yl)benzyl]-1H-benzimidazole;
5-methoxy-1-[4-(4-{[(2R)-2-methylpyrrolidin-1-yl]methyl}-1,3-oxazol-2-yl)benzyl]-1H-benzimidazole;

6-methoxy-1-[4-(4-{[(2R)-2-methylpyrrolidin-1-yl]methyl}-1,3-oxazol-2-yl)benzyl]-1H-benzimidazole;
1-[4-(1-Methyl-5-pyrrolidin-1-ylmethyl-1H-imidazol-2-yl)benzyl]-1H-benzoimidazole;
(S)-1-(4-(1-methyl-5-((2-methylpyrrolidin-1-yl)methyl)-1H-imidazol-2-yl)benzyl)-1H-benzo[d]imidazole;
1-Methyl-2-phenyl-5-pyrrolidin-1-ylmethyl-1H-imidazole;
4-(1-Methyl-5-pyrrolidin-1-ylmethyl-1H-imidazol-2-yl)benzonitrile;
2-(4-Fluoro-phenyl)-1-methyl-5-pyrrolidin-1-ylmethyl-1H-imidazole
2-Biphenyl-4-yl-1-methyl-5-pyrrolidin-1-ylmethyl-1H-imidazole;
1-[4-(1-Methyl-5-pyrrolidin-1-ylmethyl-1H-imidazol-2-yl)phenyl]-1H-benzoimidazole; or a pharmaceutically acceptable salt thereof.

In another aspect of the invention, the compound has the Formula Ih:

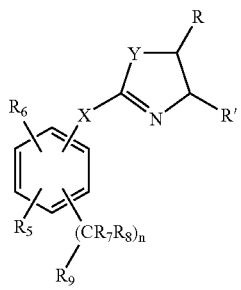

Ih wherein, the variables are as described herein.

In another embodiment, the compound has the structure:

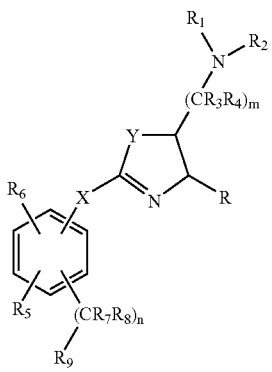

wherein
X is $NR_{13}$ or $(CH_2)_p$;
Y and Z are each independently N, O or S with the proviso that one of Y and Z must be N;
m is an integer of 1, 2 or 3;
n is 0 or an integer of 1, 2 or 3;
p is 0 or an integer of 1 or 2;
R is H, halogen or an optionally substituted alkyl group;
$R_1$ and $R_2$ are each independently H or an optionally substituted alkyl group or $R_1$ and $R_2$ may be taken together with the atom to which they are attached to form an optionally substituted 4- to 7-membered ring optionally containing one or two additional heteroatoms selected from N, O or S;
$R_3$, $R_4$, $R_7$ and $R_8$ are each independently H, or an alkyl, cycloalkyl, or aryl group each optionally substituted;
$R_5$ and $R_6$ are each independently H, halogen, $OR_{10}$ or an alkyl, alkenyl, alkynyl, cycloalkyl, cycloheteroalkyl, aryl or heteroaryl group each optionally substituted;
$R_9$ is $NR_{11}R_{12}$ or an aryl or heteroaryl group each group optionally substituted with the proviso that when n is 0 then $R_9$ must be $NR_{11}R_{12}$ or an optionally substituted benzimidazolyl group;
$R_{10}$ is H or an optionally substituted alkyl group;
$R_{11}$ and $R_{12}$ are taken together with the atom to which they are attached to form an optionally substituted fused bicyclic 9- to 11-membered ring system optionally containing one to three additional heteroatoms selected from N, O or S; and
$R_{13}$ and $R_{14}$ are each independently H or an optionally substituted alkyl group; or a stereoisomer thereof or a pharmaceutically acceptable salt thereof.

It is understood that the claims encompass all possible stereoisomers and prodrugs.

Another aspect of the invention provides a method for the treatment of a cognitive disorder related to or affected by the Histamine-3 ($H_3$) receptor in a patient in need thereof which comprises providing to said patient a therapeutically effective amount of a compound of formula I or any other embodiment thereof described herein. In a more particular embodiment, said disorder is a neurodegenerative disorder. More particular still, said disorder is mild cognitive impairment (MCI), dementia, delirium, amnestic disorder, Alzheimer's disease (AD), Parkinson's disease (PD), Huntington's disease (HD), memory disorder, memory deficits associated with depression, schizophrenia, a psychotic disorder, paranoia, manodepressive illness, attention deficit disorder (ADD), attention deficit hyperactivity disorder (ADHD), dyslexia, developmental disorders, Down's syndrome, Fragile X syndrome, loss of executive function, loss of learned information, vascular dementia, cognitive decline, neurodegenerative disorder, HIV-induced dementia, head trauma, Pick's disease, Creutzfeldt-Jakob disease, Body dementia, vascular dementia, surgical procedure-induced cognitive dysfunction, traumatic brain injury or stroke. In another more particular embodiment, said disorder is selected from the group consisting of: Alzheimer's disease, attention deficit disorder, schizophrenia; Parkinsons' disease, frontal temporal dementia or depression.

Another aspect of the invention provides a method for the inhibition of an $H_3$ receptor comprising contacting said receptor with an effective amount of a compound of formula I or any other embodiment thereof described herein.

An additional aspect of the invention provides a pharmaceutical composition which comprises a pharmaceutically acceptable carrier and an effective amount of a compound of formula I or any other embodiment thereof described herein.

"Treating" or "treatment" of a disease in a subject refers to inhibiting the disease or arresting its development; ameliorating symptoms of the disease; or causing regression of the disease.

Additionally, the compound of the invention may be used in the prevention of a disease described herein.

A "cognitive disease," "cognitive dysfunction," or "cognition-related disorder" is a disease or disorder affecting mental processes such as memory, attention, perception, action, problem solving and mental imagery. Cognitive dysfunction generally originates in the central nervous system and can be influenced or derived from neurodegeneration. Particular cognition-related disorders (e.g., cognitive dysfunction) include, without limitation, mild cognitive impairment (MCI), dementia, delirium, amnestic disorder, Alzheimer's disease, Parkinson's disease, Huntington's disease, memory disorders including memory deficits associated with depression, senile dementia, dementia of Alzheimer's disease, cognitive deficits or cognitive dysfunction associated with neurological conditions including, for example, Parkinson's disease (PD), Huntington's disease (HD), Alzheimer's disease, depression and schizophrenia (and other psychotic disorders such as paranoia and mano-depressive illness); cognitive dysfunction in schizophrenia, disorders of attention and learning such as attention deficit disorder (ADD), attention deficit hyperactivity disorder (ADHD), and dyslexia, cognitive dysfunction associated with developmental disorders such as Down's syndrome and Fragile X syndrome, loss of executive function, loss of learned information, vascular dementia, schizophrenia, cognitive decline, neurodegenerative disorder, and other dementias, for example, due to HIV disease, head trauma, Parkinson's disease, Huntington's disease, Pick's disease, Creutzfeldt-Jakob disease, or due to multiple etiologies. Cognition-related disorders also include, without limitation, cognitive dysfunction associated with MCI and dementias such as Lewy Body, vascular, and post stroke dementias. Cognitive dysfunction associated with surgical procedures, traumatic brain injury or stroke may also be treated in accordance with the embodiments described herein.

The term "$H_3$ antagonist" or "$H_3$ inhibitor" as used herein refers to a composition that reduces activity of the $H_3$ receptor. $H_3$ antagonists described herein can either reduce constitutive $H_3$ activity independent of agonist interaction (i.e. function as an inverse agonist) or reduce $H_3$ agonist-mediated activity.

An optionally substituted moiety may be substituted with one or more substituents. The substituent groups, which are optionally present, may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

Preferably, optionally substituted refers to the replacement of 0-4 hydrogen atoms with 0-4 groups selected from $C_1$-$C_6$ alkyl, $C_3$-$C_6$ cycloalkyl, $C_2$-$C_6$ alkenyl, $C_2$-$C_6$ alkynyl, halo, nitro, cyano, hydroxy, $C_6$-$C_{10}$ aryl, a 3-10 membered heterocyclyl ring, a 5-10 membered heteroaryl ring, —N($R^a$)$_2$, —C(O)$R^b$, —O$R^c$ and —S(O)$_p$$R^d$; wherein each $R^a$ is independently H, $C_1$-$C_4$ alkyl, —CHO, —C(O)($C_1$-$C_4$ alkyl), or —CO$_2$($C_1$-$C_4$ alkyl); each $R^b$ is independently H, —OH, —O($C_1$-$C_4$), $C_1$-$C_4$ alkyl, —NH$_2$, —NH($C_1$-$C_4$ alkyl), or —N($C_1$-$C_4$ alkyl)$_2$; each $R^c$ is independently H, $C_1$-$C_4$ alkyl optionally substituted with halo, —CHO or —C(O)($C_1$-$C_4$ alkyl); each $R^d$ is independently $C_1$-$C_4$ alkyl, or —OH; and p is 0, 1 or 2.

As used herein, the term alkyl includes both ($C_1$-$C_{10}$) straight chain and ($C_3$-$C_{12}$) branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of alkyl are those alkyl groups that are optionally substituted. Suitable alkyl substitutions include, but are not limited to, CN, OH, NR$_1$R$_2$, halogen, phenyl, carbamoyl, carbonyl, alkoxy or aryloxy.

As used herein, the term haloalkyl designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like.

The term halogen, as used herein, designates fluorine, chlorine, bromine, and iodine.

The term alkenyl, as used herein, refers to either a ($C_2$-$C_{10}$) straight chain or ($C_3$-$C_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term alkynyl, as used in the specification and claims, designates either a ($C_2$-$C_{10}$) straight chain or ($C_3$-$C_{10}$) branched chain monovalent hydrocarbon moiety having at least one triple bond. Such hydrocarbon alkynyl moieties may be mono or polyunsaturated, and may exist in the E or Z configurations. The compounds of this invention are meant to include all possible E and Z configurations. Examples of mono or polyunsaturated hydrocarbon alkynyl moieties include, but are not limited to, propynyl, butynyl, 1,3-butadienyl, pentynyl, hexynyl, or the like.

The term cycloalkyl, as used herein, refers to a monocyclic, bicyclic, tricyclic, fused, bridged, or spiro monovalent saturated hydrocarbon moiety of 3-10 carbon atoms. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, or the like.

The term cycloheteroalkyl, as used herein, designates one or more (fused if more than one) 5-7 membered ring systems containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR', O or S and R' is H or an optional substituent as defined hereinabove.

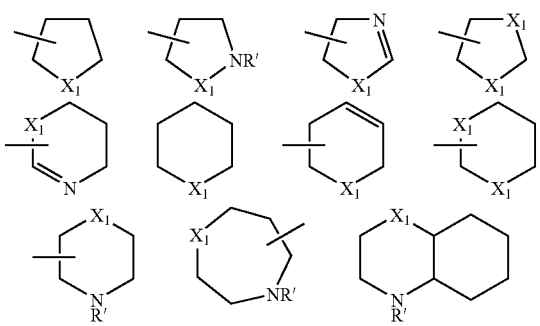

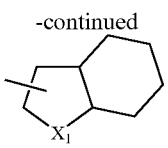

The term aryl, as used herein, refers to an aromatic carbocyclic moiety of up to 20 carbon atoms, which may be a single ring (monocyclic) or multiple rings (up to three rings) fused together. Examples of aryl moieties include, but are not limited to, chemical groups such as phenyl, 1-naphthyl, 2-naphthyl, anthryl, or the like.

The term heteroaryl as used herein designates an aromatic heterocyclic ring system, which may be a single ring (monocyclic) or multiple rings (up to three rings) fused together. The rings may contain from one to four hetero atoms selected from nitrogen, oxygen, or sulfur, wherein the nitrogen or sulfur atoms are optionally oxidized, or the nitrogen atom is optionally quarternized. Examples of heteroaryl moieties include, but are not limited to, heterocycles such as furan, thiophene, pyrrole, pyrazole, imidazole, oxazole, isoxazole, thiazole, isothiazole, oxadiazole, triazole, pyridine, pyrimidine, pyrazine, pyridazine, benzimidazole, benzoxazole, benzisoxazole, benzothiazole, benzofuran, benzothiophene, thianthrene, dibenzofuran, dibenzothiophene, indole, indazole, azaindole, azaindazole, quinoline, isoquinoline, quinazoline, quinoxaline, purine, or the like.

Exemplary of the fused bicyclic 9- to 11-membered ring system formed when $R_{11}$ and $R_{12}$ are taken together with the nitrogen atom to which they are attached are indolyl, indazolyl, benzimidazolyl, hexahydroindolizinoindolonyl, tetrahydropyranoindolyl, azaindolyl, imidazopyridinyl, indolinyl, tetrahydroquinolinyl, pyridoindolyl, dihydrodibenzoazepinyl, or the like.

As used herein: EDC designates 1-(3-dimethylaminopropyl)-3-ethylcarbo-diimide hydrochloride; HOBt designates 1-hydroxybenzotriazole; DIPEA designates diisopropylethylamine; Burgess Reagent designates (methoxycarbonylsulfamoyl)-triethylammonium hydroxide, inner salt; and DBU designates 1,8-diazabicyclo[5.4.0]-undec-7-ene.

Unless otherwise stated, structures depicted herein are also meant to include all stereochemical forms of the structure; i.e., the R and S configurations for each asymmetric center and geometric isomers around a double bond (E and Z). Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$— or $^{14}C$-enriched carbon are within the scope of this invention.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived from organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

A bond intersected with a squiggly line (e.g. ⌇) indicates the point of attachment for a substituent.

Advantageously, the present invention provides a method for the preparation of a compound of formula I which comprises reacting a compound of formula II with an amine of formula III optionally in the presence of a solvent.

More particularly, the process for the preparation of a compound of formula I involves reacting a compound of formula II:

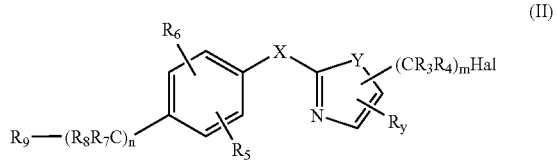
(II)

wherein, $R_y$ is H, halogen or an optionally substituted $C_1$-$C_6$ alkyl group;

Hal represents Cl, Br or I; and

X, Y, m, n, $R_3$, $R_4$, $R_5$, $R_6$, $R_7$, $R_8$ and $R_9$ are as described for formula I;

with an amine of formula III

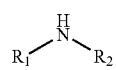
(III)

wherein $R_1$ and $R_2$ are as described for formula I optionally in the presence of a solvent. One process is shown in Scheme I wherein Hal represents Cl, Br or I.

SCHEME I

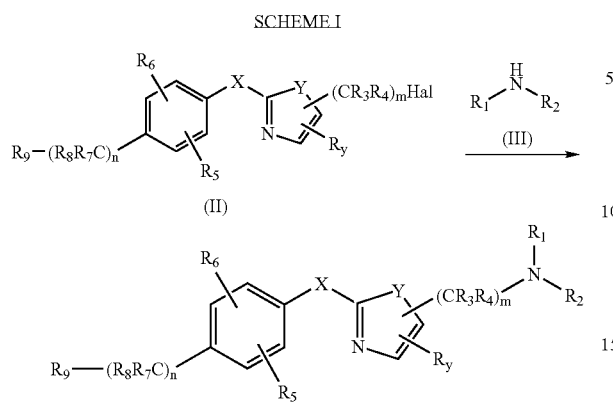

Solvents suitable for use in the method of invention include neutral organic solvents such as halogenated hydrocarbons, e.g. methylene chloride, ethylene dichloride or the like; aromatic hydrocarbons, e.g. toluene; ethers, e.g. diethyl ether, tetrahydrofuran, dioxane, or the like; esters, e.g. ethyl acetate, methyl propionate, or the like; nitriles, e.g. acetonitrile; or a mixture thereof. Any neutral non-reactive solvent capable of dissolving the reagents is suitable for use in the method of invention.

Compounds of formula II may be prepared using conventional synthetic methods and, if required, standard isolation or separation techniques. For example, compounds of formula II wherein Hal is Cl (IIa) may be prepared by reacting an ester of formula IV with a reducing agent such as lithium aluminum hydride to give the alcohol of formula V and reacting said formula V alcohol with a chlorinating agent such as thionyl chloride to give the desired compound of formula IIa. The reaction is shown in Scheme II wherein R" is $C_1$-$C_4$alkyl.

SCHEME II

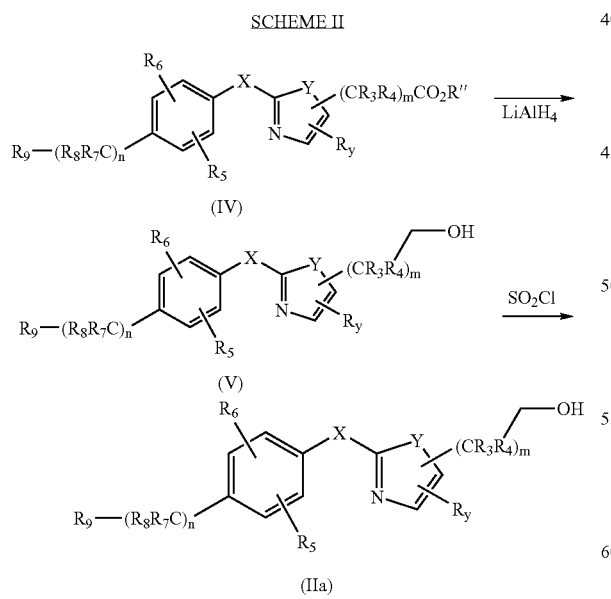

Compounds of formula II wherein Y is S; m is 1; R is H; and Hal is Cl (IIb) may be prepared by reacting a nitrile of formula XIV with $H_2S$ in the presence of a base such as triethylamine ($Et_3N$) to give the thioamide of formula XV and reacting said formula VII thioamide with 1,3-dichloroacetone to give the desired compound of formula IIb. The reaction is shown in Scheme III

SCHEME III

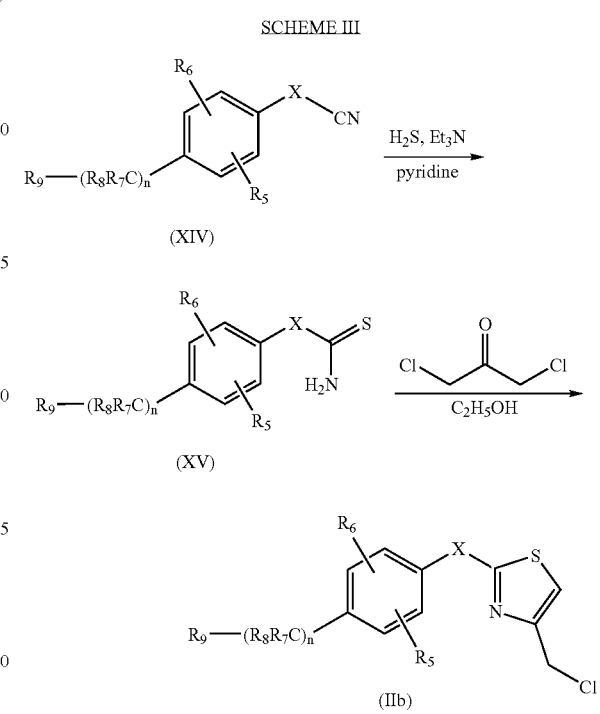

Compounds of formula IV wherein X is $(CH_2)_p$; and Y is O (IVa) may be prepared by reacting a carboxylic acid of formula VI with an amino ester of formula VII in the presence of EDC, HOBt and DIPEA to give the amide compound of formula VIII; reacting said formula VIII amide with Burgess Reagent to give the dihydro-oxazole of formula IX; and dehydrogenating the formula IX compound with $BrCCl_3$ and DBU to give the desired oxazole compound of formula IVa. The reaction is shown in Scheme IV wherein R" is $C_1$-$C_4$alkyl. Preferably, the point of attachment for the $(CH_2)_p$ and $(CR_7R_8)_n$ groups are conformationally 1,4 respective to each other.

Dihydrooxazole compounds of formula Ih are prepared by omitting the step in Scheme IVA involving treatment with $BrCCl_3$ and DBU, and instead functionalizing the compound of formula IX with —$NR_1R_2$ according to Schemes I and II.

SCHEME IVA

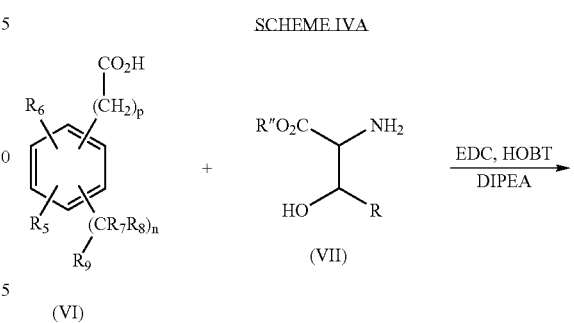

-continued

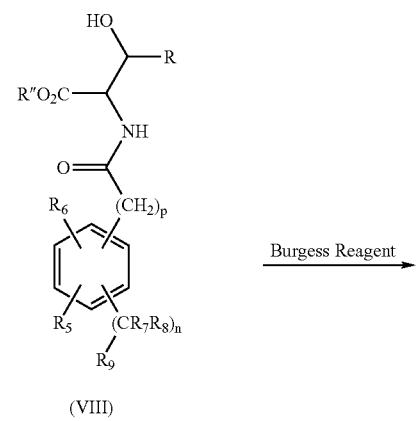
(VIII)

Burgess Reagent →

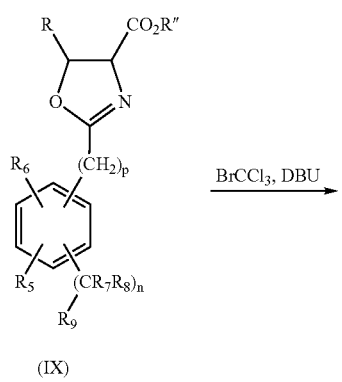
(IX)

BrCCl₃, DBU →

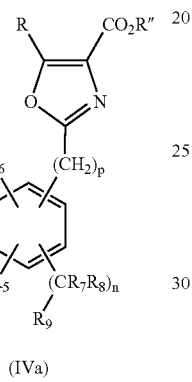
(IVa)

-continued

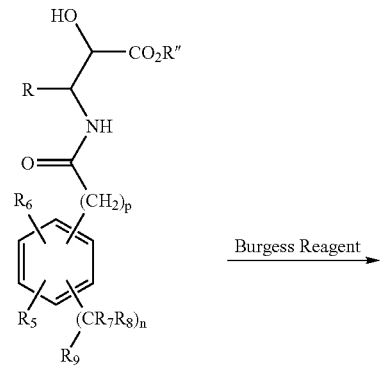
(VIIIa)

Burgess Reagent →

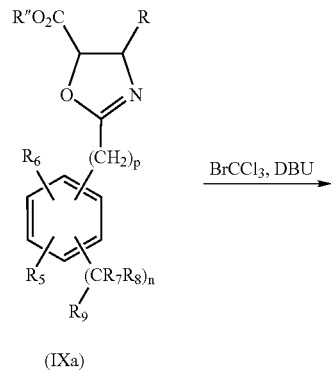
(IXa)

BrCCl₃, DBU →

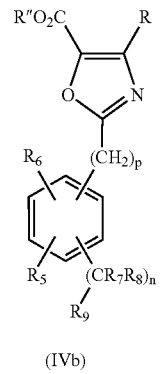
(IVb)

Compounds of formula IVb may be prepared by reacting a carboxylic acid of formula VI with an amino ester of formula VIIa in the presence of EDC, HOBt and DIPEA to give the amide compound of formula VIIIa; reacting said formula VIIIa amide with Burgess Reagent to give the dihydro-oxazole of formula IXa; and dehydrogenating the formula IXa compound with BrCCl₃ and DBU to give the desired oxazole compound of formula IVa. The reaction is shown in Scheme IVB wherein R' is $C_1$-$C_4$alkyl. Preferably, the point of attachment for the $(CH_2)_p$ and $(CR_7R_8)_n$ groups are conformationally 1,4 respective to each other.

Dihydrooxazole compounds of formula Ih are prepared by omitting the step in Scheme IVB involving treatment with BrCCl₃ and DBU, and instead functionalizing the compound of formula IXa with —NR₁R₂ according to Schemes I and II.

SCHEME IVB

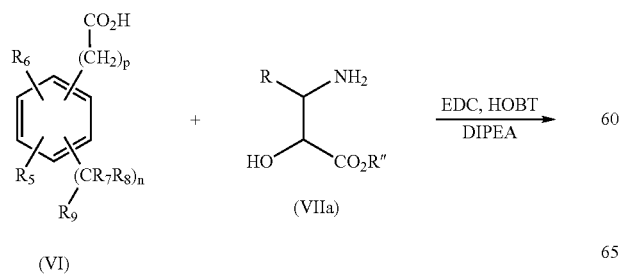

SCHEME IVC

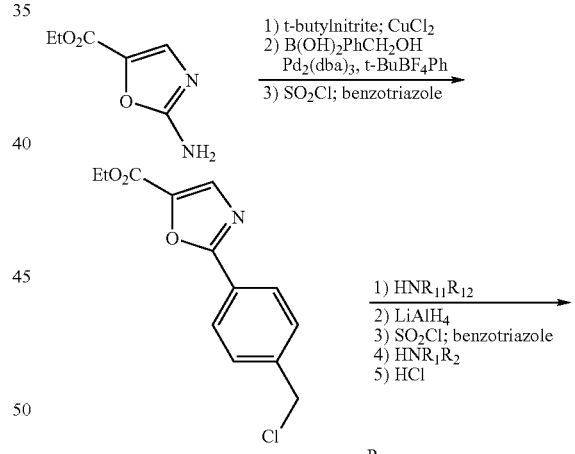

1) HNR₁₁R₁₂
2) LiAlH₄
3) SO₂Cl; benzotriazole
4) HNR₁R₂
5) HCl

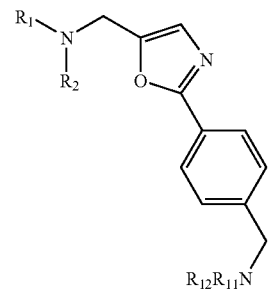

Compounds of formula I wherein X is $(CH_2)_p$; Z is N; Y is O; and $R_9$ is $NR_{11}R_{12}$ (VIa) may be conveniently prepared by reacting an ester of formula X with an amine, $HNR_{11}R_{12}$, in the presence of a base such as NaH to give the compound of formula XI and hydrolyzing said formula XI compound with a base to give the desired compound of formula VIa. The reaction is shown in Scheme V wherein R" is $C_1$-$C_4$alkyl. Preferably, the point of attachment for the $(CH_2)_p$ and $(CR_7R_8)_n$ groups are conformationally 1,4 respective to each other.

SCHEME V

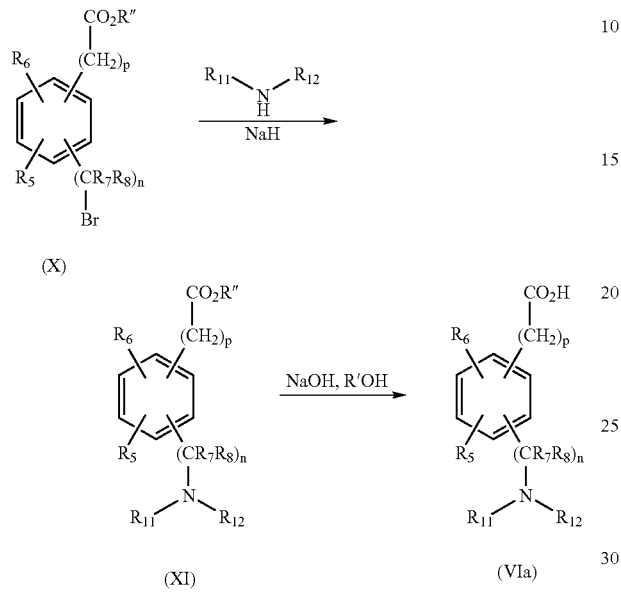

Compounds of formula VI wherein $R_9$ is an optionally substituted benzimidazol-2-yl group (VIb) may be prepared by reacting the formula X ester with sodium cyanide in a solvent such as dimethylsulfoxide (DMSO) to give the corresponding nitrile compound; hydrolyzing said nitrile with methanolic HCl to give the corresponding diester; selectively saponifying said diester to give the carboxylic acid of formula XII; coupling the formula XII acid with a phenylene diamine of formula XIII utilizing standard peptide forming conditions, for example activation of the carboxylic acid with a suitable carbodiimide such as 1-(3-dimethylaminopropyl)-3-ethylcarbodiimide in a solvent such as dichloromethane in the presence of HOBt, to afford the corresponding amide; said amide is cyclized via treatment with acetic acid at 140° C., followed by base hydrolysis to provide the desired benzimidazol-2-yl compound of formula VIb. The reaction is shown in Scheme VI wherein R" is $C_1$-$C_4$ alkyl; $R^Z$ is an optional substituent as described hereinabove; and q is 0, 1 or 2. Preferably, the point of attachment for the $(CH_2)_p$ and $(CR_7R_8)_n$ groups are conformationally 1,4 respective to each other.

SCHEME VI

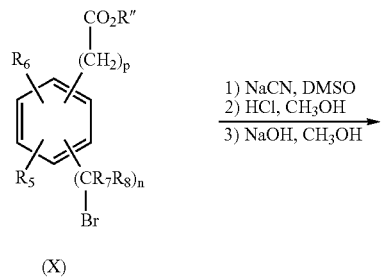

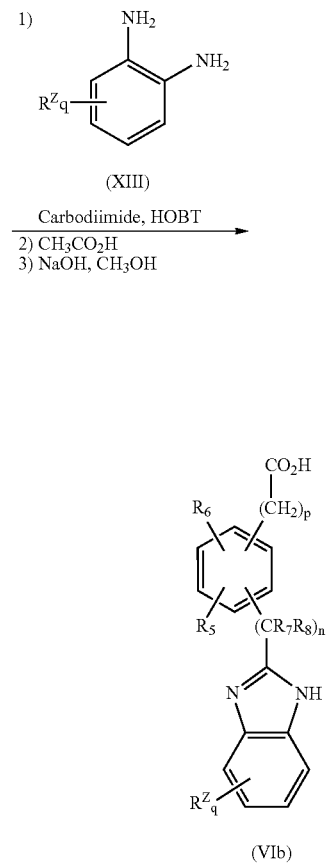

Compounds of formula VIa and VIb may then be converted into compounds of formula I wherein X is $(CH_2)_p$ by employing the reactions illustrated in Scheme IV and Scheme I.

Scheme VII describes a method for the preparation of ethyl 2-(4-((1H-benzo[d]imidazol-1-yl)methyl)phenyl)oxazole-4-carboxylate, which can be functionalized with the desired —$NR_1R_2$ group as provided in Schemes I and II.

SCHEME VII

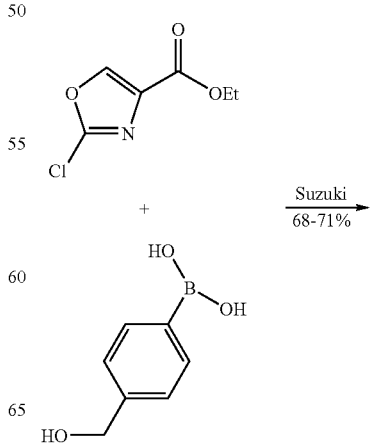

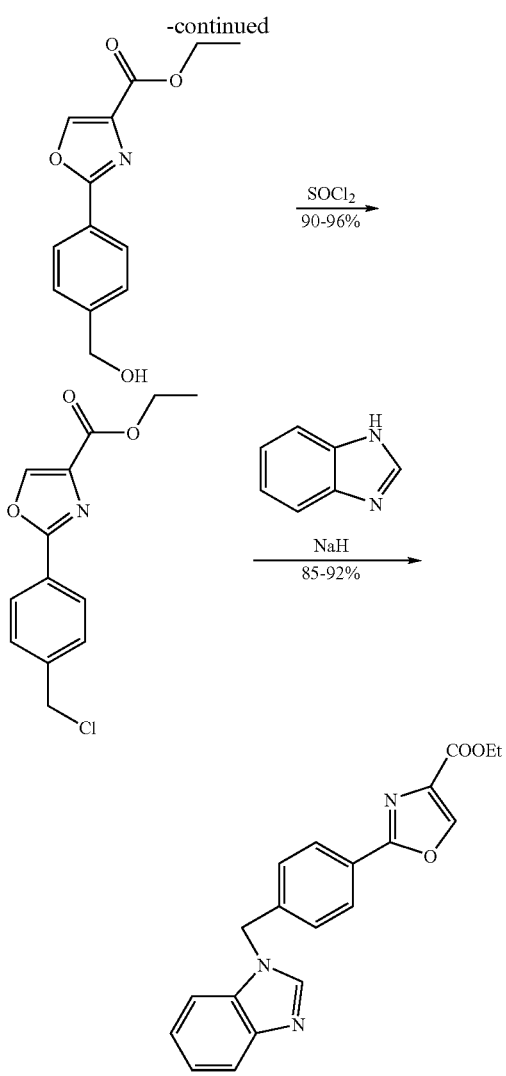

Particular formulations and dosage regimens comprising the compounds of the invention are also contemplated herein.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

In one embodiment, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures. Pharmaceutically acceptable carriers are those carriers that are compatible with the other ingredients in the formulation and are biologically acceptable.

The compounds of formula I may be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

In certain embodiments, a compound of formula I is provided in a disintegrating tablet formulation suitable for pediatric administration.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

In certain embodiments, a liquid pharmaceutical composition is provided wherein said composition is suitable for pediatric administration. In other embodiments, the liquid composition is a syrup or suspension.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I may be administered rectally or vaginally in the form of a conventional suppository. For administration by intranasal or intrabronchial inhalation or insufflation, the compounds of formula I can be formulated into an aqueous or partially aqueous solution, which can then be utilized in the form of an aerosol. The compounds of formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The therapeutically effective amount of a compound of formula I provided to a patient will vary depending upon what is being administered, the purpose of the administration, such as prophylaxis or therapy, the state of the patient, the manner of administration, or the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

For a more clear understanding, and in order to illustrate the invention more clearly, specific examples thereof are set forth hereinbelow. The following examples are merely illustrative and are not to be understood as limiting the scope and underlying principles of the invention in any way. The terms HPLC and NMR designate high performance liquid chromatography and proton nuclear magnetic resonance, respectively. The term MS designates mass spectroscopy with (+) referring to the positive mode which generally gives a M+1 (or M+H) absorption where M=the molecular mass.

Unless otherwise designated, all parts are parts by weight. The terms THF, DMF and EtOAc designate tetrahydrofuran, dimethyl formamide and ethyl acetate, respectively.

EXAMPLES

Example 1

Preparation of
4-[(1H-Benzimidazol-1-yl)methyl]benzoic acid

A solution of benzimidazole (5 mmol, 0.97 g) in THF/DMF (5:1, 20 mL) is treated with sodium hydride (0.5 g), stirred for 10 minutes at room temperature, treated with methyl 4-(bromomethyl)benzoate (1.4 g, 6 mmol) and stirred at room temperature overnight. The reaction mixture is diluted with EtOAc, washed with saturated NaHCO$_3$, dried over MgSO$_4$ and concentrated in vacuo to give methyl 4-[(1H-benzoimidazol-1-yl)methyl]benzoate as a solid residue. The residue is dissolved in MeOH/water (2:1), treated with lithium hydroxide (0.42 g, 10 mmol), stirred at room temperature overnight, evaporated to remove the MeOH. The resultant concentrate is diluted with 1N sodium hydroxide (50 mL), washed with EtOAc, acidified with concentrated HCl and extracted with EtOAc. The extracts were combined, dried over MgSO$_4$ and concentrated to dryness to give the title product in 75% yield, identified by NMR and mass spectral analyses. $^1$H NMR (400 MHz, DMSO-d$_6$): 8.08 (s, 1H); 7.99 (d, J=8 Hz, 2H); 7.78 (d, J=8 Hz, 1H); 7.24-7.27 (m, 5H); 5.49 (s, 2H). LCMS (ESI$^+$) 253 (MH+).

Example 2

Preparation of Methyl N-{4-[(1H-Benzimidazol-1-yl)methyl]benzoyl}serinate

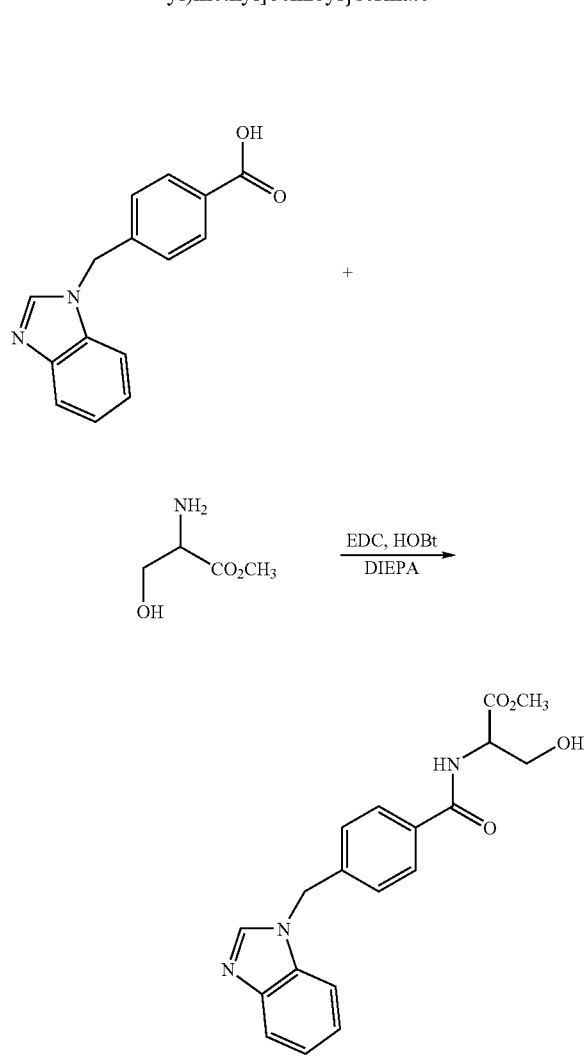

A stirred solution of 4-[(1H-benzoimidazol-1-yl)methyl]benzoic acid (4 g, 15.87 mmol) in DMF at 0° C. is treated sequentially with EDC (3.6 g, 19 mmol), HOBt (2.5 g, 19 mmol), DIPEA (5.1 g, 39.5 mmol, 2.5 eq) and serine methyl ester hydrochloride (2.9 g, 19 mol), stirred at room temperature overnight and evaporated to dryness. The resultant residue is dissolved in EtOAc and water. The layers are separated and the organic layer is washed successively with 1M HCl, water, saturated NaHCO$_3$ and brine, dried over Na$_2$SO$_4$ and concentrated under reduced pressure to give the title product in 64% yield, identified by NMR and mass spectral analyses. $^1$H NMR (400 MHz, DMSO-d$_6$): 8.23-8.26 (m, 2H); 7.9 (s, 2H); 7.87 (d, J=7.6 Hz, 2H); 7.70 (d, J=6 Hz, 1H); 7.33 (m, 3H); 7.20 (m, 2H); 5.54 (s, 2H); 4.90 (t, J=4 Hz, 1H); 4.60 (m, 1H); 3.84-3.90 (m, 2H); 3.70 (s, 3H). LCMS (ESI$^+$) 354 (MH+).

Example 3A

Preparation of Methyl {2-{4-[(1H-Benzimidazol-1-yl)methyl]phenyl}-1,3-oxazol-4-yl}carboxylate

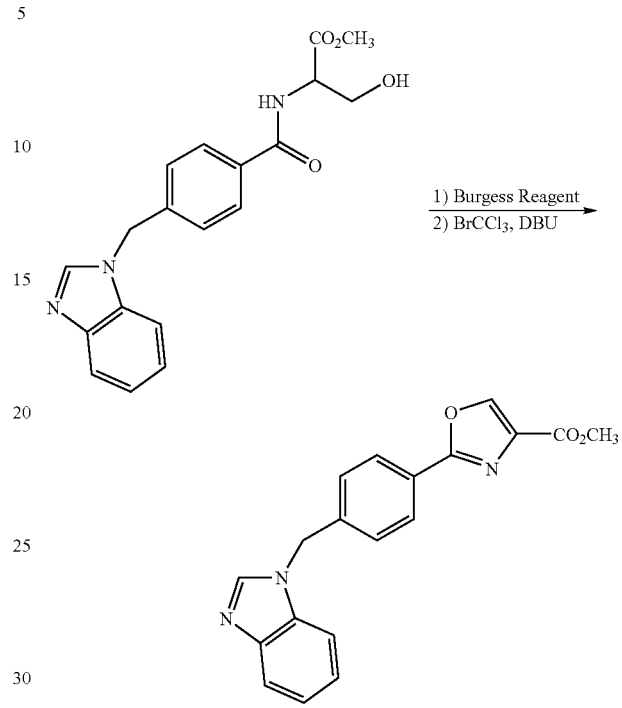

A stirred solution of methyl N-{4-[(1H-benzimidazol-1-yl)methyl]benzoyl}-serinate (2.8 g, 7.93 mmol) in THF is treated with Burgess Reagent (2.26 g, 9.45 mmol) and activated 4 Å molecular sieves (1 g), stirred at 60° C. for 2 h, cooled to room temperature and concentrated under reduced pressure. A solution of the resultant residue (0.1 g, 0.29 mmol) in CH$_2$Cl$_2$ is cooled to 0° C., treated with bromotrichloromethane (0.06 g, 0.33 mmol) and DBU (0.05 g, 0.33 mmol), stirred at room temperature overnight and concentrated under reduced pressure. The resultant residue is purified by column chromatography (silica, CH$_3$OH/CHCl$_3$ 0→5%) to give the title product in 52% yield, identified by NMR and mass spectral analyses. $^1$H NMR (400 MHz, DMSO-d$_6$): 8.28 (s, 1H); 8.08 (d, J=8 Hz, 2H); 8.00 (m, 1H); 7.85 (d, J=8 Hz, 2H); 7.30 (m, 5H); 5.43 (s, 2H); 3.95 (s, 3H). LCMS (ESI$^+$) 334 (MH$^+$).

Example 3B

Step 1

Preparation of ethyl 2-[4-(hydroxymethyl)phenyl]-1,3-oxazole-4-carboxylate

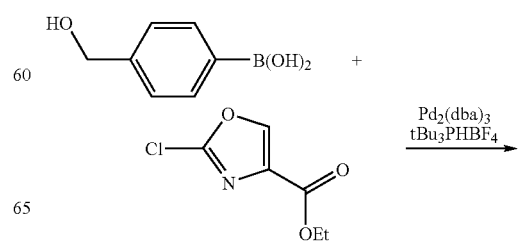

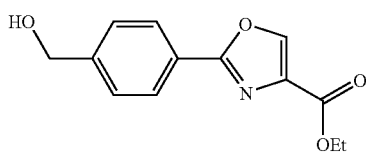

To a suspension of tris(dibenzylideneacetone)dipalladium (0) (0.025 eq) and tri-tert-butylphosphonium tetrafluoroborate (0.05 eq) a mixture of dioxane and 1N aqueous potassium carbonate (3:1) degassed with nitrogen was added chlorooxazole carboxylate (1 eq) followed by a suspension of 4-hydroxymethylphenylboronic acid (1 eq) in a mixture of dioxane and 1N aqueous potassium carbonate (8:1) continuing to degas with nitrogen and the resulting reaction mixture was stirred at 86° C. (reflux) until determined complete by HPLC (about 2 h). The reaction mixture was allowed to cool to room temperature and filtered through celite, the organic layer separated, and the aqueous layer extracted with ethyl acetate. The dioxane layer was concentrated (avoiding total evaporation to dryness) and combined with the ethyl acetate extract and washed with aq. sodium bicarbonate, brine, dried over sodium sulphate, filtered, evaporated, and triturated with MTBE. The isolated yield of the target compound was 68%. m.p. 99-101° C.; $^1$H NMR (300 MHz, CDCl3, δ): 8.27 (s, 1H), 8.10 (d, 2H, J=8.2 Hz), 7.47 (d, 2H, J=8.2 Hz), 4.77 (s, 2H), 4.43 (m, 2H, J=7.4 Hz), 1.41 (t, 3H, J=7.4 Hz).

Step 2

Preparation of ethyl 2-[4-(chloromethyl)phenyl]-1,3-oxazole-4-carboxylate

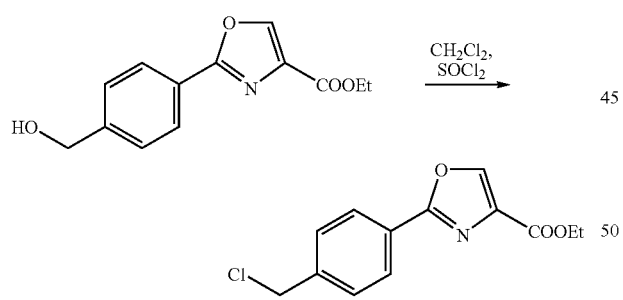

To a solution of methylene chloride at −10° C. and excess thionyl chloride was added portionwise ethyl 2-[4-(hydroxymethyl)phenyl]-1,3-oxazole-4-carboxylate (1 eq) and the resulting mixture was stirred at room temperature for 3 h. The solvent was removed and the residue was azeotroped with toluene, dissolved in methylene chloride, washed with aqueous sodium bicarbonate, dried over magnesium sulfate, filtered and evaporated to give a yield of 96% of the product as white crystals; m.p. 115-117° C. $^1$H NMR (300 MHz, CDCl3, δ): 8.28 (s, 1H), 8.12 (d, 2H, J=8.5 Hz), 7.50 (d, 2H, J=8.5 Hz), 4.62 (s, 2H), 4.43 (m, 2H, J=7.4 Hz), 1.41 (t, 3H, J=7.4 Hz).

Step 3

Preparation of ethyl 2-[4-(1H-benzimidazol-1-ylmethyl)phenyl]-1,3-oxazole-4-carboxylate

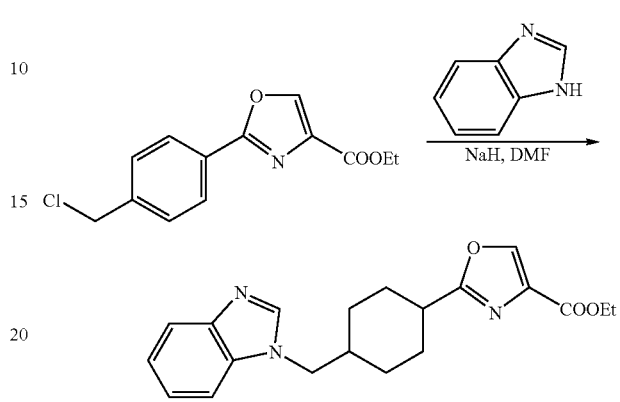

To a solution of benzimidazole (1.5 eq) in DMF was added portionwise sodium hydride (60% suspension in mineral oil, 1.5 eq) and the reaction mixture was allowed to stir for 45 min at room temperature. The reaction mixture was then added to a solution of ethyl 2-[4-(chloromethyl)phenyl]-1,3-oxazole-4-carboxylate (1 eq) in DMF and the reaction mixture was allowed to stir at room temperature for 2 h. The reaction mixture was poured into ice/water, stirred for 30 min, and the resulting precipitate filtered through a coarse filter without vacuum suction (if the filtration is bad, it is possible to decant the aqueous/DMF layer from the organic precipitate), the precipitate dissolved in methylene chloride, washed with aq. ammonium chloride, water, dried over sodium sulphate, evaporated, triturated with MTBE, filtered, dried in the oven at 40° C. overnight. The product (92.4% yield) was obtained as off-white crystals; m.p. 150-152° C. $^1$H NMR (300 MHz, DMSO-D6, δ): 8.92 (s, 1H), 8.45 (d, 2H, J=8.5 Hz), 7.99 (d, 2H, J=8.5 Hz), 7.68 (m, 1H), 7.51 (m, 1H), 7.46 (d, 2H, J=8.5 Hz), 7.21 (m, 2H), 5.61 (s, 2H), 4.31 (m, 2H, J=7.2 Hz), 3.32 (s, 2H), 130 (t, 3H, J=7.2 Hz).

Example 4

Preparation of {2-[4-[(1H-Benzimidazol-1-yl)methyl]phenyl}-1,3-oxazole-4-yl]methanol

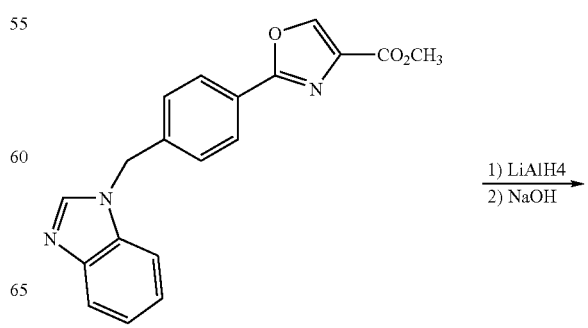

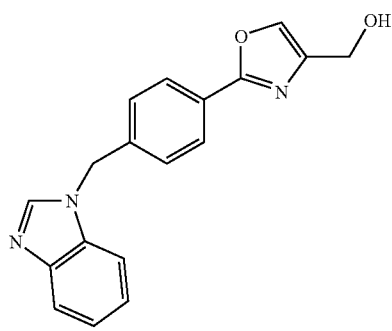

A solution of methyl {2-{4-[(1H-benzimidazol-1-yl)methyl]phenyl}-1,3-oxazol-4-yl}carboxylate (0.1 g, 3 mmol) in THF was added dropwise at −10° C. to a suspension of LiAlH₄ (0.011 g, 3 mmol) in dry THF. The reaction mixture was stirred for one hour at −10° C. and quenched with water and 10% sodium hydroxide solution. The phases were separated and the aqueous phase was extracted with ethyl acetate. The combined organic extracts were washed with brine, dried over Na₂SO₄ and evaporated to dryness to give the title product in 76% yield, identified by NMR and mass spectral analyses. ¹H NMR (400 MHz, CDCl₃): 8.00 (s, 1H), 7.98 (d, J=8 Hz, 2H), 7.78 (d, J=14 Hz, 1H), 7.67 (s, 1H), 7.55 (s, 1H), 7.2 (m, 5H), 5.4 (s, 2H), 4.59 (s, 2H). LCMS (ESI⁺) 306 (MH+).

Example 5

Preparation of 1-{4-[4-(chloromethyl)-1,3-oxazol-2-yl]benzyl}-1H-benzimidazole

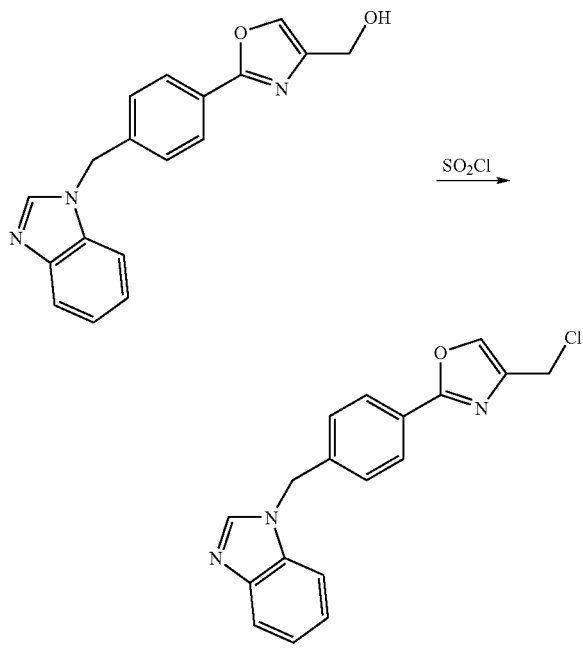

A solution of 2-{4-[(1H-benzimidazol-1-yl)methyl]phenyl}-1,3-oxazole-4-yl}methanol (0.55 g, 1.8 mmol) and DMF (0.395 g, 5.4 mmol) in CH₂Cl₂ was cooled to −10° C., treated dropwise with thionyl chloride (0.616 g, 5.4 mmol), stirred for 30 min at −10° C. and concentrated to dryness under reduced pressure to give the title product in 70% yield, identified by NMR and mass spectral analyses. ¹H NMR (400 MHz, DMSO-d₆, D₂O ex.): 8.03 (d, J=8.4 Hz, 2H), 7.98 (s, 1H), 7.91 (d, J=8 Hz, 1H), 7.88 (s, 1H), 7.77 (d, J=8 Hz, 1H), 7.54-7.60 (m, 4H), 5.9 (s, 2H), 4.6 (s, 2H). LCMS (ESI⁺) 324 (MH+).

Example 6

Preparation of 1-{4-[4-(Pyrrolidin-1-ylmethyl)-1,3-oxazol-2-yl]benzyl}-1H-benzimidazole Hydrochloride

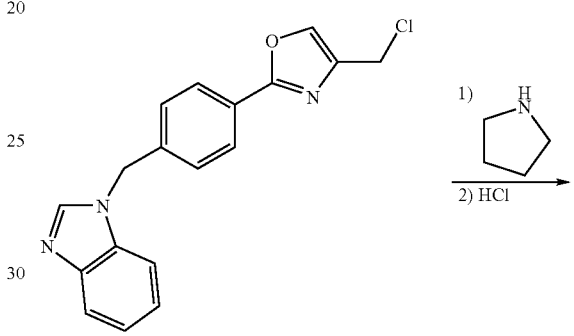

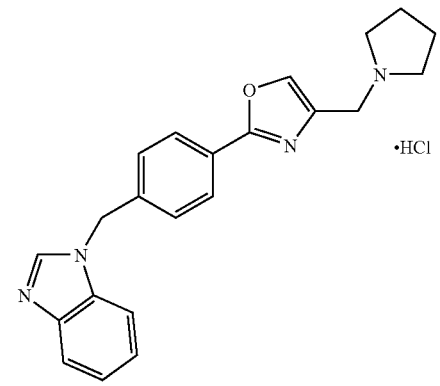

A mixture of pyrrolidine (0.032 g, 0.46 mmol) and 1-[4-(4-chloromethyl-oxazol-2-yl)-benzyl]-1H-benzoimidazole (0.05 g, 0.15 mmol) in a sealed tube at room temperature was stirred for 30 minutes. The tube was unsealed and the reaction mixture was concentrated in vacuo to remove the excess pyrrolidine. The residue was purified by column chromatography (silica, CHCl₃/CH₃OH 4%). The purified free base was treated with methanolic HCl solution, stirred for several minutes at room temperature and evaporated to dryness to afford the title product as a white solid in 51% yield, identified by NMR and mass spectral analyses. ¹H NMR (300 MHz, DMSO-d₆): 9.35 (s, 1H); 8.33 (s, 1H); 8.00 (d, 2H); 7.85 (m, 1H); 7.74 (m, 1H); 7.59 (d, 2H); 7.49 (m, 2H); 5.79 (s, 2H); 4.35 (s, 2H); 3.36 (m br, 4H); 1.98 (m, 4H)). LCMS (ESI⁺) 359 (MH+).

Examples 7-22

Preparation of 1-{4-[4-(Aminomethyl)-1,3-oxazol-2-yl]benzyl}-1H-benzimidazole Hydrochloride Compounds

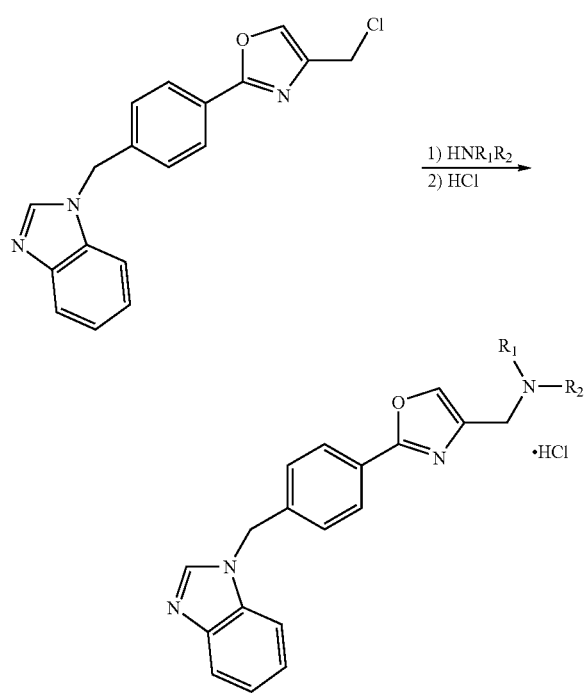

Using essentially the same procedure described in Example 6A and 6B and employing the appropriate amine, the compounds shown in Table I are obtained and identified by NMR and mass spectral analyses.

TABLE I

| Ex. No. | NR1R2 | [M + H] |
| --- | --- | --- |
| 7 | piperidinyl | 373.3 |
| 8 | dimethylamino | 333.3 |
| 9 | methylethylamino | 343.3 |
| 10 | morpholin-4-yl | 375.2 |
| 11 | 4-methylpiperazinyl | 388.3 |
| 12 | diethylamino | 361.3 |
| 13 | 2-methylpyrrolidinyl | 373.3 |
| 14 | azepanyl | 387.3 |
| 15 | 2-methylpiperidinyl | 387.3 |
| 16 | 3-methylpiperidinyl | 387.3 |

TABLE I-continued

| Ex. No. | NR1R2 | [M + H] |
| --- | --- | --- |
| 17 | 4-methylpiperidinyl | 387.3 |
| 18 | (S)-2-(hydroxymethyl)pyrrolidinyl | 389.2 |
| 19 | (R)-2-methylpyrrolidinyl | 373.26 |
| 20 | (S)-2-methylpyrrolidinyl | 373.2 |
| 21 | (R)-3-fluoropyrrolidinyl | 377.23 |
| 22 | (S)-3-fluoropyrrolidinyl | 377.2 |

Example 23

Preparation of Methyl N-[4-(1H-Benzimidazol-1-ylmethyl)benzoyl]threoninate

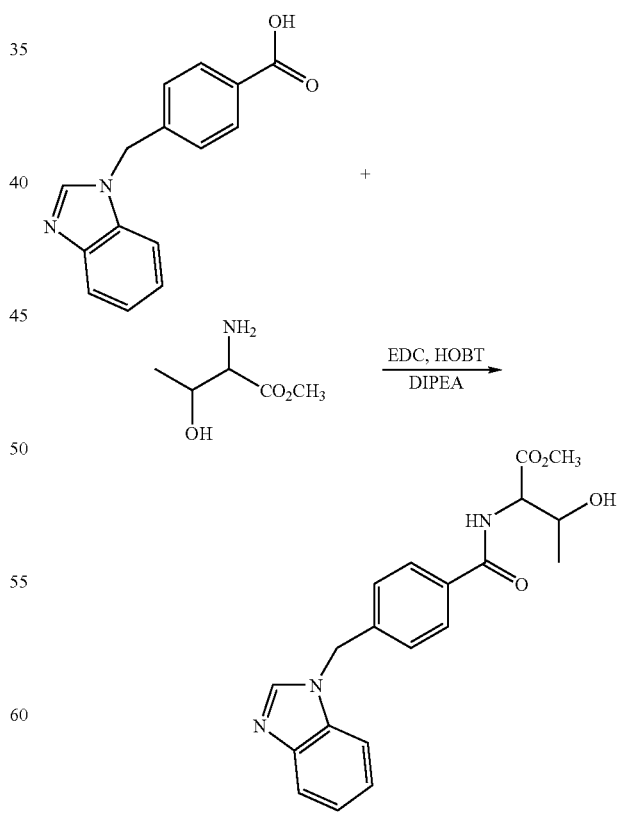

A solution of 4-[(1H-benzoimidazol-1-yl)methyl]benzoic acid (0.37 g, 1.47 mmol) in dry DMF was treated sequentially with EDC (0.34 g, 1.76 mmol) and HOBt (0.25 g, 1.62 mmol), stirred at room temperature for 30 min, treated sequentially with DIPEA (0.62 mL, 3.6 mmol) and a solution of threonine methyl ester hydrochloride (0.27 g, 1.62 mmol), stirred for 3 h and concentrated under reduced pressure. The resultant residue was partitioned between $CH_2Cl_2$ and water. The layers were separated and the organic layer was washed with brine, dried over $Na_2SO_4$ and concentrated in vacuo. The residue was purified by column chromatography (silica, $CH_2Cl_2$:$CH_3OH$ 95:5) to afford the title product in 64% yield, identified by NMR and mass spectral analyses. LCMS (ESI+) 368 (MH+).

Example 24

Preparation of Methyl {2-{4-[(1H-Benzimidazol-1-yl)methyl]phenyl}-5-methyl-1,3-oxazol-4-yl}carboxylate

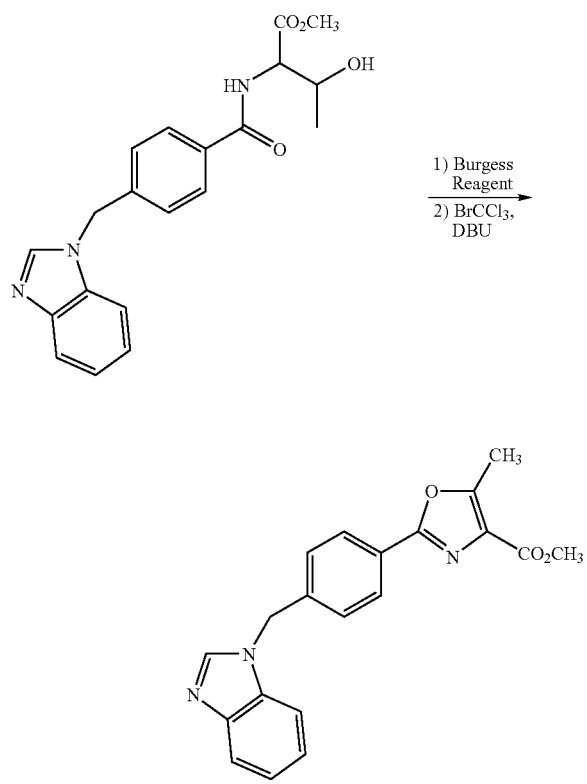

A stirred solution of methyl N-[4-(1H-benzimidazol-1-ylmethyl)benzoyl]thre-oninate (0.34 g, 0.94 mmol) in THF was treated with Burgess reagent (0.27 g, 1.12 mmol), heated to 60° C., stirred for 2 h at 60° C., cooled to room temperature and concentrated under reduced pressure. The resultant residue was purified by column chromatography (silica, $CH_2Cl_2$:$CH_3OH$ 95:5) to afford the title product in 47% yield, identified by NMR and mass spectral analyses. LCMS (ESI+) 350 (MH+).

Example 25

Preparation of {2-{4-[(1H-Benzimidazol-1-yl)methyl]phenyl}-5-methyl-1,3-oxazole-4-yl}methanol

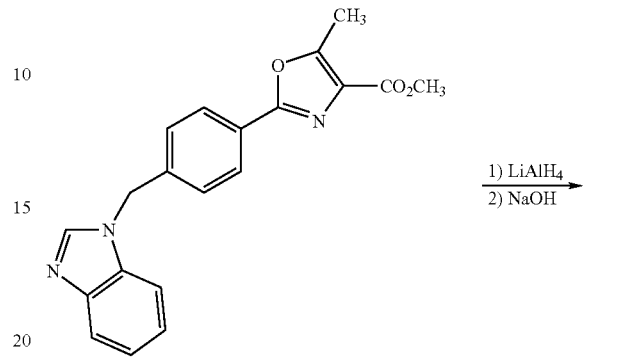

A solution of methyl {2-{4-[(1H-benzimidazol-1-yl)methyl]phenyl}-5-methyl-1,3-oxazol-4-yl}carboxylate (0.093 g, 0.27 mmol) in dry THF was treated portionwise with $LiAlH_4$ (0.020 g, 0.5 mmol) at 0° C., stirred for 1 h, quenched with ethyl acetate (0.5 mL) and water (0.2 mL), stirred for 30 min and filtered. The filtrate was concentrated under reduced pressure to give a residue. The residue was purified by column chromatography (silica, $CH_2Cl_2$:MeOH 95:5) to give the title compound as a white solid in 52% yield, identified by NMR and mass spectral analyses. LCMS (ESI+) 320 (MH+).

Example 26

Preparation of 1-{4-[4-(Chloromethyl)-5-methyl-1,3-oxazol-2-yl]benzyl}-1H-benzimidazole

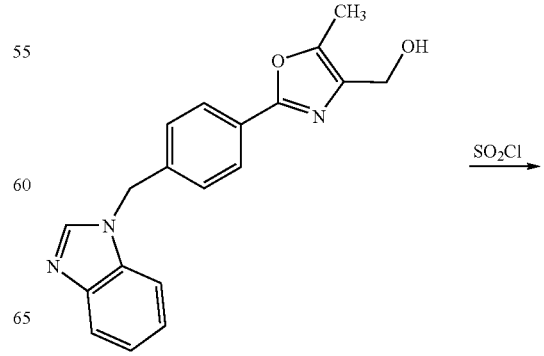

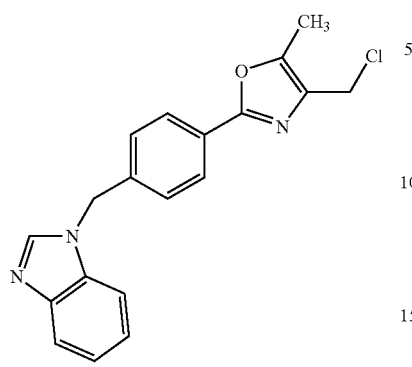

A solution of {2-{4-[(1H-benzimidazol-1-yl)methyl]phenyl}-5-methyl-1,3-oxazole-4-yl}methanol (0.045 g, 0.14 mmol) in CH$_2$Cl$_2$ was treated with a solution of thionyl chloride (0.10 mL, 1.4 mmol) in CH$_2$Cl$_2$ (2 mL), heated to reflux temperature, stirred for 30 min, cooled to room temperature and concentrated in vacuo. The resultant residue was partitioned between CH$_2$Cl$_2$ and water. The organic phase was separated, washed with water, brine, dried over Na$_2$SO$_4$, and evaporated to dryness under reduced pressure to give the title product, LCMS (ESI$^+$) 337 (MH+).

Example 27

Preparation of 1-{4-[5-Bromo-4-(chloromethyl)-1,3-oxazol-2-yl]benzyl}-1H-benzimidazole

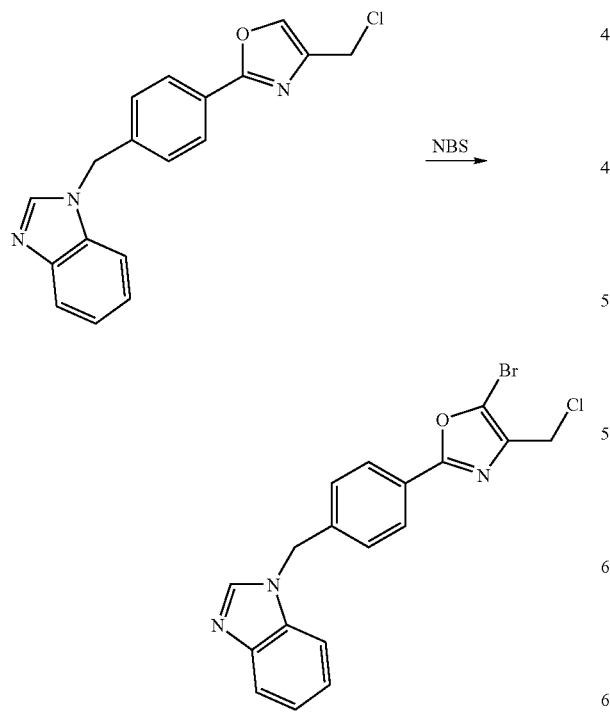

A solution of 1-{4-[4-(chloromethyl)-1,3-oxazol-2-yl]benzyl}-1H-benzimidazole (0.40 g, 1.24 mmol) in dry chloroform was treated with N-bromosuccinimide (NBS) (0.24 g, 1.36 mmol), stirred at room temperature for 1 h and concentrated in vacuo. The resultant residue was partitioned between CH$_2$Cl$_2$ and water. The organic phase was separated, washed with brine, dried over Na$_2$SO$_4$ and concentrated under reduced pressure. This residue was purified by column chromatography (silica, CH$_2$Cl$_2$:MeOH 98:2) to afford the title compound in 56% yield, identified by NMR and mass spectral analyses. $^1$H NMR (300 MHz, DMSO-d$_6$): 8.43 (s, 1H), 7.93 (m, 2H), 7.59-7.76 (m, 1H), 7.47-7.53 (m, 1H), 7.45 (m, 2H), 7.10-7.31 (m, 2H), 5.60 (s, 2H), 4.65 (s, 2H). LCMS (ESI$^+$) 402, 404 (MH+).

Examples 28 and 29

Preparation of 1-{4-[5-Substituted-4-(pyrrolidin-1-ylmethyl)-1,3-oxazol-2-yl]benzyl}-1H-benzimidazole Fumarate Compounds

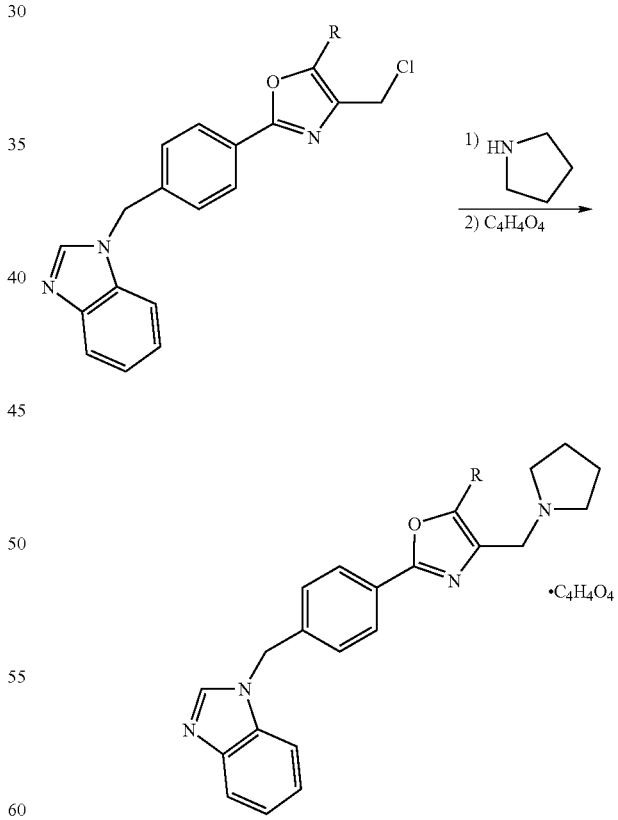

Using essentially the same procedure described in Example 6 and employing the appropriate oxazolyl substrate and pyrrolidine, the compounds shown in Table II are obtained and identified by NMR and mass spectral analyses.

TABLE II

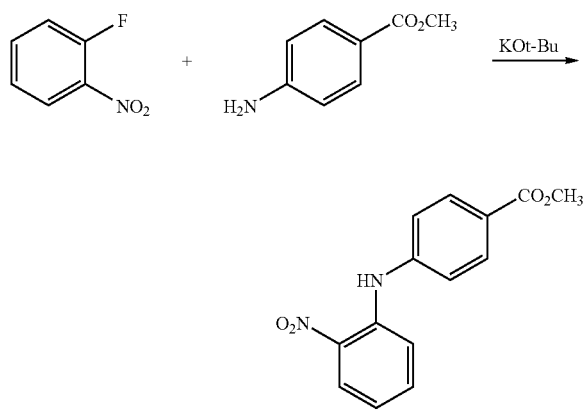

| Ex. No. | R | [M + H] |
|---------|------|---------|
| 28 | CH₃ | 373.3 |
| 29 | Br | 437.15 |

Example 30

Preparation of Methyl 4-[(2-Nitrophenyl)amino]benzoate

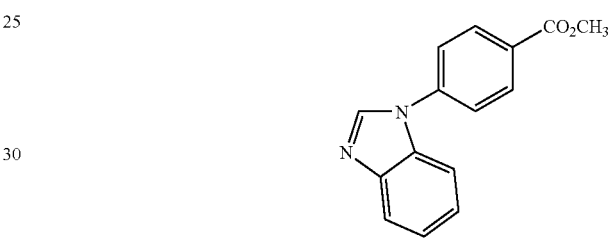

A mixture of 1-fluoro-2-nitrobenzene (0.46 g, 3.3 mmol) and methyl 4-amino-benzoate (0.5 g, 3.3 mmol) was cooled in an ice-bath, treated dropwise with a solution of potassium tert-butoxide (0.5 g, 4.9 mmol) in DMSO, stirred at room temperature overnight, quenched with water at 0° C. and extracted with ethyl acetate. The extracts were combined, washed sequentially with water and brine, dried over $Na_2SO_4$ and concentrated under vacuum to afford the title compound in 56% yield, identified by NMR and mass spectral analyses. $^1$H NMR (400 MHz, DMSO-$d_6$): 9.5 (s, 1H), 8.22 (d, J=8 Hz, 1H), 8.06 (d, J=8.4 Hz, 2H), 7.46 (d, J=4 Hz, 2H), 7.30 (d, J=8.4 Hz, 2H), 6.91 (m, 1H), 3.92 (s, 3H). LCMS (ESI⁺) 272 (MH+).

Example 31

Preparation of Methyl 4-(1H-Benzimidazol-1-yl)benzoate

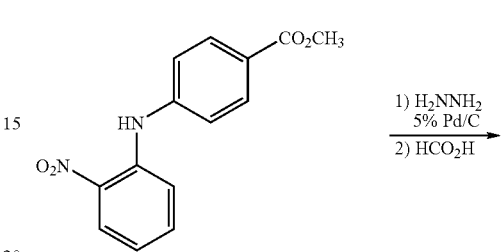

A solution of methyl 4-[(2-nitrophenyl)amino]benzoate (20 g, 48 mmol) in methanol under nitrogen was treated with 5% Pd/C (1.8 g, 30 w/v) and hydrazine hydrate (11.7 g, 230 mmol), heated at reflux temperature for 2 h, cooled to room temperature and filtered. The filtrate was concentrated under reduced pressure. The resultant residue was partitioned between $CH_2Cl_2$ and water. The organic phase was separated, dried over $Na_2SO_4$ and concentrated under vacuum. The resultant residue was purified with flash column chromatography with (silica, EtOAc:hexanes 4:6) to give 4-(2-aminophenylamino)benzoic acid methyl ester in 80% yield, $^1$H NMR (400 MHz, CDCl₃): 7.87 (d, J=8.8 Hz, 2H), 7.13 (d, J=8.0 Hz, 1H) 7.09 (t, J=8 Hz, 1H), 6.82 (d, J=8.0 Hz, 1H), 6.78 (t, J=8 Hz, 1H), 6.67 (d, J=8.0 Hz, 2H), 5.4 (bs, 1H), 3.8 (s, 3H), 3.71 (s, 2H); LCMS (ESI⁺) 243 (MH+).

A stirred solution of give 4-(2-aminophenylamino)benzoic acid methyl ester (13 g, 0.054 mol) in trimethyl orthoformate was treated with formic acid (13 mL), heated at reflux temperature for 1 h, cooled to room temperature and concentrated in vacuo. The residual oil was purified by column chromatography (silica, CHCl₃/MeOH 1%) to give the title compound in 90% yield, $^1$H NMR (400 MHz, CDCl₃): 8.26-8.28 (m, 3H), 8.17 (s, 1H), 7.90 (bs, 1H), 7.63 (d, J=8.8 Hz, 2H), 7.59 (m, 1H), 7.40 (m, 1H), 7.26 (s, 1H). 3.9 (s, 3H). LCMS (ESI⁺) 253 (MH+).

Example 32

Preparation of Methyl N-[4-(1H-Benzimidazol-1-yl)benzoyl]serinate

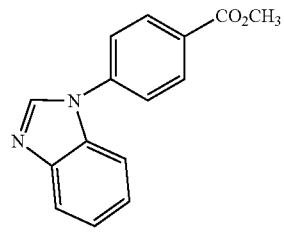 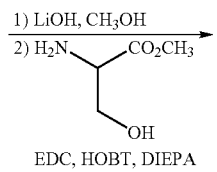

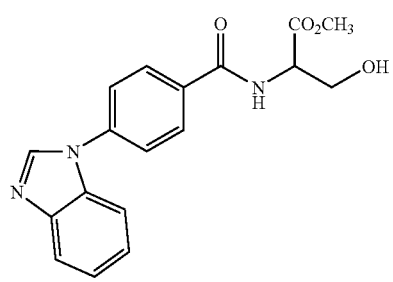

Using essentially the same procedures described in Example 1, step 2, and Example 2, and employing methyl 4-(1H-benzimidazol-1-yl)benzoate and serine methyl ester HCl as reactants, the title compound was obtained and identified by NMR and mass spectral analyses. $^1$H NMR (400 MHz, DMSO-$d_6$): 8.12 (s, 1H), 8.05 (d, J=7.2 Hz, 2H), 7.88-7.90 (m, 1H), 7.69-7.71 (m, 1H), 7.60 (d, J=7.2 Hz, 2H), 7.51-7.57 (m, 2H) 7.36-7.38 (m, 2H), 7.22-7.24 (m, 1H), 4.92-4.94 (m, 1H), 4.10-4.23 (m, 4H), 3.86 (s, 3H), 3.6 (s, 3H). LCMS (ESI$^+$) 340 (MH+).

Example 33

Preparation of Methyl {2-[4-(1H-benzimidazol-1-yl)phenyl]-1,3-oxazol-4-yl}carboxylate

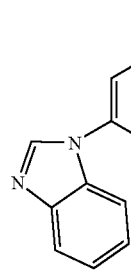 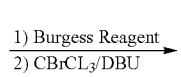

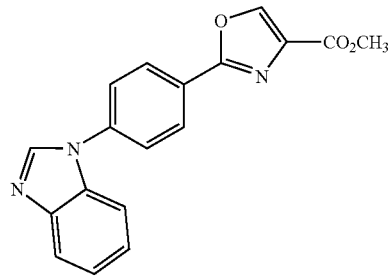

Using essentially the same procedure described in Example 24 and employing methyl N-[4-(1H-benzimidazol-1-yl)benzoyl]serinate as starting material, the title compound was obtained and identified by NMR and mass spectral analyses. $^1$H NMR (400 MHz, DMSO-$d_6$): 8.33-8.35 (m, 3H), 8.18 (s, 1H), 7.90 (bs, 1H), 7.67 (d, J=8.4 Hz, 2H), 7.60 (s, 1H), 7.37-7.39 (m, 2H), 3.99 (s, 3H). LCMS (ESI$^+$) 320 (MH+).

Example 34

Preparation of {2-[4-(1H-Benzimidazol-1-yl)phenyl]-1,3-oxazol-4-yl}methanol

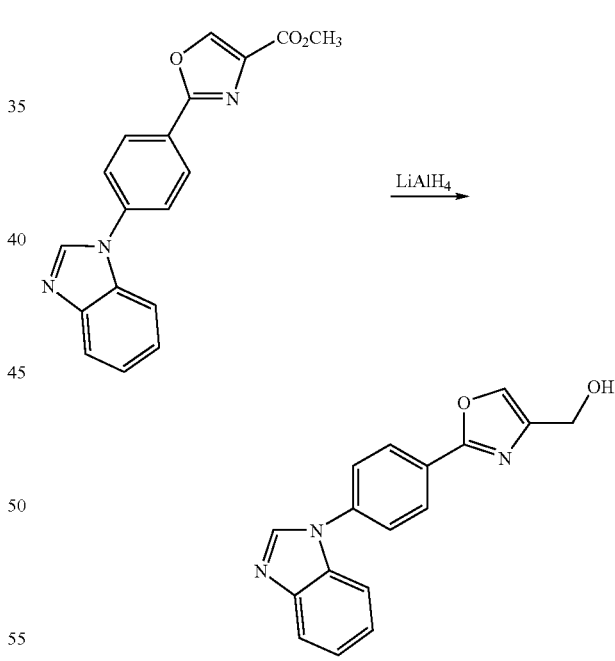

Using essentially the same procedure described in Example 25 and employing methyl {2-[4-(1H-benzimidazol-1-yl)phenyl]-1,3-oxazol-4-yl}carboxylate, the title compound was obtained and identified by NMR and mass spectral analyses. $^1$H NMR (400 MHz, DMSO-$d_6$): 8.25 (d, J=8 Hz, 2H), 8.17 (s, 1H), 7.90 (m, 1H), 7.71 (s, 1H), 7.62 (d, J=8 Hz, 2H), 7.58 (m, 1H), 7.36-7.39 (m, 1H), 4.73 (s, 2H), 2.08 (bs, 1H). LCMS (ESI$^+$) 292 (MH+).

Example 35

Preparation of 1-{4-[4-(Chloromethyl)-1,3-oxazol-2-yl]phenyl}-1H-benzimidazole

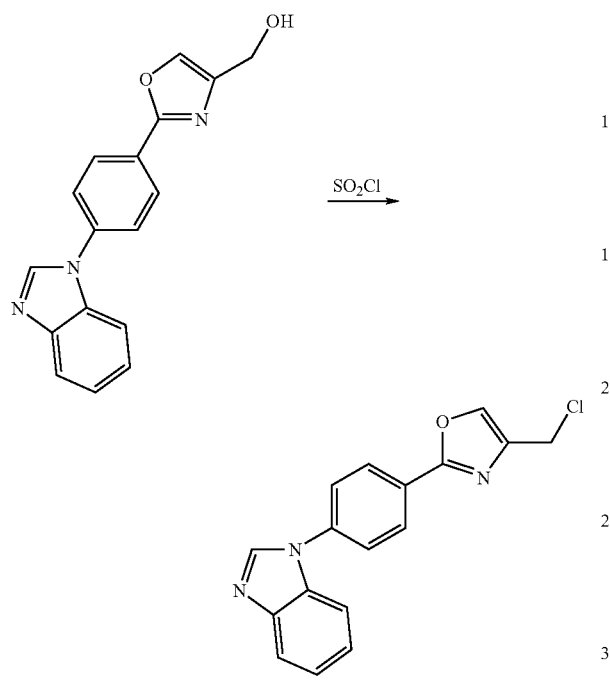

A solution of {2-[4-(1H-benzimidazol-1-yl)phenyl]-1,3-oxazol-4-yl}methanol (0.35 g, 1.2 mmol) in CH$_2$Cl$_2$ was cooled to 0° C., treated with a solution of thionyl chloride (0.37 g, 3.0 mmol) in CH$_2$Cl$_2$, stirred at 0° C. for 3 h and concentrated in vacuo. The resultant residue was partitioned between CH$_2$Cl$_2$ and water. The organic phase was separated, washed sequentially with water and brine, dried over Na$_2$SO$_4$ and evaporated to dryness under reduced pressure to afford the title product, $^1$HNMR (CDCl$_3$, 400 MHz): 8.25 (d, J=8.4 Hz, 2H), 8.17 (s, 2H), 7.67 (d, J=8.0 Hz, 1H), 7.60 (d, J=5.6 Hz, 1H), 7.36-7.38 (m, 3H), 7.26 (s, 1H), 4.61 (s, 2H). LCMS (ESI$^+$) 310 (MH+).

Examples 36-48

Preparation of 1-{4-[4-Aminomethyl-1,3-oxazol-2-yl]phenyl}-1H-benzimidazole Fumarate Compounds

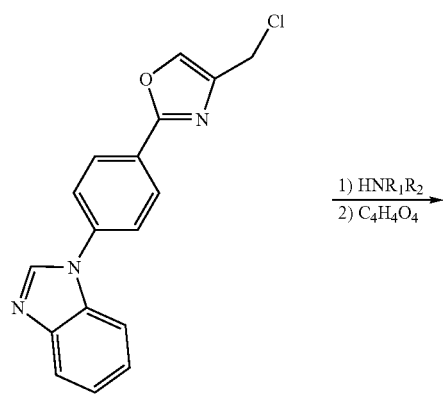

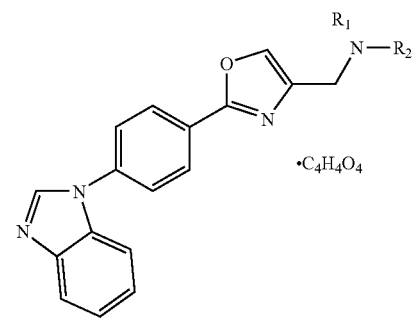

Using essentially the same procedure described in Example 6 and employing 1-{4-[4-(chloromethyl)-1,3-oxazol-2-yl]phenyl}-1H-benzimidazole and the desired amine, the compounds shown on Table III were obtained and identified by NMR and mass spectral analyses.

TABLE III

| Ex. No. | NR1R2 | [M + H] |
|---|---|---|
| 36 | pyrrolidinyl | 345.2 |
| 37 | piperidinyl | 359.2 |
| 38 | dimethylamino | 319.2 |
| 39 | methylethylamino | 333.2 |
| 40 | morpholin-4-yl | 361.2 |
| 41 | 4-methylpiperazinyl | 374.2 |
| 42 | diethylamino | 347.3 |
| 43 | 2-methylpyrrolidinyl | 359.2 |
| 44 | azepanyl | 373.1 |
| 45 | 2-methylpiperidinyl | 373.07 |
| 46 | 3-methylpiperidinyl | 373.13 |
| 47 | 4-methylpiperidinyl | 373.13 |
| 48 | (S)-2-(hydroxymethyl)pyrrolidinyl | 375.15 |

Example 49

Preparation of Methyl 4-(1-Methyl-1H-benzimidazol-2-yl)benzoate

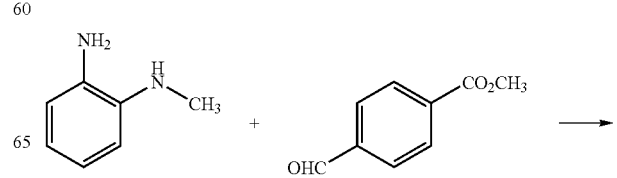

-continued

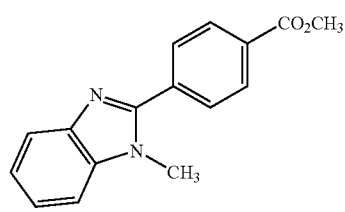

A mixture of methyl 4-formylbenzoate (5.0 g, 0.03 mol) and N-methyl-1,2-phenylene diamine (3.7 g, 0.03 mol) in nitrobenzene was heated at 140-150° C. overnight, cooled to room temperature, filtered and the filtercake washed with hexane. The combined filtrates were evaporated to dryness under reduced pressure. The resultant residue was purified by flash chromatography (silica, $CHCl_3$:MeOH 95:5) to afford the title compound in 65% yield, identified by NMR and mass spectral analyses. $^1$H NMR (400 MHz, $CDCl_3$): 8.2 (d, J=8 Hz, 2H), 7.88 (d, J=8 Hz, 2H), 7.83 (s, 1H), 7.37 (m, 1H), 7.35 (m, 2H), 3.96 (s, 3H), 3.9 (s, 3H). LCMS (ESI$^+$) 267 (MH+).

Example 50

Preparation of 2-{4-[4-(Chloromethyl)-1,3-oxazol-2-yl]phenyl}-1-methyl-1H-benzimidazole

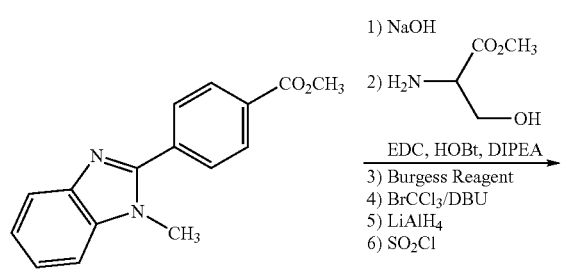

Using essentially the same procedures described in Examples 23-26 and employing methyl 4-(1-Methyl-1H-benzimidazol-2-yl)benzoate as starting material, the title compound was obtained and identified by NMR and mass spectral analyses.

$^1$H NMR (400 MHz, $CDCl_3$): 8.42 (d, J=8 Hz, 2H), 8.11 (d, J=7.6 Hz, 2H), 7.99 (d, J=7.6 Hz, 1H), 7.91 (d, J=8 Hz, 1H), 7.76-7.28 (m, 2H), 4.68 (s, 2H), 4.19 (s, 3H). LCMS (ESI$^+$) 324 (MH+).

Examples 51-54

Preparation of 1-Methyl-2-{4-[4-(aminomethyl)-1,3-oxazol-2-yl]phenyl}-1H-benzimidazole Fumarate Compounds

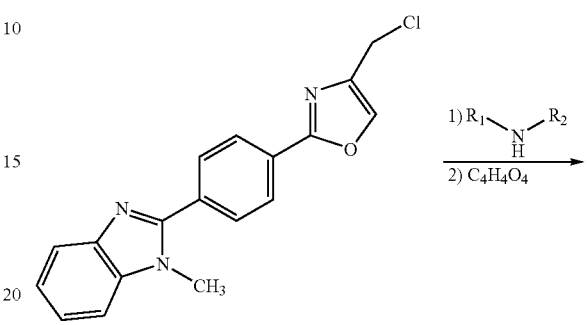

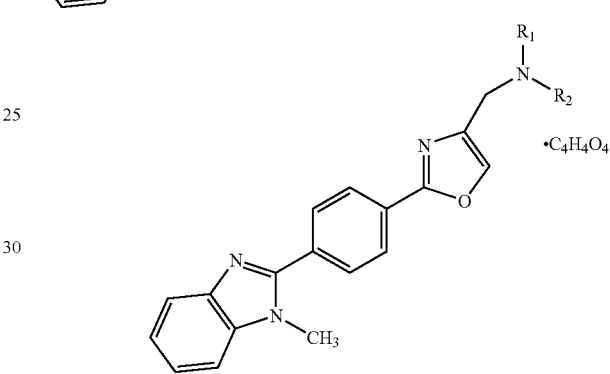

Using essentially the same procedure described in Example 6 and employing 2-{4-[4-(chloromethyl)-1,3-oxazol-2-yl]phenyl}-1-methyl-1H-benzimidazole and the desired amine, the compounds shown on Table IV were obtained and identified by NMR and mass spectral analyses.

TABLE IV

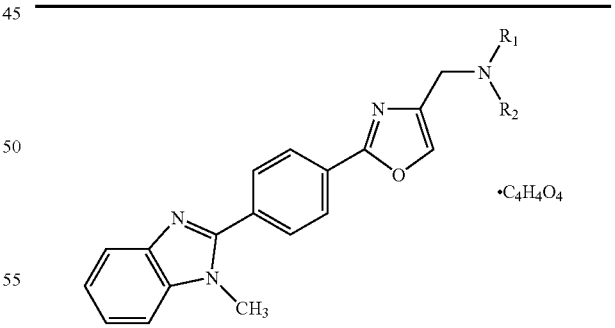

| Ex. No. | NR1R2 | [M + H] |
|---|---|---|
| 51 | pyrrolidinyl | 359.2 |
| 52 | piperidinyl | 373.3 |
| 53 | methylethylamino | 347 |
| 54 | dimethylamino | 333.2 |

Example 55

Preparation of Methyl {2-[4-(1H-benzimidazol-2-yl)phenyl]-1,3-oxazol-4-yl}carboxylate

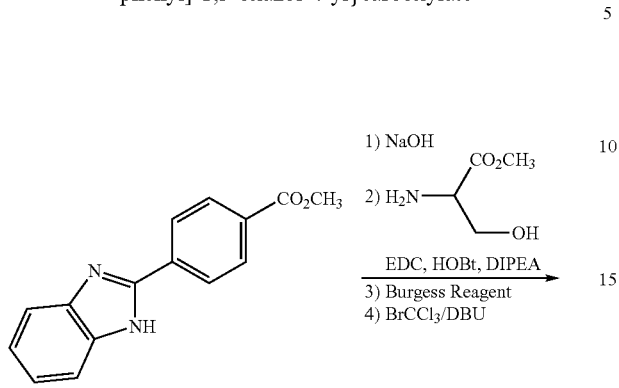

Using essentially the same procedures described in Examples 23 and 24 and employing methyl 4-(1-H-benzimidazol-2-yl)benzoate and serine methyl ester as starting materials the title compound was obtained and identified by NMR and mass spectral analyses. $^{1}$HNMR (400 MHz, DMSO-$d_6$): 3.86 (s, 3H), 7.22-7.24 (m, 2H), 7.62 (d, J=3.2 Hz, 2H), 8.19 (d, J=7.6 Hz, 2H), 8.36 (d, J=8 Hz, 2H), 9.02 (s, 1H), 13.1 (s, 1H). LCMS (ESI$^+$) 319 (MH+).

Example 56

Preparation of Methyl {2-{4-[1-(Cyclobutylmethyl)-1H-benzimidazol-2-yl]phenyl}-1,3-oxazol-4-yl}carboxylate

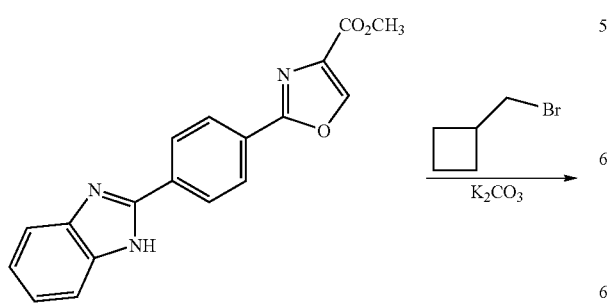

A mixture of methyl {2-[4-(1H-benzimidazol-2-yl)phenyl]-1,3-oxazol-4-yl}carboxylate (200 mg, 0.62 mmol), bromomethylcyclobutane (140 mg, 0.94 mmol) and $K_2CO_3$ (103 mg, 0.75 mmol) in dry acetonitrile was heated to 120° C. with microwave irradiation for 1.5 h. The reaction mixture was cooled to room temperature and concentrated in vacuo. The resultant residue was dissolved in $CH_2Cl_2$, washed with water, dried over $Na_2SO_4$ and evaporated to dryness under reduced pressure. This residue was purified by column chromatography (silica, $CH_2Cl_2$:MeOH 98:2) to afford the title compound in 54% yield, identified by NMR and mass spectral analyses. LCMS (ESI$^+$) 388 (MH+).

Example 57

Preparation of Methyl {2-{4-[1-(2-Cyclohexylethyl)-1H-benzimidazol-2-yl]phenyl}-1,3-oxazol-4-yl}carboxylate

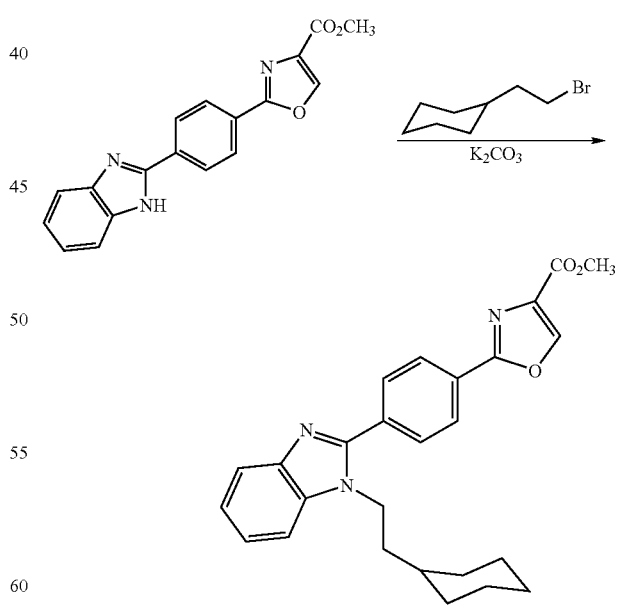

Using essentially the same procedure described in Example 56 and employing 2-bromomethylcyclohexane in place of bromomethylcyclobutane, the title compound was obtained and identified by NMR and mass spectral analyses. LCMS (ESI$^+$) 402 (MH+).

Examples 58-61

Preparation of 1-1-[(Cycloalkyl)alkyl]-2-{4-[4-(aminomethyl)-1,3-oxazol-2-yl]phenyl}-1H-benzimidazole Fumarate Compounds

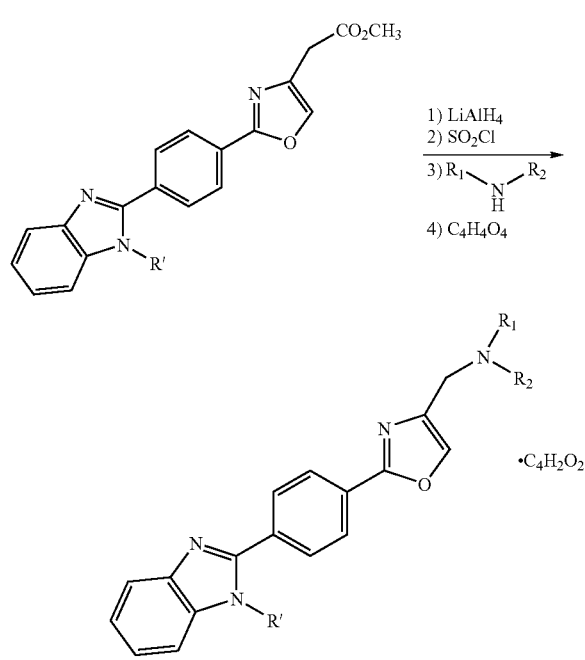

Using essentially the same procedures described in Examples 25, 35, and 6 and employing the appropriate 2-{4-{[(1-substituted)benzimidazol-2-yl]phenyl}oxazol-4-yl}carboxylate and the desired amine, the compounds shown on Table V were obtained and identified by NMR and mass spectral analyses.

TABLE V

| Ex. No. | $R_w$ | NR1R2 | [M + H] |
|---|---|---|---|
| 58 | cyclobutylmethyl | pyrrolidinyl | 413.11 |
| 59 | cyclobutylmethyl | (S)-2-methylpyrrolidinyl | 427.14 |
| 60 | 2-cyclohexylethyl | pyrrolidinyl | 455.3 |
| 61 | 2-cyclohexylethyl | (S)-2-methylpyrrolidinyl | 469.13 |

Example 62

Preparation of Methyl 4-((1H-Benzo[d]imidazol-2-yl)methyl)benzoate

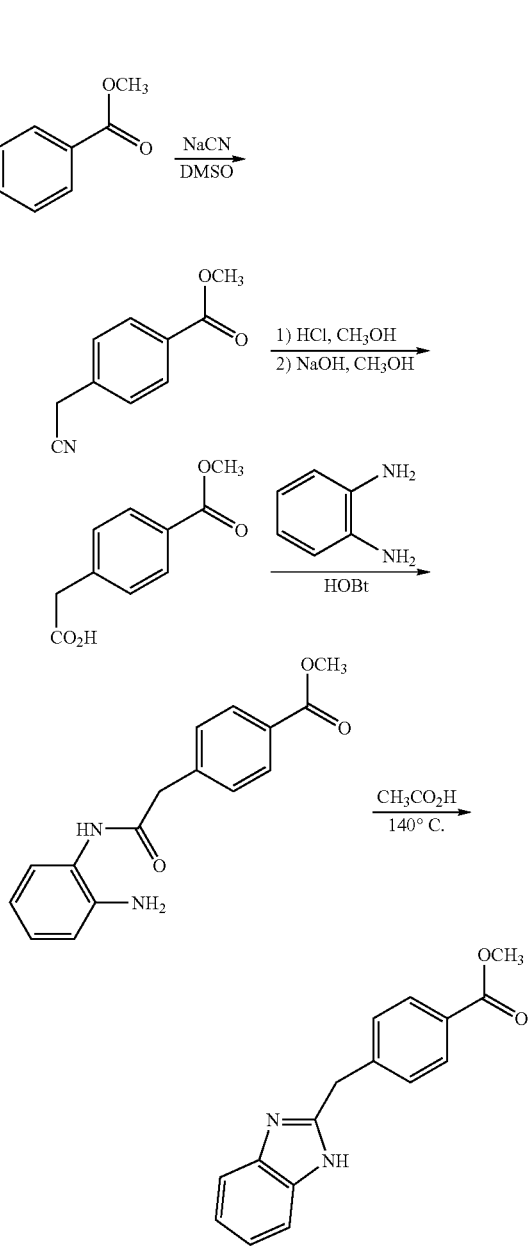

Step 1

Methyl 4-(cyanomethyl)benzoate

A solution of sodium cyanide (20 g, 0.41 mol) in dimethylsulfoxide at 40° C. was treated dropwise with a solution of methyl 4-(bromomethyl)benzoate (52 g, 0.227 mol) in dimethylsulfoxide, stirred for 90 min., cooled to room temperature, quenched with saturated aqueous sodium chloride and extracted with ethyl acetate. The combined extracts were washed with saturated aqueous sodium chloride, dried over sodium sulfate and concentrated under reduced pressure. Purification of the concentrate via column chromatography (silica, hexanes:ethyl acetate 0→5%) provided methyl 4-(cyanomethyl)benzoate (55%). ¹H NMR (400 MHz, CDCl₃): 8.05 (d, J=8 Hz, 2H); 7.42 (d, J=8 Hz, 2H); 3.93 (s, 3H); 3.81 (s, 2H). [M+H] 176

Step 2

2-(4-(Methoxycarbonyl)phenyl)acetic Acid

A stirred solution of methyl 4-(cyanomethyl)benzoate (22.0 g, 0.125 mol) in methanol (550 mL) was bubbled through with hydrogen chloride gas for 8 h under reflux conditions. The reaction mixture was cooled to 20° C., stirred for an additional 24 h and filtered. The filtrate was evaporated under reduced pressure. The resultant residue was dissolved in diethyl ether, washed sequentially with water and saturated aqueous sodium hydrogen carbonate, dried over sodium sulfate and evaporated to afford the methyl ester as a solid residue. ¹H NMR (400 MHz, CDCl₃): 8.00 (d, J=8 Hz, 2H); 7.35 (d, J=8.4 Hz, 2H); 3.91 (s 3H); 3.70 (s, 3H); 3.68 (s, 2H). GCMS: 209 (M+H). The methyl ester (8.21 g, 0.039 mmol) was dissolved in methanol, treated with sodium hydroxide (1.58 g, 0.039 mol), heated to 50° C., stirred for 4 h, cooled to room temperature, stirred for an additional 24 h and concentrated in vacuo. The resultant residue was partitioned between diethyl ether and water. The aqueous layer was acidified with concentrated HCl. The resultant precipitate was removed by filtration and dried overnight, under vacuum, to afford 2-(4-(methoxycarbonyl)phenyl)-acetic acid (80%) as an off-white solid. ¹H NMR (400 MHz, DSMO-d₆): 7.90 (d, J=8 Hz, 2H); 7.422 (d, J=8 Hz, 2H); 3.85 (s 3H) 3.68 (s, 2H). [M+H] 195

Steps 3 and 4

Methyl 4-((1H-Benzimidazol-2-yl)methyl)benzoate

A suspension of 2-(4-(methoxycarbonyl)phenyl)acetic acid (0.2 g, 1.03 mmol) in dichloromethane at 0° C. was treated with 1-(3-dimethylaminopropyl)-3-ethylcarbo-diimide hydrochloride (0.236 g, 1.237 mmol) and 1-hydroxybenzotriazole (HOBt) (0.153 g, 1.13 mmol), stirred for 30 min, treated with phenylenediamine (0.12 g, 1.12 mmol), stirred at room temperature for 24 h and quenched with water. The organic phase was separated, washed sequentially with saturated aqueous sodium hydrogen carbonate and saturated aqueous sodium chloride, dried over sodium sulfate and concentrated to dryness under reduced pressure to obtain the desired amide (68%) as an off-white solid. [M+H] 285. A solution of the amide (12.0 g, 0.04 mol) in acetic acid was heated to 140° C. for 1 h, cooled to room temperature and concentrated under reduced pressure. The resultant residue was neutralized with aqueous sodium hydroxide (1.0 N, 100 mL) and extracted with ethyl acetate. The extracts were combined, dried over sodium sulfate and concentrated under reduced pressure. Purification of the concentrate by column chromatography (silica, chloroform: methanol 0→5%) afforded the title product (47%) as a white solid. ¹H NMR (400 MHz, DMSO-d₆): 7.95 (d, J=8 Hz, 2H); 7.52 (s, 2H); 7.325 (d, J=8 Hz, 2H); 7.23 (m, 2H); 4.30 (s, 2H); 3.89 (s, 3H). [M+H] 267

Example 63

Preparation of Methyl 4-((1-Methyl-1H-benzimidazol-2-yl)methyl)benzoate

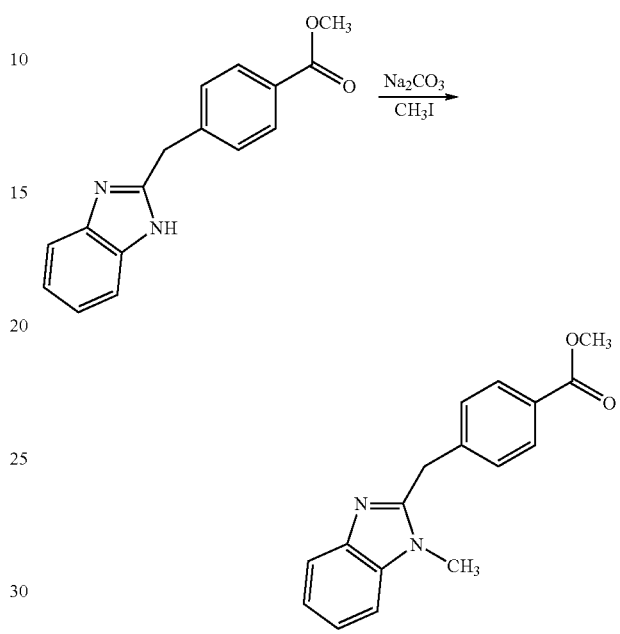

A solution of methyl 4-((1H-benzimidazol-2-yl)methyl) benzoate (0.2 g, 0.75 mmol) in acetone was treated with potassium carbonate (0.31 g, 2.2 mmol), cooled to 0° C., treated dropwise with and methyl iodide (0.070 mL, 1.1 mmol), heated at 40° C. for 12 h, cooled to room temperature, and filtered. The filtrate was evaporated under reduced pressure. Purification of the resultant residue by column chromatography (silica, chloroform) afforded the title product (28%). ¹H NMR (400 MHz, CDCl₃): 7.98 (d, J=8.4 Hz, 2H), 7.7 (m, 1H), 7.37 (m, 5H), 4.38 (s, 2H), 3.9 (s, 3H), 3.5 (s, 3H). [M+H] 281.

Example 64

Preparation of Methyl N-{4-[(1-methyl-1H-benzimidazol-2-yl)methyl]benzoyl}-serinate

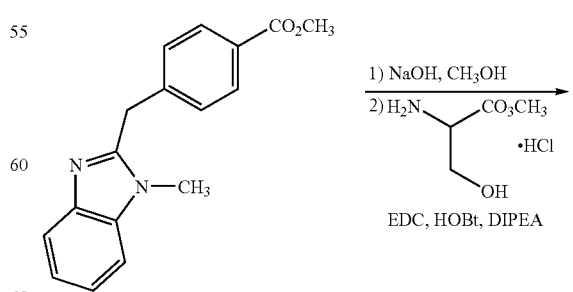

-continued

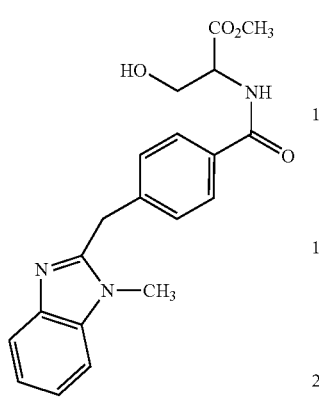

A solution of methyl 4-[(1-methyl-1H-benzimidazol-2-yl)methyl]benzoate (7.0 g, 25 mmol) in methanol was treated with 2.5 N sodium hydroxide, heated at reflux temperature for 2 h, cooled to room temperature and concentrated in vacuo. The residue was dissolved in water and acidified with 6N HCl solution and filtered. The filtercake was air dried to afford 4-[(1-methyl-1H-benzoimidazol-2-yl)methyl]benzoic acid in 81% yield; $^1$H NMR (400 MHz, DMSO-$d_6$): 7.90 (d, J=8 Hz, 2H), 7.57 (d, J=8 Hz, 1H), 7.49 (d, J=8 Hz, 1H), 7.40 (d, J=8 Hz, 2H), 7.17-7.20 (m, 2H), 4.39 (s, 2H), 3.70 (s, 3H). LCMS (ESI$^+$) 276 (MH+).

A stirred solution of said benzoic acid (0.5 g, 1.87 mmol) in DMF at 0° C., was treated sequentially with EDC (0.47 g, 2.1 mmol, 1.2 eq), HOBt (0.29 g, 2.1 mmol, 1.2 eq), DIPEA (0.8 g, 4.2 mmol, 2.5 eq) and serine methyl ester hydrochloride (0.33 g, 2.1 mmol, 1.2 eq), stirred overnight at room temperature and evaporated under reduced pressure. The resultant residue was partitioned between EtOAc and water. The phases were separated. The organic phase was washed successively with 1M HCl, water, saturated NaHCO$_3$ and brine, dried over Na$_2$SO$_4$ and concentrated in vacuo. This residue was purified by column chromatography (silica, CHCl$_3$:MeOH 4%) to afford the title product in 58% yield, identified by NMR and mass spectral analyses. $^1$H NMR (400 MHz, DMSO-$d_6$): 8.52 (d, J=8 Hz, 1H), 7.95 (s, 1H), 7.84 (d, J=8 Hz, 2H), 7.84 (d, J=8 Hz, 1H), 7.48 (d, J=8 Hz, 1H), 7.39 (d, J=8 Hz, 2H), 7.14-7.23 (m, 2H), 5.05 (t, J=7.2 Hz, 1H), 4.53 (m, 1H), 4.37 (s, 2H), 3.77 (t, J=7.2 Hz, 1H), 3.70 (s, 3H), 3.64 (s, 3H). LCMS (ESI$^+$) 367 (MH+).

Example 65

Preparation of Methyl {2-{4-[(1-methyl-1H-benzimidazol-2-yl)methyl]phenyl}-4,5-dihydro-1,3-oxazol-4-yl}carboxylate

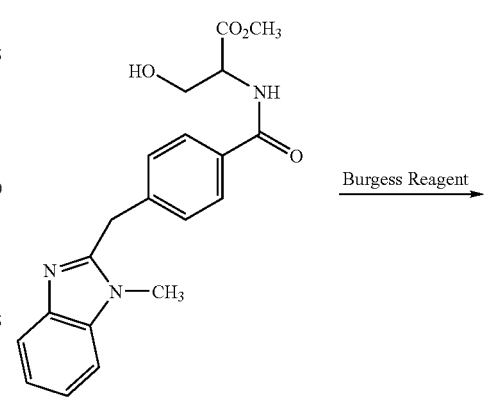

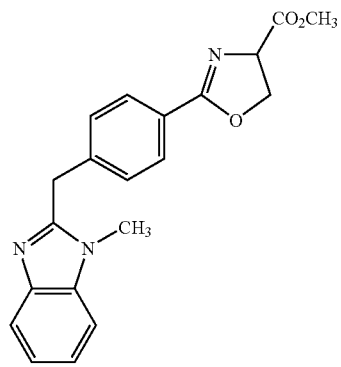

A stirred solution of methyl N-{4-[(1-methyl-1H-benzimidazol-2-yl)methyl]-benzoyl}-serinate (0.2 g, 0.55 mmol, 1.0 eq) in THF was treated with Burgess reagent (0.156 g, 0.65 mmol) and molecular sieves (1 g), stirred at 60° C. for 2 h, cooled to room temperature and concentrated under reduced pressure. The resultant residue was purified by column chromatography (silica, CHCl$_3$:MeOH 5%) to afford the title compound in 52% yield, identified by NMR and mass spectral analyses. $^1$H NMR (400 MHz, DMSO-$d_6$): 7.95 (s, 1H), 7.84 (d, J=8 Hz, 1H), 7.57 (d, J=8 Hz, 1H), 7.48 (d, J=8 Hz, 1H), 7.39 (d, J=8 Hz, 2H)), 7.16-7.21 (m, 1H), 5.60 (m, 1H), 4.95 (t, J=8.4 Hz, 1H), 4.57-4.60 (m, 1H), 4.38 (s, 2H), 4.26 (t, J=8.4 Hz, 1H), 3.78 (s, 3H). LCMS (ESI$^+$) 350 (MH+).

Example 66

Preparation of Methyl {2-[4-[(1-methyl-1H-benzimidazol-2-yl)methyl]phenyl}-1,3-oxazol-4-yl]carboxylate

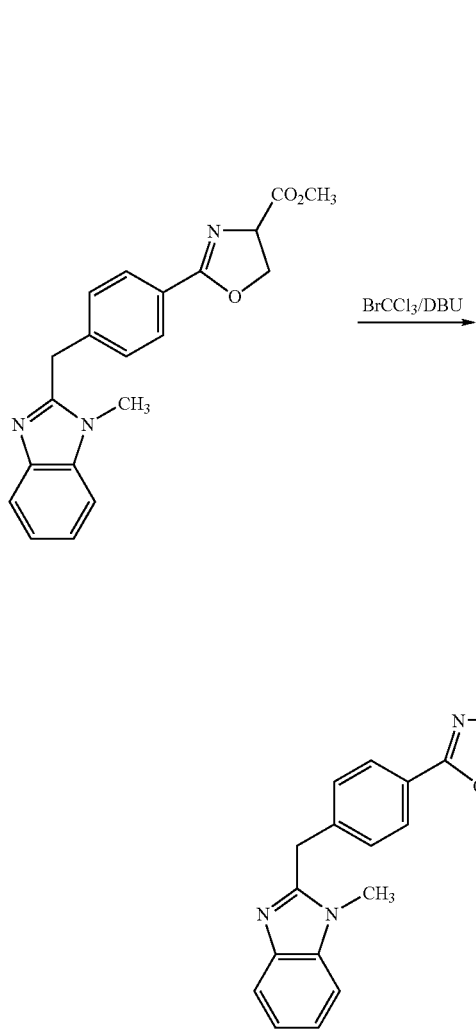

A stirred solution of methyl {2-{4-[(1-methyl-1H-benzimidazol-2-yl)methyl]-phenyl}-4,5-dihydro-1,3-oxazol-4-yl}carboxylate (1.5 g, 5 mmol) in CH$_2$Cl$_2$ was treated with bromotrichloromethane (1.22 g, 6 mmol) and DBU (0.70 g, 4.6 mol), stirred at room temperature overnight and concentrated in vacuo. The resultant residue was purified by column chromatography (silica, CHCl$_3$:MeOH 1%) to give the title compound in 15% yield, identified by NMR and mass spectral analyses. $^1$H NMR (400 MHz, CDCl$_3$): 8.2 (s, 1H), 8.06 (d, J=8.0 Hz, 2H), 7.3 (d, J=8.0 Hz, 2H), 7.27 (m, 4H), 4.3 (s, 2H), 3.95 (s, 3H), 3.63 (s, 3H). LCMS (ESI$^+$) 348 (MH+).

Example 67

Preparation of 1-Methyl-2-{4-[4-(pyrrolidin-1-ylmethyl)-1,3-oxazol-2-yl]benzyl}-1H-benzimidazole Fumarate

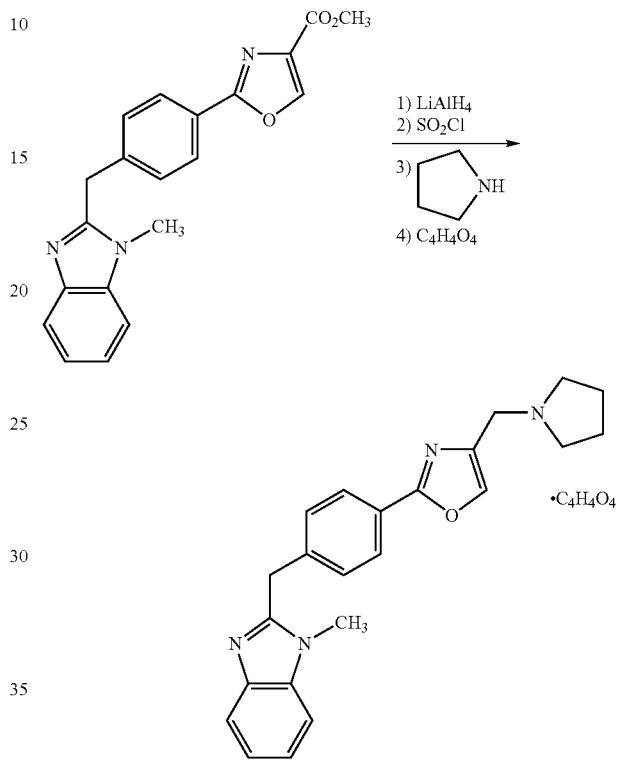

Using essentially the same procedures described in Examples 4, 5 and 6 and employing methyl {2-{4-[(1-methyl-1H-benzimidazol-2-yl)methyl]phenyl}-1,3-oxazol-4-yl}carboxylate in step 1 and pyrrolidine in step 3, the title compound is obtained and identified by NMR and mass spectral analyses. $^1$H NMR (300 MHz, DMSO-d$_6$ 373K): 7.93 (s, 1H); 7.92 (d, 2H); 7.58 (m, 1H); 7.44 (d, 2H); 7.47-7.42 (m, 1H); 7.19 (m, 2H); 6.64 (s, 2H); 4.38 (s, 2H); 3.72 (s, 3H); 3.71 (s, 2H); 2.71 (m, 4H); 1.76 (m, 4H). LCMS (ESI$^+$) 373.2 (MH+).

Example 68

Preparation of 4-(1H-Benzimidazol-1-ylmethyl)benzonitrile

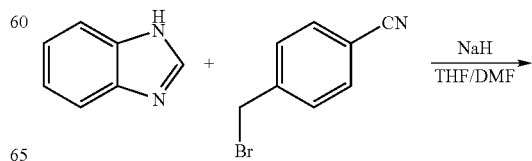

-continued

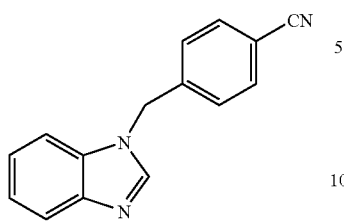

Using essentially the same procedure described in Example 1 and employing 4-(bromomethyl)benzonitrile, the title compound was obtained in 73% yield, identified by NMR and mass spectral analyses. $^1$H NMR (400 MHz, CDCl$_3$): 7.97 (s, 1H); 7.85 (d, J=8 Hz) 1H); 7.62 (d, J=8 Hz, 2H); 7.18-7.33 (m, 5H); 5.44 (s, 2H).

Example 69

Preparation of 4-(1H-Benzimidazol-1-ylmethyl)benzenecarbothioamide

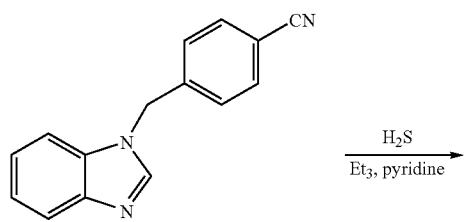

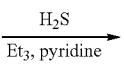

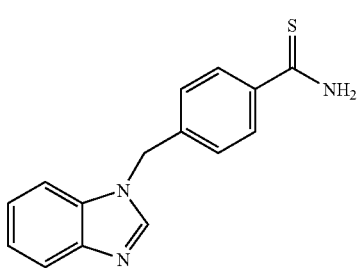

A stirred solution of 4-(1H-benzimidazol-1-ylmethyl)benzonitrile (0.50 g, 2.14 mmol) and triethylamine (Et$_3$N) (0.24 g, 2.37 mmol) in pyridine (2 mL), was bubbled through with H$_2$S (g) at room temperature for 2 h. The reaction mixture was diluted with water and filtered. The filtercake was washed with cold water and dried under vacuum to afford the title compound in 87% yield, identified by NMR and mass spectral analyses. $^1$H NMR (400 MHz, DMSO-d$_6$): 5.54 (s, 2H), 7.16-7.22 (m, 2H), 7.30 (d, J=8.8 Hz, 2H), 7.45-7.52 (m, 1H), 7.62-7.68 (m, 1H), 7.79 (d, J=8.8 Hz, 2H), 9.30 (bs, 1H), 9.80 (bs, 1H). LCMS (ESI$^+$) 268 (MH+).

Example 70

Preparation of 1-{4-[4-(Chloromethyl)-1,3-thiazol-2-yl]benzyl}-1H-benzimidazole

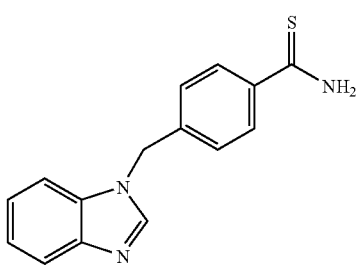

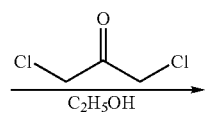

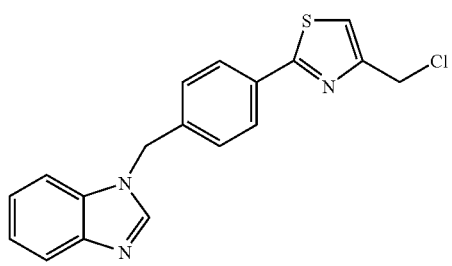

A stirred solution of 4-(1H-benzimidazol-1-ylmethyl)benzenecarbo-thioamide (0.50 g, 1.87 mmol) in ethanol was treated with 1,3-dichloroacetone (0.235 g, 1.85 mmol), heated at reflux temperature for 3 h, allowed to cool to room temperature and filtered. The filtercake was washed with cold ethanol and dried under vacuum to afford the title compound in 60% yield, identified by NMR and mass spectral analyses. $^1$H NMR (400 MHz, CDCl$_3$): 4.85 (s, 2H), 5.67 (s, 2H), 7.34-7.35 (m, 2H), 7.48 (d, J=7.6 Hz, 2H), 7.64-7.65 (m, 1H), 7.74-7.76 (m, 1H), 7.80 (s, 1H), 7.92 (d, J=7.6 Hz, 2H), 8.94 (s, 1H). LCMS (ESI$^+$) 340 (MH+).

Example 71

Preparation of 1-{4-[4-(Pyrrolidin-1-ylmethyl)-1,3-thiazol-2-yl]benzyl}-1H-benzimidazole Hydrochloride

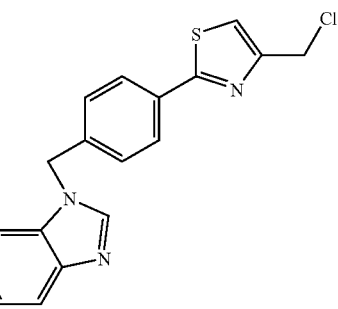

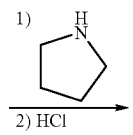

-continued

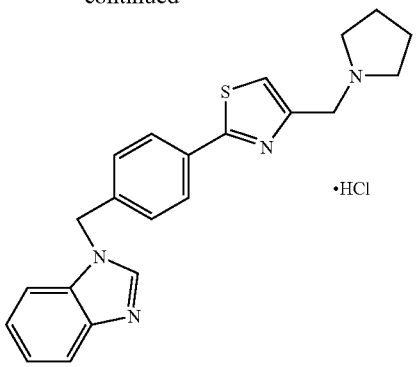

Pyrrolidine (0.260 g, 3.66 mmol) was added to 1-{4-[4-(chloromethyl)-1,3-thiazol-2-yl]benzyl}-1H-benzimidazole (0.250 g, 0.737 mmol) at 5° C. and the mixture was allowed to stir for 1 h, allowed to warm to room temperature and evaporated to dryness in vacuo. The resultant residue was purified by flash chromatography (silica, CHCl$_3$:MeOH 98:2) to afford the free amine of the title product. The purified material was stirred under HCl/ether and concentrated in vacuo to provide the title product, identified by NMR and mass spectral analyses. $^1$H NMR (300 MHz, DMSO-d$_6$): 0.99 (br s, 1H), 9.61 (br s, 1H), 7.99 (s, 1H), 7.99 (d, 2H), 7.76-7.93 (m, 2H), 7.59 (d, 2H), 7.46-7.56 (m, 2H), 5.80 (s, 2H), 4.51 (d, 2H), 3.42-3.54 (m, 2H), 3.17 (s, 2H), 1.81-2.05 (m, 4H). LCMS (ESI$^+$) 375.14 (MH+).

Examples 72-74

Preparation of 1-{4-[4-(Aminomethyl)-1,3-thiazol-2-yl]benzyl}-1H-benzimidazole Hydrochloride Compounds

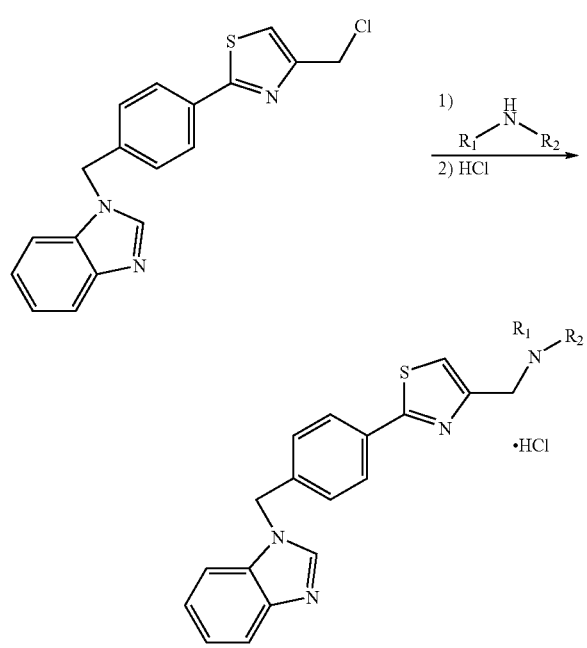

Using essentially the same procedure described in Example 71 and employing the desired amine, the compounds shown on Table VI were obtained and identified by NMR and mass spectral analyses.

TABLE VI

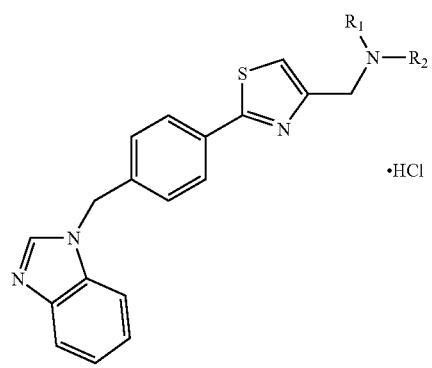

| Ex. No. | NR1R2 | [M + H] |
|---|---|---|
| 72 | 2-methylpyrrolidinyl | 389.21 |
| 73 | piperidinyl | 389.28 |
| 74 | azepanyl | 403.28 |

Example 75

Preparation of methyl 4-(1H-indol-1-ylmethyl)benzoate

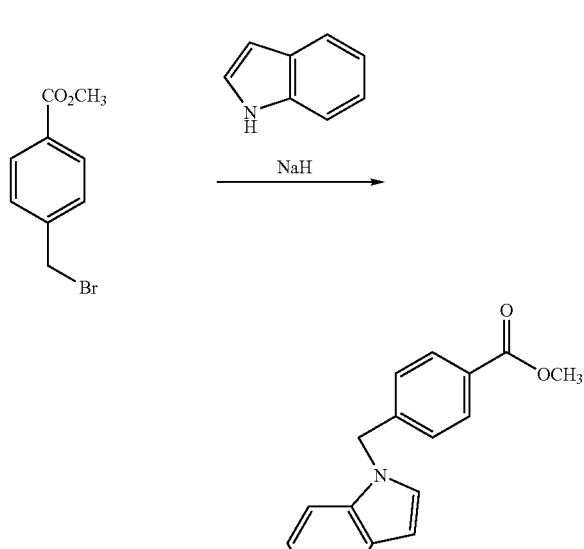

A solution of indole (5.6 g 48 mmol,) in DMF at 0° C. was treated with sodium hydride (1.84 g, 48 mmol), stirred for 10 minutes at room temperature, treated with methyl 4-(bromomethyl)benzoate (10 g, 44 mmol) and stirred at room temperature overnight. The reaction mixture was diluted with EtOAc, washed with saturated NaHCO$_3$, dried over MgSO$_4$ and concentrated in vacuo to give a solid residue. The resultant residue was purified by column chromatography (silica, EtOAc:hexanes, 30%) to give the title product in 91% yield, identified by NMR and mass spectral analyses. LCMS (ESI+) 266 (MH+).

Example 76

Preparation 4-(1H-indol-1-ylmethyl)benzoic acid

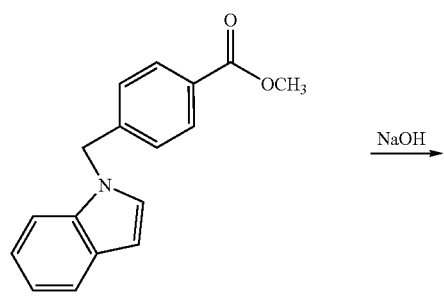

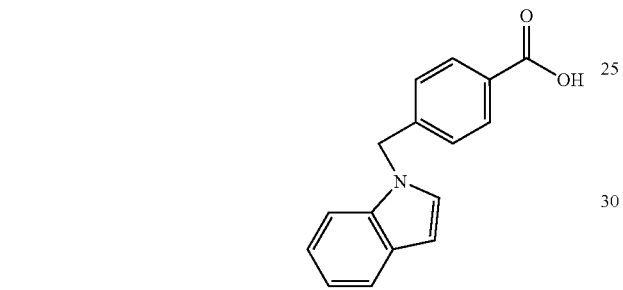

Methyl 4-(1H-indol-1-ylmethyl)benzoate (9.05 g; 34 mmol) was dissolved in MeOH/THF (1:1), treated with sodium hydroxide (1.36 g, 34 mmol) stirred at room temperature overnight and concentrated under reduced pressure. The resultant concentrate was diluted with 1N sodium hydroxide (50 mL), washed with EtOAc, acidified with concentrated HCl and extracted with EtOAc. The combined extracts were dried over MgSO₄ and concentrated to dryness to give the title product in 77% yield, identified by NMR and mass spectral analyses. LCMS (ESI+) 250 (MH+).

Example 77

Preparation of methyl 2-[4-(1H-indol-1-ylmethyl)phenyl]-4,5-dihydro-1,3-oxazole-5-carboxylate

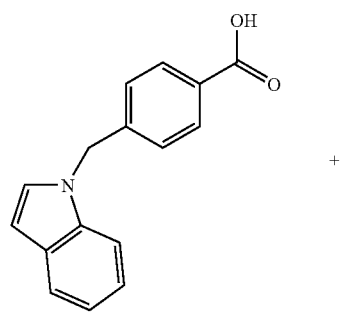

+

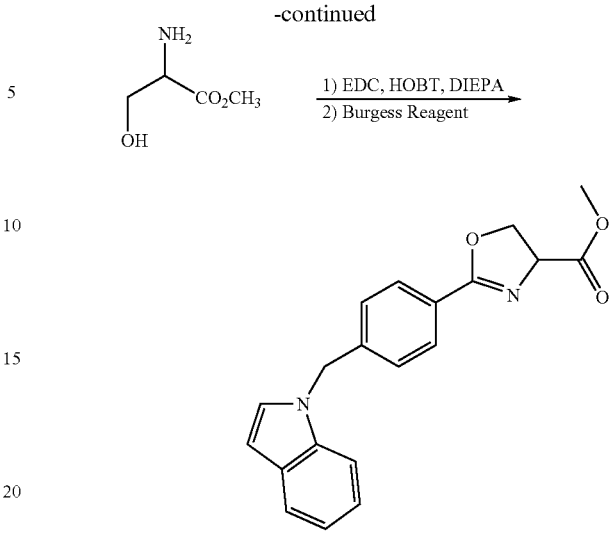

A stirred solution of 4-(1H-indol-1-ylmethyl)benzoic acid (2.5 g, 9.95 mmol) in DMF at 0° C. was treated sequentially with EDC (2.28 g, 11.94 mmol), HOBt (1.48 g, 10.95 mmol), DIPEA (1.48 g, 11.94 mmol) and serine methyl ester hydrochloride (1.86 g, 11.94 mol) and stirred at room temperature overnight and evaporated to dryness. The resultant residue was dissolved in EtOAc and water. The organic layer was washed successively with 1M HCl, water, saturated NaHCO₃ and brine, dried over Na₂SO₄ and concentrated under reduced pressure to afford methyl 2-hydroxy-3-({[4-(1H-indol-1-ylmethyl)phenyl]carbonyl}amino)propanoate as an amber residue. The residue (3.25 g, 9.22 mmol) in THF was treated with Burgess Reagent (3.29 g, 13.83 mmol) and activated 4 Å molecular sieves (1 g), stirred at 85° C. for 4 hours, cooled to room temperature, filtered over celite and concentrated under reduced pressure. The resultant residue was purified by column chromatography (silica, EtOAc:hexanes 25→50%) to give the title product in 73% yield, identified by NMR and mass spectral analyses. LCMS (ESI+) 335 (MH+).

Example 78

Preparation of methyl 2-[4-(1H-indol-1-ylmethyl)phenyl]-1,3-oxazole-4-carboxylate

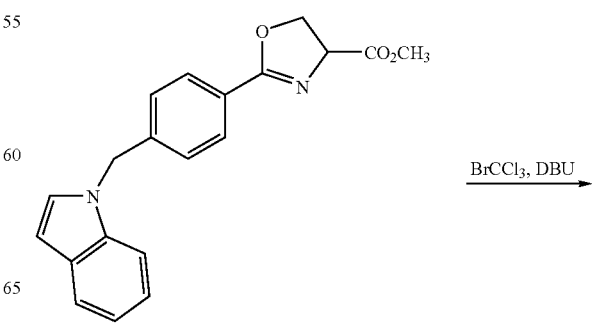

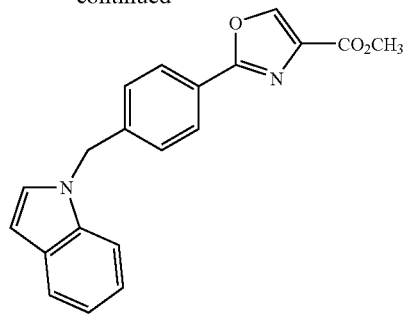

A solution of methyl 2-[4-(1H-indol-1-ylmethyl)phenyl]-4,5-dihydro-1,3-oxazole-5-carboxylate (2.15 g, 6.28 mmol) in $CH_2Cl_2$ is cooled to 0° C., treated with bromo trichloromethane (1.37 g, 6.91 mmol) and DBU (1.05 g, 6.91 mmol), stirred at room temperature overnight and concentrated under reduced pressure. The resultant residue was dissolved with saturated aqueous ammonium chloride and EtOAc. The layers were separated and the organic layer washed with water, brine, dried over $Na_2SO_4$ and concentrated under reduced pressure to give the title product in 73% yield, identified by NMR and mass spectral analyses. LCMS ($ESI^+$) 333 ($MH^+$).

Example 79

Preparation of 2-[4-(1H-indol-1-ylmethyl)phenyl]-1,3-oxazole-4-carboxylic acid

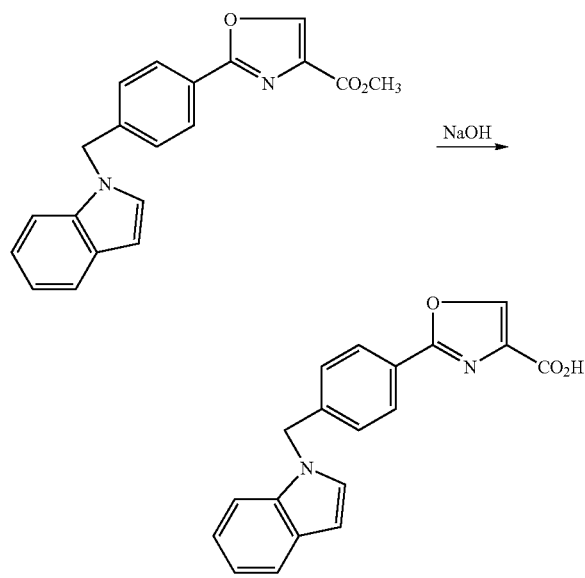

A solution of methyl 2-[4-(1H-indol-1-ylmethyl)phenyl]-1,3-oxazole-4-carboxylate (1.52 g; 4.57 mmol) in (1:1) MeOH:THF was treated with sodium hydroxide (4.57 g, 4.57 mmol) stirred at room temperature overnight and concentrated under reduced pressure. The resultant concentrate was diluted with 1N sodium hydroxide (50 mL), washed with EtOAc, acidified with concentrated HCl and extracted with EtOAc. The extracts were combined, dried over $MgSO_4$ and concentrated to dryness to give the title product in 91% yield, identified by NMR and mass spectral analyses. LCMS ($ESI^-$) 317 (MH−).

Example 80

Preparation of 1-{4-[4-(pyrrolidin-1-ylcarbonyl)-1,3-oxazol-2-yl]benzyl}-1H-indole

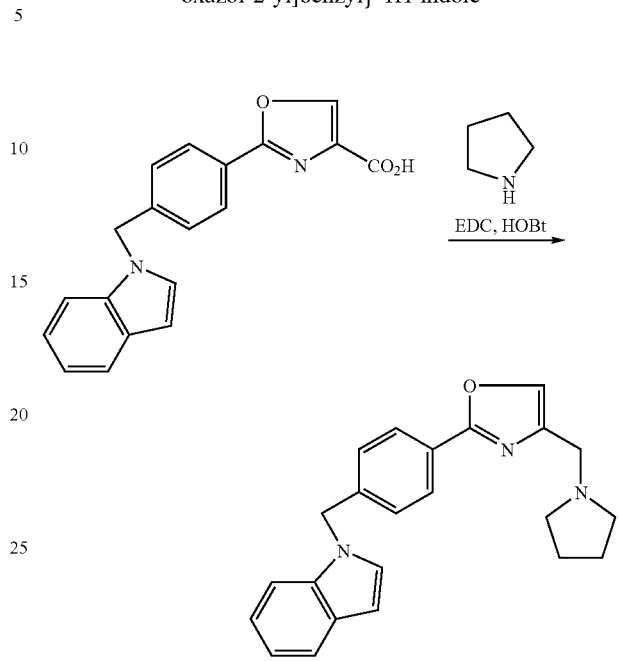

A stirred solution of 2-[4-(1H-indol-1-ylmethyl)phenyl]-1,3-oxazole-4-carboxylic acid (0.4 g, 1.26 mmol) in DMF was treated sequentially with EDC (0.29 g, 1.51 mmol), HOBt (0.186 g, 1.38 mmol) and pyrrolidine (0.098 g, 11.38 mol) was stirred at 80° C. overnight. The resultant residue was dissolved in EtOAc and water. The layers were separated and the aqueous layer was washed with EtOAC. The combined organic layers were washed successively with water, saturated sodium chloride, dried over $Mg_2SO_4$ and concentrated under reduced pressure to give a crude oil. The oil was purified by column chromatography (silica, MeOH:$CH_2Cl_2$ 5%) to give the title product in 44% yield, identified by NMR and mass spectral analyses. LCMS ($ESI^+$) 372 ($MH^+$).

Example 81

Preparation of 1-{4-[4-(pyrrolidin-1-ylmethyl)-1,3-oxazol-2-yl]benzyl}-1H-indole Hydrochloride

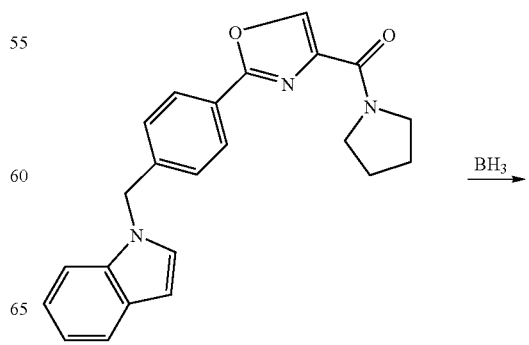

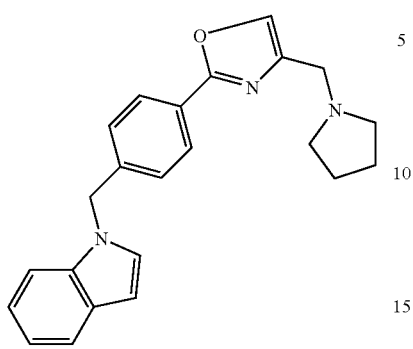

A stirred solution of 1-{4-[4-(pyrrolidin-1-ylcarbonyl)-1,3-oxazol-2-yl]benzyl}-1H-indole (0.18 g, 0.49 mmol) in THF was treated with 1.0M Borane-THF (0.834 g, 9.8 mmol), stirred at room temperature overnight and concentrated under reduced pressure. The resultant residue was dissolved in MeOH, treated with 1.0M HCl:Et$_2$O and stirred at 60° C. for 2 hours. The solvent was concentrated under reduced pressure and the resultant oil diluted with EtOAc and saturated sodium bicarbonate. The layers were separated and the aqueous layer washed with EtOAc. The combined organic layers were washed with saturated sodium chloride, dried over Mg$_2$SO$_4$ and concentrated under reduced pressure to give a crude oil. The oil was purified by column chromatography (silica, (10% NH$_4$OH:MeOH):CH$_2$Cl$_2$ 5%) to give the title product in 20% yield, identified by NMR and mass spectral analyses. LCMS (ESI$^+$) 358 (MH$^+$).

Example 82

Preparation of ethyl 2-amino-1,3-oxazole-4-carboxylate

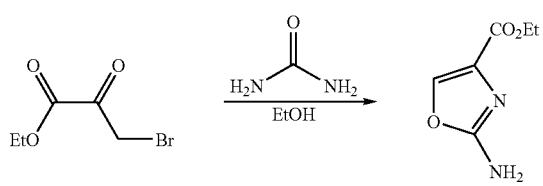

A stirred solution of ethyl bromopyruvate (50.2 g, 257.2 mmol) in EtOH was treated with urea (23.2 g, 385.8 mmol) refluxed overnight and concentrated under reduced pressure. The resultant residue was dissolved in EtOAC and water. The layers were separated and the aqueous layer washed with EtOAC. The combined organic layers were washed successively with saturated sodium chloride, dried over Mg$_2$SO$_4$ and concentrated under reduced pressure to give the title product in 85% yield, identified by NMR and mass spectral analyses. LCMS (ESI$^+$) 157.1 (MH$^+$).

Example 83

Preparation of ethyl 2-chloro-1,3-oxazole-4-carboxylate

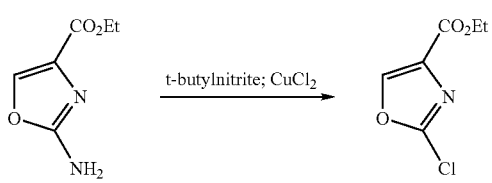

A stirred solution of tert-butyl nitrite (1.0 g, 9.61 mmol) and copper (II) chloride (1.29 g, 9.61 mmol) in CH$_3$CN was treated with ethyl 2-amino-1,3-oxazole-4-carboxylate (1.0 g, 6.4 mmol) stirred 2 hours at room temperature, heated to 80° C. for 30 minutes and concentrated under reduced pressure. The resultant residue was dissolved in EtOAc and water. The layers were separated and the organic layer washed with saturated sodium chloride, dried over Mg$_2$SO$_4$ and concentrated under reduced pressure to give the title product in 56% yield, identified by NMR and mass spectral analyses. LCMS (ESI$^+$) 175 (MH$^+$).

Example 84

Preparation of ethyl 2-[4-(hydroxymethyl)phenyl]-1,3-oxazole-4-carboxylate

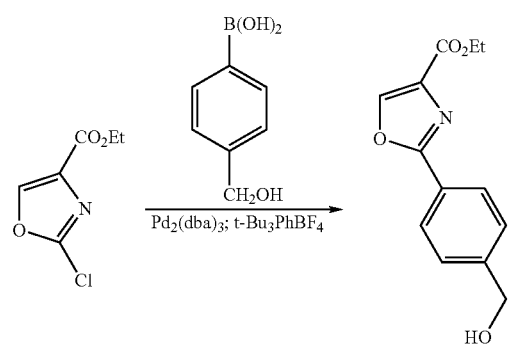

A solution of ethyl 2-chloro-1,3-oxazole-4-carboxylate (0.59 g, 3.36 mmol) in dioxane was treated with 4-(hydroxymethyl)phenyl boronic acid (0.766 g, 5.04 mmol), K$_2$CO$_3$ (0.929 g, 6.72 mmol), t-Bu$_3$PhBF$_4$ (0.049 g, 0.168 mmol) heated to 80° C. then treated with Pd$_2$(dba)$_3$ (0.154 g 0.168 mmol) and stirred overnight at 90° C. The reaction mixture was diluted with EtOAc, washed with water, saturated sodium chloride, dried over MgSO$_4$ and concentrated in in vacuo. The resultant residue was purified by flash chromatography (silica, EtOAc:hexanes 20→50%) to give the title product in 70% yield, identified by NMR and mass spectral analyses. LCMS (ESI$^+$) 248 (MH$^+$).

Example 85

Preparation of ethyl 2-[4-(chloromethyl)phenyl]-1,3-oxazole-4-carboxylate

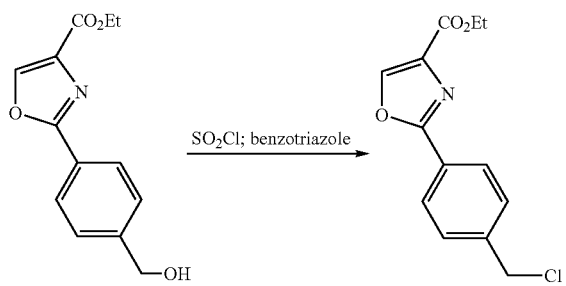

A solution of ethyl 2-[4-(hydroxymethyl)phenyl]-1,3-oxazole-4-carboxylate (0.467 g, 1.89 mmol) in $CH_2Cl_2$ was treated with a solution of thionyl chloride (0.281 g, 2.36 mmol) and benzotriazole (0.281 g, 2.36 mmol) in $CH_2Cl_2$, and stirred 6 hours at room temperature. The reaction was diluted with $CHCl_3$, filtered over Celite and concentrated under vacuum. The resultant residue was purified by flash chromatography (silica, MeOH:$CH_2Cl_2$ 5%) to give the title product in 82% yield, identified by NMR and mass spectral analyses. LCMS (ESI$^+$) 266 (MH$^+$).

Example 86

Preparation of 2-[4-(1H-indazol-1-ylmethyl)phenyl]-1,3-oxazole-4-carboxylic acid

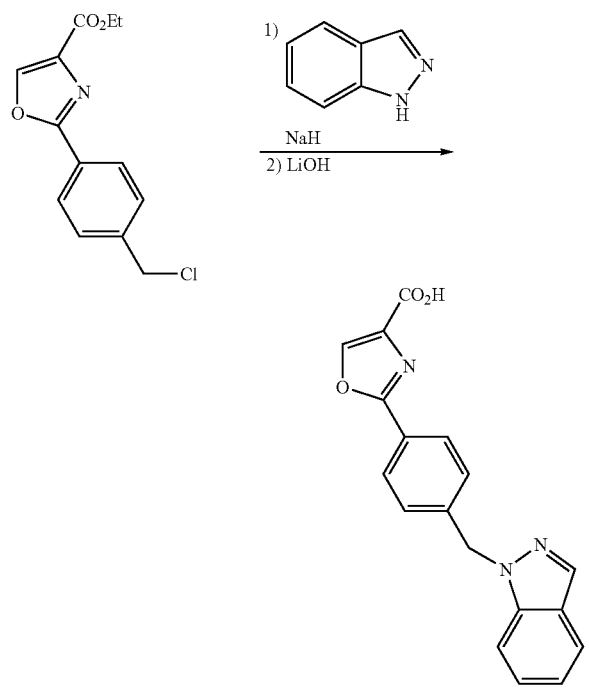

A solution of indazole (0.244 g, 2.07 mmol) in DMF at 0° C. was treated with sodium hydride (0.076 g, 1.98 mmol), stirred for 10 minutes at room temperature, treated with ethyl 2-[4-(chloromethyl)phenyl]-1,3-oxazole-4-carboxylate (0.5 g, 1.88 mmol) and stirred at 80° C. overnight. The reaction mixture was diluted with EtOAc, washed with water, dried over MgSO$_4$ and concentrated in vacuo to give a solid residue. The resultant residue was purified by column chromatography (silica, EtOAc:hexanes, 50%) to give ethyl 2-[4-(1H-indazol-1-ylmethyl)phenyl]-1,3-oxazole-4-carboxylate as white solid. The resulting solid (0.45 g, 1.29 mmol) was dissolved in 1:1 MeOH:THF treated with 1.0 M LiOH for 3 hours at 60° C. and concentrated in in vacuo. The resulting residue was diluted with water, treated with 1.0 M HCl and filtered to afford the title product 92% yield, identified by NMR and mass spectral analyses. LCMS (ESI$^+$) 320 (MH$^+$).

Example 87

Preparation of pyrrolidine, 1-[[2-[4-(1H-indazol-1-ylmethyl)phenyl]-4-oxazolyl]carbonyl]Hydrochloride

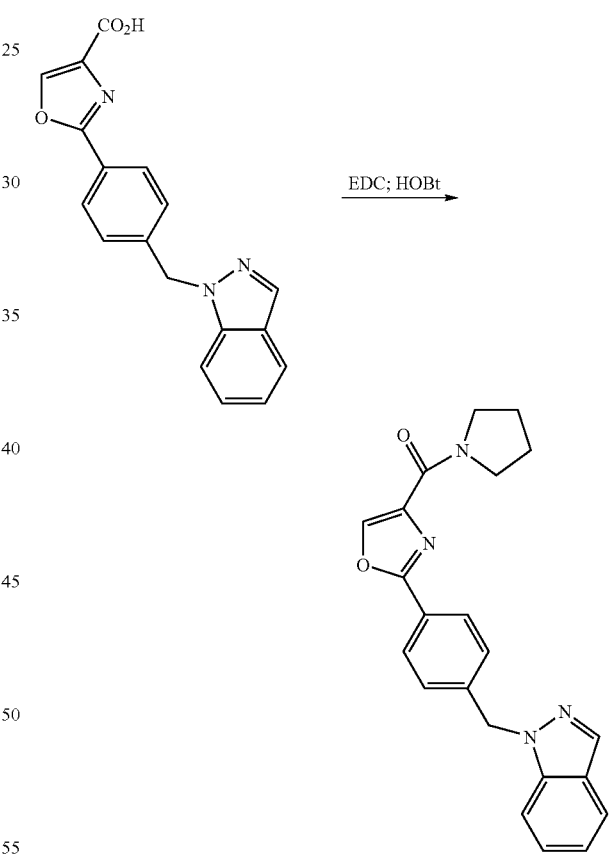

A solution of 2-[4-(1H-indazol-1-ylmethyl)phenyl]-1,3-oxazole-4-carboxylic acid (0.125 g, 0.391 mmol) in DMF was treated sequentially with EDC (0.09 g, 0.47 mmol), HOBt (0.058 g, 0.43 mmol and pyrrolidine (0.031 g, 0.43 mol), stirred at 80° C. for 4 hours and evaporated to dryness. The resultant residue was dissolved in EtOAc and water. The layers were separated and the organic layer was washed successively with 1M HCl, water, saturated aqueous NaHCO$_3$ and brine, dried over Na$_2$SO$_4$ and concentrated under reduced pressure. The resultant residue was purified by flash chromatography (silica, MeOH:CH$_2$Cl$_2$ 5%) to give the title product in 47% yield, identified by NMR and mass spectral analyses. LCMS (ESI$^+$) 373.1 (MH$^+$).

Example 88

Preparation of 1-{4-[4-(pyrrolidin-1-ylmethyl)-1,3-oxazol-2-yl]benzyl}-1H-indazole

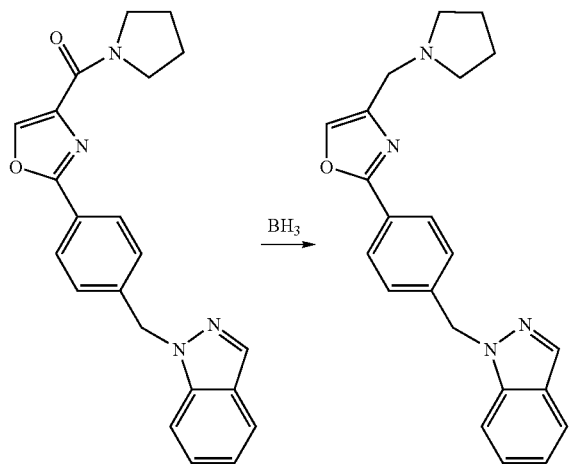

Using essentially the same procedures described in Example 81, and employing pyrrolidine and 1-[[2-[4-(1H-indazol-1-ylmethyl)phenyl]-4-oxazolyl]carbonyl], the title compound was obtained and identified by mass spectral analyses LCMS (ESI$^+$) 359 (MH$^+$).

Example 89

Preparation of 2-[4-(hydroxymethyl)phenyl]-1,3-oxazole-4-carboxylic acid

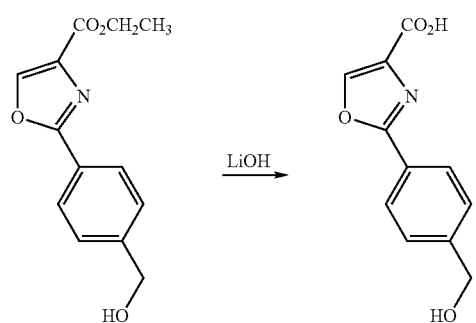

A solution of ethyl 2-[4-(hydroxymethyl)phenyl]-1,3-oxazole-4-carboxylate (2.5 g, 10.1 mmol) in 1:1 MeOH:THF was treated with 1.0 M LiOH:H$_2$O and stirred at room temperature overnight and concentrated in in vacuo. The resulting residue was diluted with water, treated with 1.0 M HCl and filtered to afford the title product 91% yield, identified by NMR and mass spectral analyses. LCMS (ESI$^+$) 219 (MH$^+$).

Example 90

Preparation of {4-[4-(pyrrolidin-1-ylcarbonyl)-1,3-oxazol-2-yl]phenyl}methanol

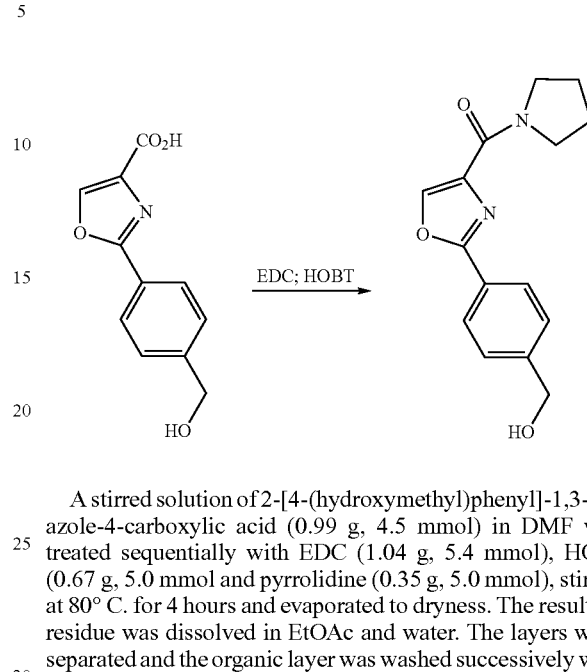

A stirred solution of 2-[4-(hydroxymethyl)phenyl]-1,3-oxazole-4-carboxylic acid (0.99 g, 4.5 mmol) in DMF was treated sequentially with EDC (1.04 g, 5.4 mmol), HOBt (0.67 g, 5.0 mmol and pyrrolidine (0.35 g, 5.0 mmol), stirred at 80° C. for 4 hours and evaporated to dryness. The resultant residue was dissolved in EtOAc and water. The layers were separated and the organic layer was washed successively with 1M HCl, water, saturated NaHCO$_3$ and brine, dried over Na$_2$SO$_4$ and concentrated under reduced pressure The resultant residue was purified by flash chromatography (silica, EtOAc:hexanes 25%) to give the title product in 84% yield, identified by NMR and mass spectral analyses. LCMS (ESI$^+$) 273 (MH$^+$).

Example 91

Preparation of 2-[4-(chloromethyl)phenyl]-4-(pyrrolidin-1-ylcarbonyl)-1,3-oxazole

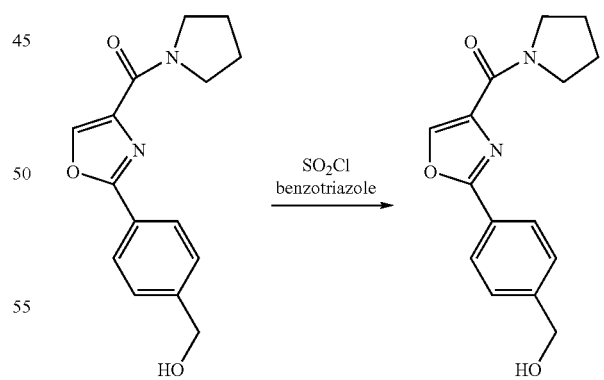

A solution of 2-[4-(hydroxymethyl)phenyl]-4-(pyrrolidin-1-ylcarbonyl)-1,3-oxazole (0.467 g, 1.89 mmol) in CH$_2$Cl$_2$ was treated with a solution of thionyl chloride (0.281 g, 2.36 mmol) and benzotriazole (0.281 g, 2.36 mmol) in CH$_2$Cl$_2$, stirred for 6 hours at room temperature, diluted with CHCl$_3$, filtered over Celite and concentrated under vacuum, The resultant residue was purified by flash chromatography (silica, MeOH:CH$_2$Cl$_2$ 5%) to give the title product in 82%

Example 92

Preparation of [4-(4-{[(2S)-2-methylpyrrolidin-1-yl]carbonyl}-1,3-oxazol-2-yl)phenyl]methanol

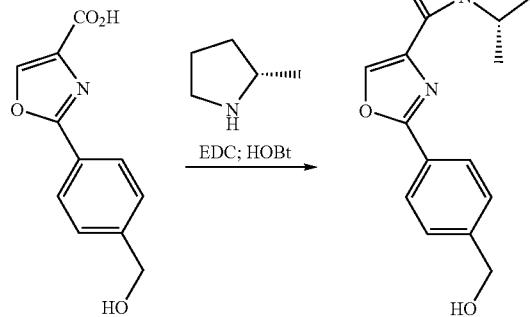

Using essentially the same procedures described in Example 90 and employing (S)-2-methylpyrrolidine as reactant, the title compound was obtained and identified by mass spectral analyses LCMS (ESI$^+$) 287.1.

Example 93

Preparation of [4-(4-{[(2R)-2-methylpyrrolidin-1-yl]carbonyl}-1,3-oxazol-2-yl)phenyl]methanol

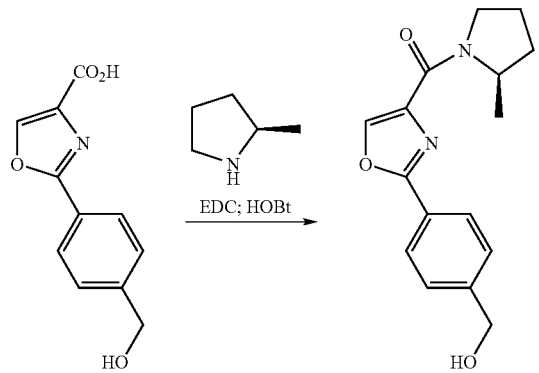

Using essentially the same procedures described in Example 90 and employing (R)-2-methylpyrrolidine as reactant, the title compound was obtained and identified by mass spectral analyses LCMS (ESI$^+$) 287.1.

Examples 94-102

Preparation of 1-{4-[4-(Aminomethyl)-1,3-oxazol-2-yl]benzyl}-1H-heterocylic Hydrochloride Compounds

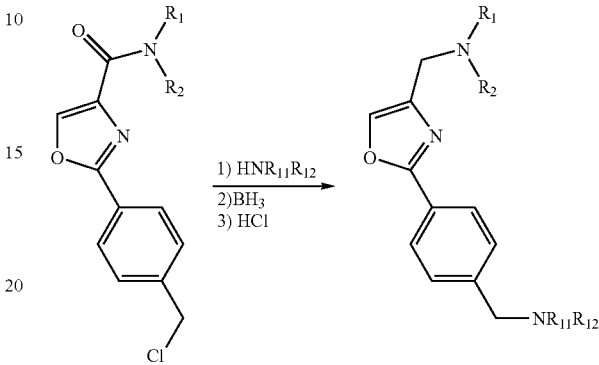

Using essentially the same procedure described in Example 86 for introduction of $NR_{11}R_{12}$ and Example 88 for reduction of the amide, the compounds shown on Table VII were obtained and identified by and mass spectral analyses.

TABLE VII

| Ex. No. | $NR_{11}R_{12}$ | $NR_1R_2$ | [M + H] |
|---|---|---|---|
| 94 | indazole | (R)-2-methylpyrrolidine | 373.1 |
| 95 | 5-fluoro-indazole | (R)-2-methylpyrrolidine | 391.1 |
| 96 | 6-fluoro-indazole | (R)-2-methylpyrrolidine | 391.1 |
| 97 | indazole | (S)-2-methylpyrrolidine | 373.2 |
| 98 | 5-fluoro-indazole | (S)-2-methylpyrrolidine | 391.2 |
| 99 | 6-fluoro-indazole | (S)-2-methylpyrrolidine | 391.2 |
| 100 | 5-fluoro-indazole | Pyrrolidine | 377.1 |
| 101 | 6-fluoro-indazole | Pyrrolidine | 377.1 |
| 102 | 5-aminomethyl-indazole | Pyrrolidine | 388.0 |

Example 103

Preparation of ethyl 2-[4-(chloromethyl)phenyl]-1,3-oxazole-5-carboxylate

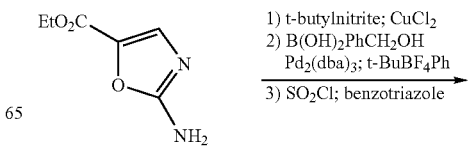

-continued

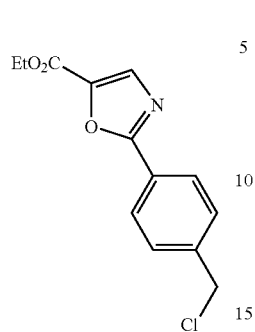

Using essentially the same procedures described in Examples 83, 84, and 85 and employing ethyl 2-amino-1,3-oxazole-5-carboxylate and 4-(hydroxymethyl)phenylboronic acid as reactants, the title compound was obtained and identified by mass spectral analyses LCMS (ESI⁺) 266.0

Examples 104-113

Preparation of 1-{4-[5-(aminomethyl)-1,3-oxazol-2-yl]benzyl}-1H-benzimidazole Hydrochloride Compounds

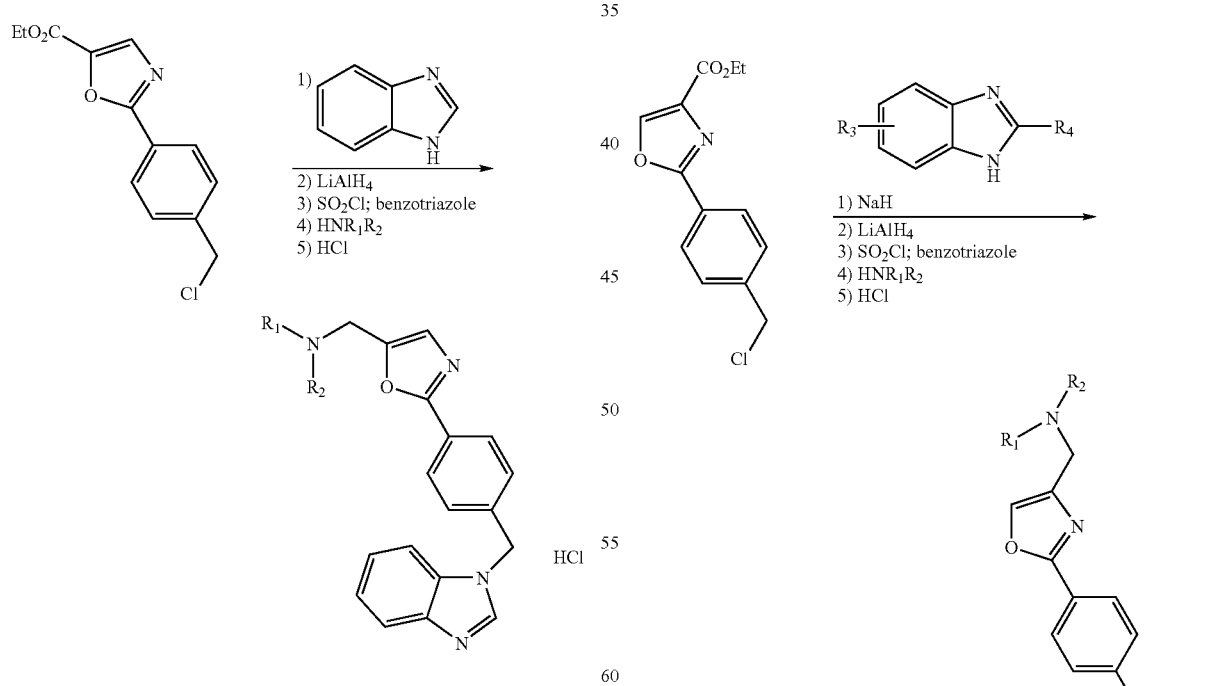

Using essentially the same procedures described in Examples 1, 4, 85, 6 and employing ethyl 2-[4-(chloromethyl)phenyl]-1,3-oxazole-5-carboxylate as the starting material with the desired amine, the compounds shown on Table V were obtained and identified by mass spectral analyses.

TABLE VIII

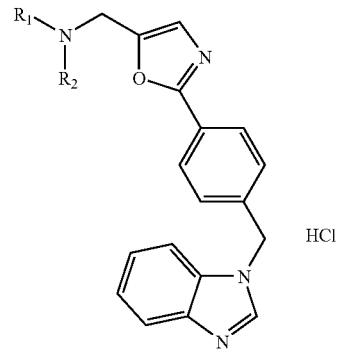

| Ex. No. | NR1R2 | [M + H] |
|---|---|---|
| 104 | pyrrolidinyl | 359.2 |
| 105 | 2-methylpyrrolidine | 373.2 |
| 106 | (S)-2-methylpyrrolidine | 373.2 |
| 107 | piperidine | 373.2 |
| 108 | (R)-2-methylpyrrolidine | 373.2 |
| 109 | 3-methylpiperidine | 387.2 |
| 110 | 1,3,3-trimethyl-6-azabicyclo[3.2.1]octane | 441.3 |
| 111 | azepane | 387.2 |
| 112 | N-methylethanamine | 347.1 |
| 113 | diethylamine | 361.2 |

Preparation of 1-{4-[4-(aminomethyl)-1,3-oxazol-2-yl]benzyl}-substituted-benzimidazole Hydrochloride Compounds Examples 114-134

TABLE IX

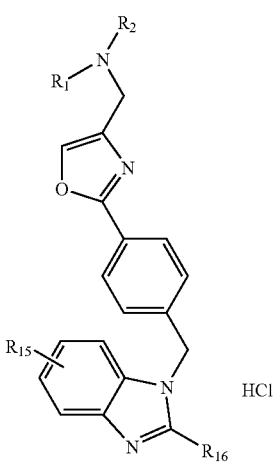

| Ex. No. | R15 | R16 | NR1R2 | [M + H] |
|---|---|---|---|---|
| 114 | H | CF3 | pyrrolidine | 427.1 |
| 115 | H | phenyl | pyrrolidine | 435.2 |
| 116 | H | CF3 | (R)-2-methylpyrrolidine | 441.2 |
| 117 | H | phenyl | (S)-2-methylpyrrolidine | 449.2 |
| 118 | H | CF3 | (S)-2-methylpyrrolidine | 441.2 |
| 119 | H | phenyl | (R)-2-methylpyrrolidine | 449.2 |
| 120 | H | CF3 | azepane | 455.2 |
| 121 | H | phenyl | azepane | 463.2 |
| 122 | H | CF3 | piperidine | 441.1 |
| 123 | H | phenyl | piperidine | 449.2 |
| 124 | 5-OCH3 6-OCH3 | H | pyrrolidine | 389.1 |
| 125 | 5-CH3 6-CH3 | H | pyrrolidine | 373.2 |
| 126 | 5-OCH3 6-OCH3 | H | (R)-2-methylpyrrolidine | 403.2 |
| 127 | 5-CH3 6-CH3 | CH3 | (R)-2-methylpyrrolidine | 401.2 |
| 128 | 5-OCH3 6-OCH3 | H | (S)-2-methylpyrrolidine | 403.2 |

TABLE IX-continued

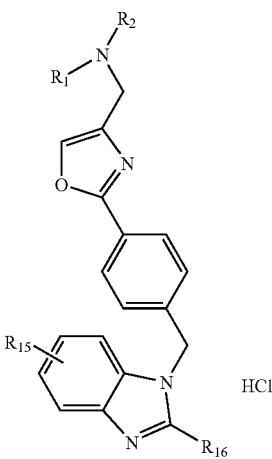

| Ex. No. | R15 | R16 | NR1R2 | [M + H] |
|---|---|---|---|---|
| 129 | 5-CH3 6-CH3 | H | (S)-2-methylpyrrolidine | 387.2 |
| 130 | 5-CH3 6-CH3 | CH3 | (S)-2-methylpyrrolidine | 401.2 |
| 131 | 5-OCH3 6-OCH3 | H | azepane | 417.2 |
| 132 | 5-CH3 6-CH3 | H | azepane | 401.2 |
| 133 | 5-CH3 6-CH3 | CH3 | azepane | 415.2 |
| 134 | 5-CH3 6-CH3 | CH3 | pyrrolidine | 387.2 |

Example 135

[1-(4-bromobenzyl)-1H-benzimidazole

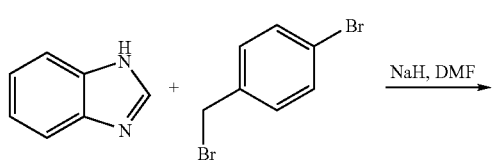

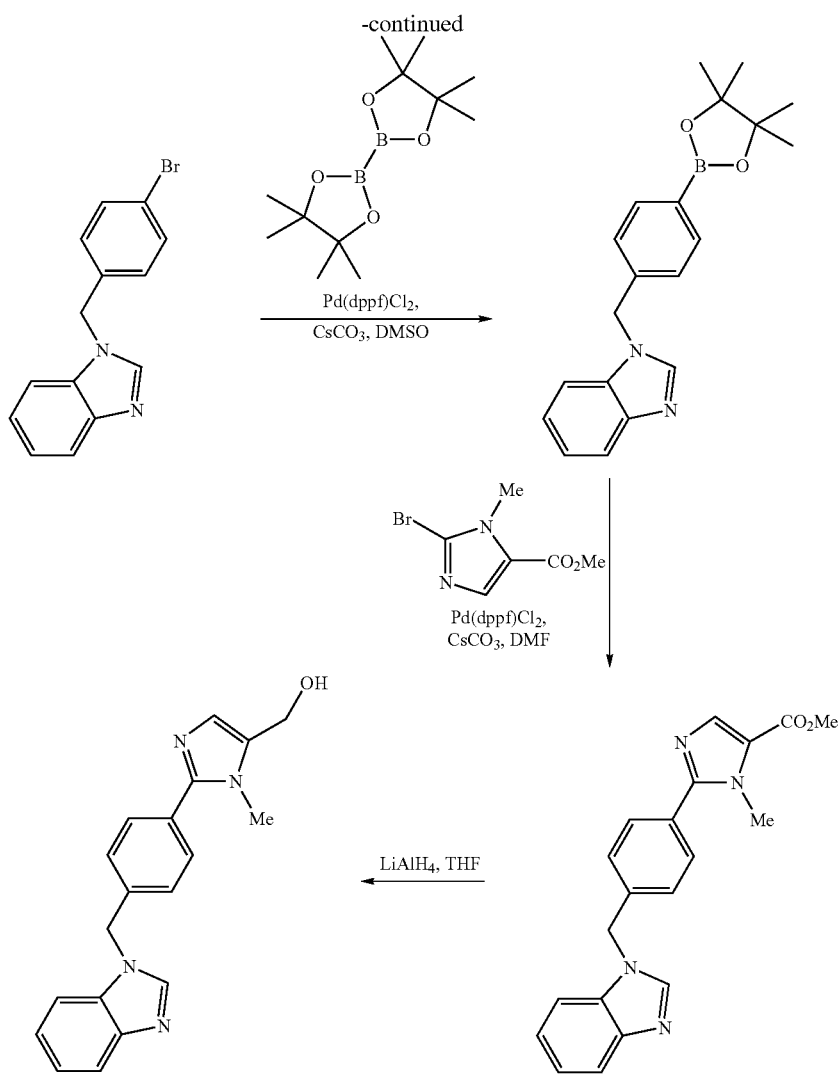

To a suspension of sodium hydride (60% in mineral oil, 1.86 g, 46.6 mmol) in dry DMF (5 mL) under nitrogen and cooled to 0° C. was added a solution of benzimidazole (5.0 g, 42.2 mmol) in DMF (15 mL) and the reaction mixture was allowed to stir for 30 min at room temperature. The reaction mixture was cooled to 0° C. and a solution of 4-bromobenzyl bromide (10.6 g, 42.4 mmol) in DMF (10 mL) was added dropwise and the reaction mixture was allowed to warm to room temperature overnight. The solvent was removed under reduced pressure and the residue partitioned between saturated aqueous sodium chloride and ethyl acetate. The organic layer was washed with saturated aqueous sodium chloride, dried ($Na_2SO_4$) and evaporated. The crude product was triturated with ethyl ether and recovered by filtration. Yield: 70%. LCMS ($ESI^+$) 387.2 and 389.2 (MH+).

Example 136

1-[4-(4,4,5,5-tetramethyl)-[1,3,2]-dioxaborolan-2-yl]-benzyl-1H-benzoimidazole

A mixture of [1-(4-bromobenzyl)-1H-benzimidazole (1.71 g, 5.97 mmol), bis-pinacolato diboron (12.14 g, 47.8 mmol), $Pd(dppf)_2Cl_2$ (490 mg, 0.6 mmol), and potassium acetate (1.75 g, 17.9 mmol) in dry DMSO (50 mL) under nitrogen was heated to 80° C. and the reaction mixture was allowed to stir for 1 h. The reaction mixture was allowed to cool to room temperature and diluted with ethyl acetate (100 mL). The reaction mixture was filtered and the organic solution was washed with saturated aqueous sodium chloride, dried ($Na_2SO_4$) and then solvent removed under reduced pressure. The crude product was purified by flash column chromatography (silica, petroleum ether/ethyl acetate 8:2, then dichloromethane/methanol 9:1) to afford the title compound (90%). LCMS ($ESI^+$) 335.2 (MH);

Example 137

2-(4-benzoimidazol-1-ylmethyl-phenyl)-3-methyl-3H-imidazole-4-carboxylic acid methyl ester To a solution of 1-[4-(4,4,5,5-tetramethyl)-[1,3,2]-dioxaborolan-2-yl]-benzyl-1H-benzoimidazole (0.527 g, 1.5 mmol) and 2-bromo-3-methyl-3H-imidazole-4-carboxylic acid methyl ester (Anichem LLC, 0.328 g, 1.5 mmol) in anhydrous DMF (5 mL) under nitrogen was added Pd(dppf)$_2$Cl$_2$ (53 mg, 0.065 mmol) and cesium carbonate (0.786 g, 2.4 mmol) and the reaction mixture was heated to 80° C. and allowed to stir for 7 h. The reaction mixture was cooled to room temperature, diluted with ethyl acetate, and the solids filtered off. The filtrate was washed with water, dried (Na$_2$SO$_4$) and the solvent removed under reduced pressure. Purification by flash chromatography (silica, dichloromethane/methanol 99:1→97:3) provided the title compound (40%). LCMS (ESI$^+$) 347.2 (MH+).

Example 138

[2-(4-Benzoimidazol-1-ylmethyl-phenyl)-3-methyl-3H-imidazol-4-yl]-methanol

To a suspension of lithium aluminum hydride (60.8 mg, 1.6 mmol) in anhydrous tetrahydrofuran (4 mL) under nitrogen cooled to −5° C. was added dropwise a solution of 2-(4-benzoimidazol-1-ylmethyl-phenyl)-3-methyl-3H-imidazole-4-carboxylic acid methyl ester (280 mg, 0.8 mmol) in anhydrous tetrahydrofuran (2 mL) over 10 min and the reaction mixture was allowed to stir at for 1 h. The reaction mixture was quenched with water (0.06 mL), aqueous sodium hydroxide (2.5 N, 0.21 mL), and again water (0.06 mL), stirred for 30 min, then diluted with tetrahydrofuran (20 mL) and left overnight without stirring. The reaction mixture was diluted with dichloromethane (20 mL) and methanol (20 mL) and the solid was filtered off. The filtrate was evaporated under reduced pressure and the crude product was used in the next step without further purification. LCMS (ESI$^+$) 319.2 (MH+).

Examples 139-140

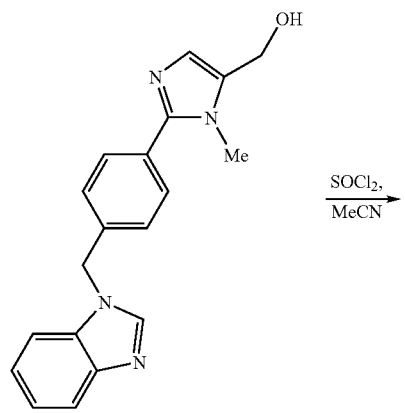

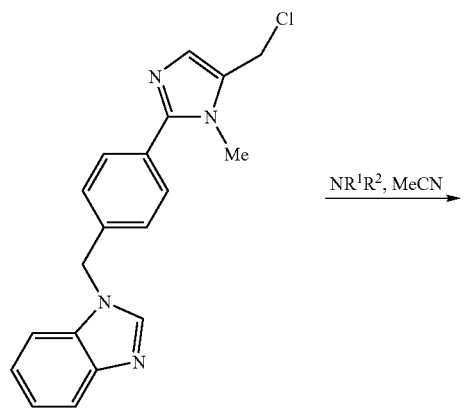

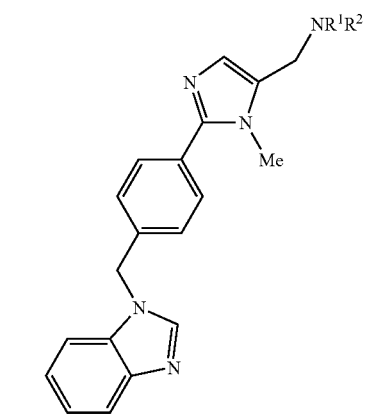

Example 139

1-[4-(1-Methyl-5-pyrrolidin-1-ylmethyl-1H-imidazol-2-yl)-benzyl]-1H-benzoimidazole fumarate salt A solution of [2-(4-Benzoimidazol-1-ylmethyl-phenyl)-3-methyl-3H-imidazol-4-yl]-methanol in thionyl chloride (12 ml) was heated at reflux for 30 min. The reaction mixture was evaporated under reduced pressure and the crude product was used in next step without further purification. To a suspension of 1-[4-(5-chloromethyl-1-methyl-1H-imidazol-2-yl)-benzyl]-1H-benzoimidazole in dry acetonitrile (10 mL) cooled to 0° C. was added pyrrolidine (0.67 mL, 8 mmol) and the reaction mixture was allowed to stir at room temperature for 20 min. The solvent was evaporated under reduced pressure and the residue was partitioned between dichloromethane and 5% aqueous sodium bicarbonate. The organic layer was washed with water, dried (Na$_2$SO$_4$) and the solvent removed under reduced pressure. Purification by flash column chromatography (silica, dichloromethane/methanol 95:5→90:10) followed by conversion to the fumarate salt. $^1$H NMR (300 MHz, DMSO-d$_6$): 9.67 (s, 1H), 7.96 (s, 1H), 7.93-7.84 (m, 2H), 7.75 (m, 4H), 7.57 (m, 2H), 6.63 (s, 2H), 5.90 (s, 2H), 4.67 (s, 2H), 3.80 (s, 3H), 3.57 (m, 2H), 3.20 (m, 2H), 2.14-1.84 (m, 4H). LCMS (ESI$^+$) 372.3 (MH+).

Example 140

(5)-1-(4-(1-methyl-5-((2-methylpyrrolidin-1-yl)methyl)-1H-imidazol-2-yl)benzyl)-1H-benzo[d]imidazole fumarate salt Using essentially the same procedures described in Example 139 and employing ethyl 2-[4-(chloromethyl)phenyl]-1,3-oxazole-5-carboxylate and (S)-2-methylpyrrolidine as starting materials, the title compound was obtained and identified by $^1$H NMR and mass spectral analyses. $^1$H NMR (300 MHz, DMSO-$d_6$+TFA): 8.43 (s, 1H), 7.65-7.69 (m, 1H), 7.58-7.64 (m, 2H), 7.53-7.58 (m, 1H), 7.35-7.47 (m, 2H), 7.17-7.27 (m, 2H), 6.84 (s, 1H), 6.57 (s, 2H), 5.56 (s, 2H), 3.91 (d, 1H), 3.64 (s, 3H), 3.21 (d, 1H), 2.74-2.91 (m, 1H), 2.32-2.46 (m, 1H), 2.12 (q, 1H), 1.85-2.00 (m, 1H), 1.51-1.69 (m, 2H), 1.25-1.39 (m, 1H), 1.08 (d, 3H). LCMS (ESI$^+$) 386.38 (MH+).

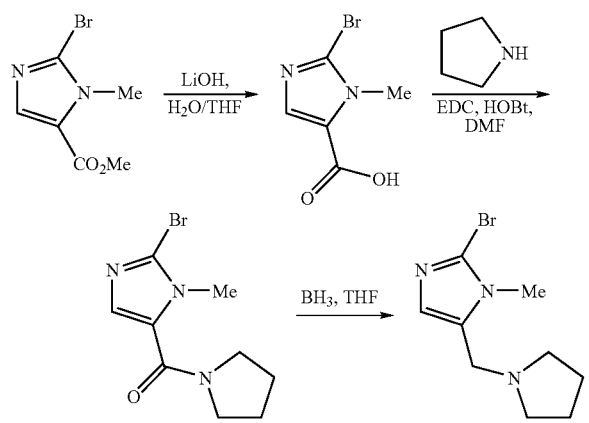

Example 141

(2-bromo-1-methyl-1H-imidazole-5-yl)(pyrrolidin-1-yl)methanone

To a suspension of methyl 2-bromo-1-methyl-1H-imidazole-5-carboxylate (2.18 g, 10 mmol) in tetrahydrofuran (60 mL) and water (6 mL) was added lithium hydroxide (0.72 mg, 30 mmol) and the reaction mixture was allowed to stir at room temperature for 2.5 h. The solvent was removed under reduced pressure and water was added followed by formic acid, the resulting precipitate was filtered, washed with water and dried under vacuum overnight to afford the 2-bromo-1-methyl-1H-imidazole-5-carboxylic acid (82%). $^1$H-NMR (300 MHz, CDCl$_3$): 7.79 (s, 1H), 3.91 (s, 3H). LCMS (ESI$^+$) 205.0 (MH+). To a solution of the carboxylic acid (1.68 g, 8.2 mmol) in anhydrous tetrahydrofuran (24 mL) was added EDC (1.53 g, 9.9 mmol) followed by HOBt (1.22 g, 9.1 mmol) and the reaction mixture was allowed to stir for 1 h at room temperature. A solution of pyrrolidine (1.03 ml, 12.4 mmol) in tetrahydrofuran (8 mL) was added and the reaction mixture was allowed to stir overnight at room temperature. The solvent was removed under reduced pressure and residue partitioned between ethyl acetate and 1 M aqueous potassium carbonate. The organic layer was dried (Na$_2$SO$_4$) and solvent evaporated under reduced pressure. Purification by flash column chromatography (silica, EtOAc/MeOH 9:1) afforded the title compound (95%). $^1$H NMR (300 MHz, CDCl$_3$): 7.79 (s, 1H), 3.92 (s, 3H), δ 3.35 (bs, 4H), δ 1.97 (bs, 4H). LCMS (ESI$^+$) 257.0 (MH+).

Example 142

2-bromo-1-methyl-5-((pyrrolidin-1-yl)-1H-imidazole

To a solution of (2-bromo-1-methyl-1H-imidazole-5-yl)(pyrrolidin-1-yl)methanone (200 mg, 0.78 mmol) in anhydrous tetrahydrofuran at room temperature (5 mL) was added borane tetrahydrofuran complex (1 M in THF, 8.0 mL) and the reaction mixture was heated to reflux and allowed to stir for 8 h. The reaction mixture was cooled to 0° C. and quenched with slow addition of HCl/MeOH and then then heated to reflux for 3 h. The solvent was evaporated under reduced pressure and residue partitioned between dichloromethane and 1 M aqueous sodium hydroxide. The organic layer was washed with saturated aqueous sodium chloride, dried (Na$_2$SO$_4$) and solvent removed under reduced pressure. Purification by flash column chromatography (silica, EtOAc/MeOH 10:2) gave the title compound (91%). $^1$H-NMR (300 MHz, CDCl$_3$): 6.83 (s, 1H), 3.61 (s, 3H), 3.53 (s, 2H), 2.50-2.40 (m, 4H), 1.79-1.72 (m, 4H). LCMS (ESI$^+$) 244.0 (MH+).

Examples 143-146

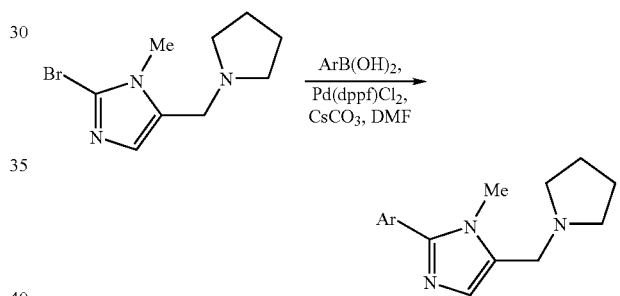

General procedure for the Suzuki coupling. To a solution of 2-bromo-1-methyl-5-((pyrrolidin-1-yl)-1H-imidazole (85 mg, 0.35 mmol) and the boronic acid (0.35 mmol) in anhydrous acetonitrile (3 mL) was added Pd(dppf)$_2$Cl$_2$ (0.007 mmol, 6 mg) and 2 M Na$_2$CO$_3$ (0.5 ml) and the reaction mixture was degassed with nitrogen and heated to 150° C. under microwave irradiation for 20 min. The reaction mixture was cooled to room temperature, the solid was filtered, and the filtrate evaporated under reduced pressure. The residue was dissolved in ethyl acetate and washed with saturated aqueous sodium chloride, dried (Na$_2$SO$_4$) and solvent removed under reduced pressure. Purification by flash column chromatography (silica, dichloromethane:methanol 9:1) was followed by conversion of the product to the fumarate salt. The title compounds were obtained and identified by $^1$H NMR and mass spectral analyses.

Example 143

1-Methyl-2-phenyl-5-pyrrolidin-1-ylmethyl-1H-imidazole fumarate salt $^1$H NMR (300 MHz, DMSO-d$_6$): 7.58-7.71 (m, 2H), 7.38-7.58 (m, 3H), 7.01 (s, 1H), 6.58 (s, 2H), 3.87 (s, 2H), 3.69 (s, 3H), 2.66-2.80 (m, 4H), 1.73-1.85 (m, 4H). LCMS (ESI$^+$) 242.42 (MH+).

Example 144

4-(1-Methyl-5-pyrrolidin-1-ylmethyl-1H-imidazol-2-yl)-benzonitrile fumarate salt $^1$H NMR (300 MHz, DMSO-$d_6$+Na2CO3): 7.86-7.95 (m, 4H) 6.96 (s, 1H) 3.74 (s, 3H) 3.61 (s, 2H) 2.43-2.49 (m, 4H) 1.66-1.76 (m, 4H). LCMS (ESI$^+$) 267.2 (MH+).

Example 145

2-(4-Fluoro-phenyl)-1-methyl-5-pyrrolidin-1-ylmethyl-1H-imidazole fumarate salt $^1$H NMR (300 MHz, DMSO-$d_6$): 7.62-7.72 (m, 2H), 7.25-7.36 (m, 2H), 6.97 (s, 1H), 6.59 (s, 2H), 3.83 (s, 2H), 3.67 (s, 3H), 2.64-2.73 (m, 4H), 1.77 (dt, 4H). LCMS (ESI$^+$) 260.41 (MH+).

Example 146

2-Biphenyl-4-yl-1-methyl-5-pyrrolidin-1-ylmethyl-1H-imidazole fumarate salt $^1$H NMR (300 MHz, DMSO-$d_6$): 7.70-7.83 (m, 6H), 7.45-7.55 (m, 2H), 7.36-7.45 (m, 1H), 6.94 (s, 1H), 6.60 (s, 2H), 3.74 (s, 3H), 3.71 (s, 2H), 1.69-1.80 (m, 4H). LCMS (ESI$^+$) 318.25 (MH+).

Examples 147-151

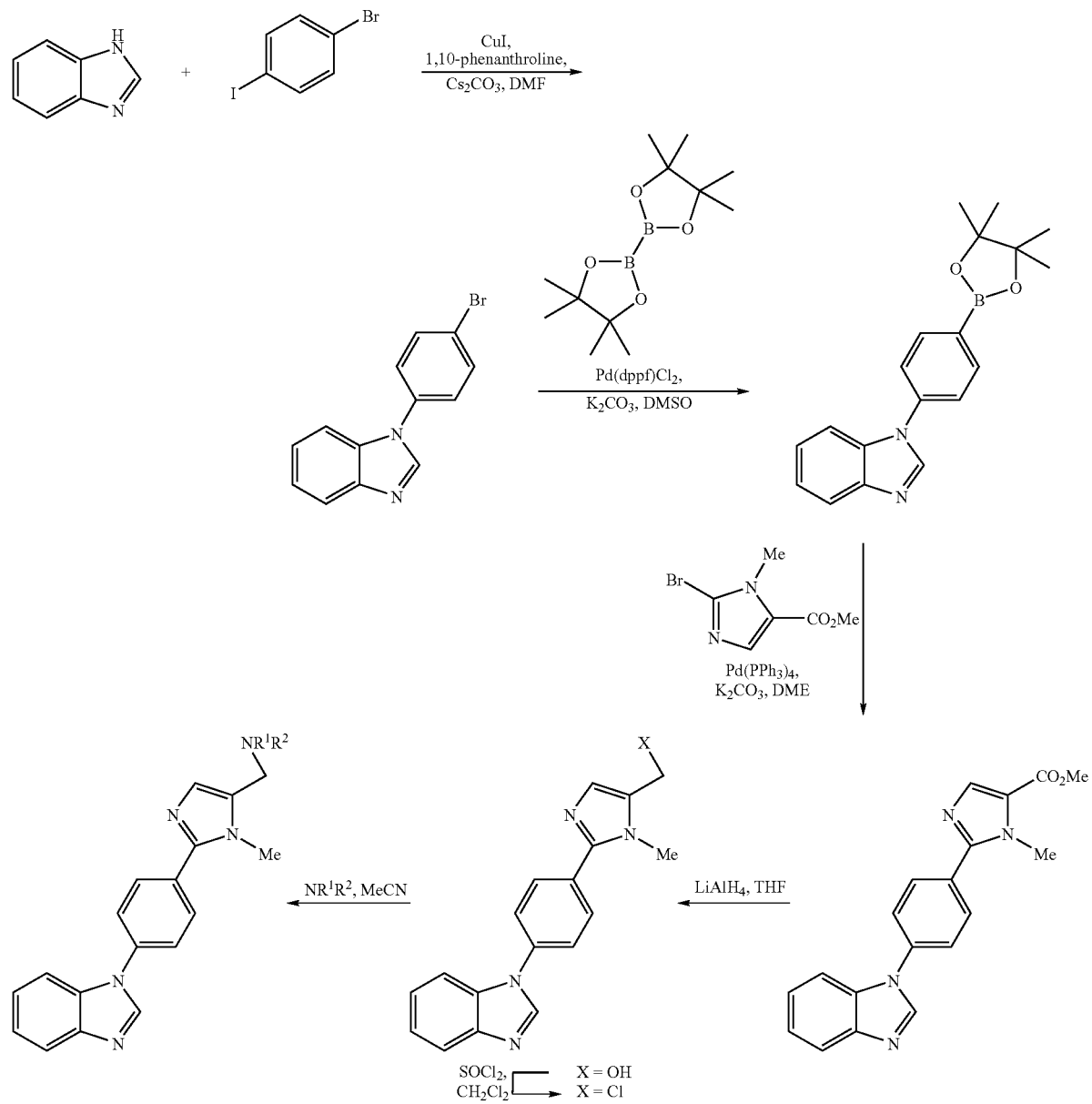

Example 147

1-(4-Bromo-phenyl)-1H-benzoimidazole

To a mixture of copper iodide (0.16 g, 0.85 mmol) and 1,10-phenanthroline (0.31 g, 1.7 mmol) in anhydrous DMF (4.2 mL) was added benzimidazole (1.00 g, 8.5 mmol), 1-bromo-4-iodobenzene (2.88 g, 10.1 mmol), and cesium carbonate (5.53 g, 17 mmol) and the reaction mixture was heated to 110° C. and allowed to stir for 40 h. The reaction mixture was cooled to room temperature and the solvent was evaporated under reduced pressure. The residue was partitioned between water and dichloromethane and the organic layer was separated, dried ($Na_2SO_4$) and the solvent removed under reduced pressure. Purification by flash column chromatography (silica, petroleum ether:ethyl acetate 1:1) provided the title compound (64%). LCMS ($ESI^+$) 274.2 (MH+).

Example 148

1-[4-(4,4,5,5-Tetramethyl-[1,3,2]dioxaborolan-2-yl)-phenyl]-1H-benzoimidazole To a solution of 1-(4-bromo-phenyl)-1H-benzoimidazole (0.68 g, 2.5 mmol) in anhydrous DMSO (30 mL) was added bis(pinacolato)diboron (5.0 g, 19 mmol) followed by Pd(dppf)$Cl_2$ (0.2 g, 0.25 mmol) and potassium carbonate (1.03 g, 7.5 mmol) and the reaction mixture was heated at 80° C. for 1 h. The reaction mixture was cooled and diluted with ethyl acetate and filtered. The filtrate was washed with water, saturated aqueous sodium chloride, dried ($Na_2SO_4$), and the solvent removed under reduced pressure. Purification by flash column chromatography (silica, petroleum ether:ethyl acetate 8:2→1:1 then dichloromethane:methanol 10:0→9:1) afforded the title compound (60%) as a 1:1 mixture of boronic ester/boronic acid; used directly in the next step. LCMS ($ESI^+$) 321.2 (MH+ ester); 238.2 (MH+ acid).

Example 149

2-(4-Benzoimidazol-1-yl-phenyl)-3-methyl-3H-imidazole-4-carboxylic acid methyl ester To a solution of 1-[4-(4,4,5,5-tetramethyl-[1,3,2]dioxaborolan-2-yl)-phenyl]-1H-benzoimidazole (0.43 g, 1.5 mmol) and 2-bromo-3-methyl-3H-imidazole-4-carboxylic acid methyl ester (0.25 g, 1.15 mmol) in DME (9 mL) was added tetrakis(triphenylphosphine)palladium(0) (0.07 g, 0.057 mmol) and 2 M aqueous potassium carbonate (1.4 mL) and the reaction mixture was heated at 90° C. for 12 h. The reaction mixture was cooled to room temperature and diluted with ethyl acetate. The reaction mixture was filtered and the filtrate washed with water, dried ($Na_2SO_4$), and the solvent removed under reduced pressure. Purification by flash column chromatography (silica, petroleum ether:ethyl acetate 7:3→1:1 then dichloromethane:methanol 99:1→97:3) provided the title compound (36%). LCMS ($ESI^+$) 332.2 (MH+).

Example 150

[2-(4-Benzoimidazol-1-yl-phenyl)-3-methyl-3H-imidazol-4-yl]-methanol

Following essentially the same procedure described in Example 138 and employing 2-(4-benzoimidazol-1-yl-phenyl)-3-methyl-3H-imidazole-4-carboxylic acid methyl ester as starting material, the title compound was obtained (52%) and identified by mass spectral analyses. LCMS ($ESI^+$) 305.2 (MH+).

Example 151

1-[4-(1-Methyl-5-pyrrolidin-1-ylmethyl-1H-imidazol-2-yl)-phenyl]-1H-benzoimidazole fumarate salt Following essentially the same procedure described in Example 139 and employing [2-(4-Benzoimidazol-1-yl-phenyl)-3-methyl-3H-imidazol-4-yl]-methanol and pyrrolidine as starting materials, the title compound was obtained and identified by $^1H$ NMR and mass spectral analyses. $^1H$ NMR (300 MHz, DMSO-$d_6$): 8.63 (s, 1H); 7.91 (d, 2H); 7.81 (d, 2H); 7.81-7.77 (m, 1H); 7.71 (m, 1H); 7.36 (m, 2H); 7.00 (s, 1H); 6.60 (s, 2H); 3.78 (s, 2H); 3.77 (s, 3H); 2.63 (m, 4H); 1.76 (m, 4H). LCMS ($ESI^+$) 358.2 (MH+).

Biological Example

Evaluation of Methyl Histamine Binding in Human Histamine-3 Receptor Cell Line The affinity of test compounds for the histamine-3 ($H_3$) receptor is evaluated in the following manner. Stably transfected HEK293T cells are grown in DMEM containing 10% heat inactivated FBS and G-418 (500 ug/ml). Cells are scraped from the plate, transferred to centrifuge tubes, washed one time in PBS by centrifugation in a Sorvall RT7 Plus centrifuge (2000 rpm 10 minutes, 4° C.). The resulting pellets are stored at 80° C. until ready for use. Cells are re-suspended in buffer (50 mM Tris pH=7.5) and placed in a Dounce homogenizer, douncing ten times to homogenize cells. The homogenate is spun down by centrifugation (Sorvall RT7 Plus, 1800 rpm 10 minutes, 4° C.). The supernatant is placed in a Corex tube and spun down by centrifugation (Sorvall RC 5c Plus, 17,000 rpm 20 minutes, 4° C.). The pellet is resuspended in buffer (50 mM Tris, pH 7.5). Protein concentration (ug/ul) is determined using the Micro-BCA Protein Determination. The binding assay is set up in a 96 well microtiter plate in a total volume of 250 uL. Non-specific binding is determined in the presence of 10 uM clobenpropit. The final radioligand concentration is 1 nM. The test compound is serially diluted using the Beckman Biomek2000 to a final approximate range of 100 uM to 100 pM. Membranes are suspended in buffer, homogenized in 2 bursts of ten seconds using a Vitris mechanical homogenizer set at power setting 5. Ten µg of membranes are added to each well. Following a one hour incubation at 30° C., the reaction is terminated by the addition of ice cold buffer and rapid filtration with a Packard Filtermate Harvester through a GF/B filter pre-soaked with 1% PEI for one hour. The plate is dried for one hour at 37° C. and 60 µL Microscint Scintillant is added to each well. The CPM per well is measured on a Packard Top Count NXT. Ki values are determined in nM. The Ki is calculated from the $IC_{50}$ (i.e. the concentration of competing ligand which displaces 50% of the specific binding of the radioligand). CPM values are expressed as % specific binding and plotted vs compound concentration. A curve is fitted using a four-parameter logistic fit and the $IC_{50}$ value is determined. The Ki is calculated from this using the Cheng-Prusoff equation: $pKi=IC_{50}/1+(L/Kd)$ where L=concentration of free radioligand used in the assay, and Kd is the dissociation constant of the radioligand for the receptor. L is determined for each experiment by counting an aliquot of the diluted radioligand (corresponding to that added to each well) and the Kd has previously been determined under identical conditions for this cell line/radioligand. The data are shown in Table X, below.

TABLE X

| Example Number | H$_3$ Binding Ki (nM) |
|---|---|
| 6B | A |
| 7 | A |
| 8 | B |
| 9 | A |
| 10 | E |
| 11 | E |
| 12 | A |
| 13 | A |
| 14 | A |
| 15 | D |
| 16 | A |
| 17 | A |
| 18 | B |
| 19 | A |
| 20 | A |
| 21 | B |
| 22 | B |
| 28 | A |
| 29 | C |
| 36 | A |
| 37 | A |
| 38 | B |
| 39 | B |
| 40 | E |
| 41 | E |
| 42 | C |
| 43 | B |
| 44 | C |
| 45 | A |
| 46 | A |
| 47 | A |
| 48 | A |
| 51 | A |
| 52 | A |
| 53 | A |
| 54 | B |
| 58 | B |
| 59 | A |
| 60 | D |
| 61 | C |
| 67 | A |
| 71 | B |
| 72 | A |
| 73 | A |
| 74 | A |
| 81 | D |
| 88 | D |
| 94 | D |
| 95 | D |
| 96 | D |
| 97 | A |
| 98 | A |
| 99 | B |
| 100 | B |
| 101 | C |
| 102 | A |
| 104 | E |
| 105 | A |
| 106 | A |
| 107 | E |
| 108 | C |
| 109 | E |
| 110 | E |
| 111 | E |
| 112 | E |
| 113 | E |
| 114 | A |
| 115 | A |
| 116 | B |
| 117 | A |
| 118 | B |

TABLE X-continued

| Example Number | H$_3$ Binding Ki (nM) |
|---|---|
| 119 | B |
| 120 | B |
| 121 | C |
| 122 | B |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 139 | D |
| 140 | A |
| 143 | E |
| 144 | E |
| 145 | E |
| 146 | E |
| 151 | A |

For Table X
A = ≦10 nM
B = 10.1 nM-25.0 nM
C = 25.1 nM-50.0 nM
D = 50.1 nM-100 nM
E = >100 nM Cyclic AMP Assay for Histamine Receptor H$_3$ Antagonism Activity Stable H$_3$ cells are maintained in tissue culture flask in DMEM with high glucose, 10% FBS, 1× pen/strep, 500 ug/ml GY18, until experiment. Culture media is removed and cells are washed twice with PBS w/Ca++ and Mg++ plus 500 μM IBMX. Cells are then detached by tapping on the side of the flask and resuspend in the same buffer. Two thousand cells/well are incubated with 1 μM histamine plus 10 μM forskolin plus various concentrations of compounds in a total volume of 30 μL in 96 well plates for 30 min at 30° C. Final test compound concentrations range from 10-4M to 10-9.5M at full log dilutions. Cyclic AMP levels are measured using HitHunter cAMP kit from Discoverx, cat#900041 according to manufacturer's instruction. Chemiluminescence signals are detected using Top Count (Packard).

Cyclic AMP levels in control cells receiving 10 μM forskolin plus 100 nM histamine are considered 0%, and in cells receiving 10 uM forskolin plus 100 nM histamine plus 1 μM clobenpropit are considered 100%. Data are expressed as % control and analyzed using Prizm soft ware. The Kb values are calculated using the following equation, Kb=EC$_{50}$ or IC$_{50}$/[1+(ligand/Kd)].

Kb values for example compounds described herein were compared with known values for Clobenpropit, Thioperamide and Ciproxifan. Of the four example compounds screened, all exhibited a Kb value of less than 4 nm.

All references cited herein are hereby incorporated by reference in their entirety.

What is claimed is:
1. A compound of formula (Ia)

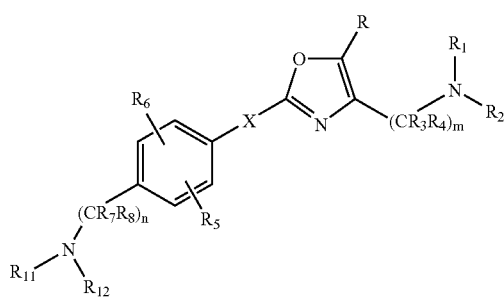

(Ia)

wherein
X is $(CH_2)_o$;
m is 1, 2 or 3;
n is 0, 1, 2 or 3;
R is H, halogen or an optionally substituted $C_1$-$C_6$ alkyl group;
$R_1$ and $R_2$ are each independently H or an optionally substituted $C_1$-$C_6$ alkyl group or $R_1$ and $R_2$ may be taken together with the atom to which they are attached to form an optionally substituted 4- to 7-membered cycloheteroalkyl;
$R_3$, $R_4$, $R_7$ and $R_8$ are each independently H, or a $C_1$-$C_6$ alkyl, $C_3$-$C_{10}$ cycloalkyl, or $C_6$-$C_{10}$ aryl group each optionally substituted;
$R_5$ and $R_6$ are each independently H, halogen, $OR_{10}$ or $C_1$-$C_6$ alkyl, $C_2$-$C_6$ alkenyl or $C_2$-$C_6$ alkynyl;
$R_{10}$ is H or an optionally substituted $C_1$-$C_6$ alkyl group; and
$R_{11}$ and $R_{12}$ are taken together with the atom to which they are attached to form an optionally substituted fused bicyclic 9- to 11-membered ring system optionally containing one to three additional heteroatoms selected from N, O or S; or
a stereoisomer or a pharmaceutically acceptable salt thereof;
wherein the optionally substituted groups are selected from the group consisting of $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, halo, nitro, cyano, hydroxy, $C_6$-$C_{10}$ aryl, a 3-10 membered heterocyclyl ring, a 5-10 membered heteroaryl ring, —$N(R^a)_2$, —$C(O)R^b$, —$OR^c$ and —$S(O)_pR^d$; wherein each $R^a$ is independently H, $C_1$-$C_4$ alkyl, —CHO, —C(O)($C_1$-$C_4$ alkyl), or —C(O)—O—($C_1$-$C_4$ alkyl); each $R^b$ is independently H, —OH, O($C_1$-$C_4$alkyl), $C_1$-$C_4$ alkyl, —$NH_2$, —NH($C_1$-$C_4$ alkyl), or —N($C_1$-$C_4$ alkyl)$_2$; each $R^c$ is independently H, $C_1$-$C_4$ alkyl optionally substituted with halo, —CHO or —C(O)($C_1$-$C_4$ alkyl); each $R^d$ is independently $C_1$-$C_4$ alkyl, or —OH; and p is 0, 1 or 2.

2. The compound of claim 1, wherein m is 1;
or a stereoisomer or pharmaceutically acceptable salt thereof.

3. The compound of claim 1, wherein n is 1;
or a stereoisomer or pharmaceutically acceptable salt thereof.

4. The compound of claim 1, wherein n is 0;
or a stereoisomer or pharmaceutically acceptable salt thereof.

5. The compound of claim 1, wherein $R_3$, $R_4$, $R_7$ and $R_8$ are each independently H or methyl optionally substituted with a group selected from the group consisting of $C_1$-$C_6$ alkyl, $C_3$-$C_6$ cycloalkyl, $C_2$-$C_6$ alkenyl, $C_2$-$C_6$ alkynyl, halo, nitro, cyano, hydroxy, $C_6$-$C_{10}$ aryl, a 3-10 membered heterocyclyl ring, a 5-10 membered heteroaryl ring, —$N(R^a)_2$, —$C(O)R^b$, —$OR^c$ and —$S(O)_pR^d$; wherein each $R^a$ is independently H, $C_1$-$C_4$ alkyl, —CHO, —C(O)($C_1$-$C_4$ alkyl), or or —C(O)—O—($C_1$-$C_4$ alkyl); each $R^b$ is independently H, —OH, O($C_1$-$C_4$alkyl), $C_1$-$C_4$ alkyl, —$NH_2$, —NH($C_1$-$C_4$ alkyl), or —N($C_1$-$C_4$ alkyl)$_2$; each $R^c$ is independently H, $C_1$-$C_4$ alkyl optionally substituted with halo, —CHO or —C(O)($C_1$-$C_4$ alkyl); each $R^d$ is independently $C_1$-$C_4$ alkyl, or —OH; and p is 0, 1 or 2;
or a stereoisomer or pharmaceutically acceptable salt thereof.

6. The compound of claim 1, wherein $R_1$ and $R_2$ are taken together with the atom to which they are attached to form a 5-membered cycloheteroalkyl ring optionally substituted with a group selected from the group consisting of $C_1$-$C_6$ alkyl, $C_3$-$C_6$ cycloalkyl, $C_2$-$C_6$ alkenyl, $C_2$-$C_6$ alkynyl, halo, nitro, cyano, hydroxy, $C_6$-$C_{10}$ aryl, a 3-10 membered heterocyclyl ring, a 5-10 membered heteroaryl ring, —$N(R^a)_2$, —$C(O)R^b$, —$OR^c$ and —$S(O)_pR^d$; wherein each $R^a$ is independently H, $C_1$-$C_4$ alkyl, —CHO, —C(O)($C_1$-$C_4$ alkyl), or or —C(O)—O—($C_1$-$C_4$ alkyl); each $R^b$ is independently H, —OH, O($C_1$-$C_4$alkyl), $C_1$-$C_4$ alkyl, —$NH_2$, —NH($C_1$-$C_4$ alkyl), or —N($C_1$-$C_4$ alkyl)$_2$; each $R^c$ is independently H, $C_1$-$C_4$ alkyl optionally substituted with halo, —CHO or —C(O)($C_1$-$C_4$ alkyl); each $R^d$ is independently $C_1$-$C_4$ alkyl, or —OH; and p is 0, 1 or 2;
or a stereoisomer or pharmaceutically acceptable salt thereof.

7. The compound of claim 1, wherein $R_{11}$ and $R_{12}$ are taken together with the atom to which they are attached to form an indole, indazole or benzimidazole ring each independently optionally substituted with a group selected from the group consisting of $C_1$-$C_6$ alkyl, $C_3$-$C_6$cycloalkyl, $C_2$-$C_6$ alkenyl, $C_2$-$C_6$ alkynyl, halo, nitro, cyano, hydroxy, $C_6$-$C_{10}$ aryl, a 3-10 membered heterocyclyl ring, a 5-10 membered heteroaryl ring, —$N(R^a)_2$, —$C(O)R^b$, —$OR^c$ and —$S(O)_pR^d$; wherein each $R^a$ is independently H, $C_1$-$C_4$ alkyl, —CHO, —C(O)($C_1$-$C_4$ alkyl), or or —C(O)—O—($C_1$-$C_4$ alkyl); each $R^b$ is independently H, —OH, O($C_1$-$C_4$alkyl), $C_1$-$C_4$ alkyl, —$NH_2$, —NH($C_1$-$C_4$ alkyl), or —N($C_1$-$C_4$ alkyl)$_2$; each $R^c$ is independently H, $C_1$-$C_4$ alkyl optionally substituted with halo, —CHO or —C(O)($C_1$-$C_4$ alkyl); each $R^d$ is independently $C_1$-$C_4$ alkyl, or —OH; and p is 0, 1 or 2;
or a stereoisomer or pharmaceutically acceptable salt thereof.

8. The compound of claim 1, wherein $R_1$ and $R_2$ are taken together with the atom to which they are attached to form an optionally substituted 5-membered cycloheteroalkyl ring; and $R_{11}$ and $R_{12}$ are taken together with the atom to which they are attached to form an optionally substituted benzimidazole ring;
or a stereoisomer or pharmaceutically acceptable salt thereof;
wherein the optionally substituted groups are selected from the group consisting of $C_1$-$C_6$ alkyl, $C_3$-$C_6$cycloalkyl, $C_2$-$C_6$ alkenyl, $C_2$-$C_6$ alkynyl, halo, nitro, cyano, hydroxy, $C_6$-$C_{10}$ aryl, a 3-10 membered heterocyclyl ring, a 5-10 membered heteroaryl ring, —$N(R^a)_2$, —$C(O)R^b$, —$OR^c$ and —$S(O)_pR^d$; wherein each $R^a$ is independently H, $C_1$-$C_4$ alkyl, —CHO, —C(O)($C_1$-$C_4$ alkyl), or or —C(O)—O—($C_1$-$C_4$ alkyl); each $R^b$ is independently H, —OH, O($C_1$-$C_4$alkyl), $C_1$-$C_4$ alkyl, —$NH_2$, —NH($C_1$-$C_4$ alkyl), or —N($C_1$-$C_4$ alkyl)$_2$; each $R^c$ is independently H, $C_1$-$C_4$ alkyl optionally substituted with halo, —CHO or —C(O)($C_1$-$C_4$ alkyl); each $R^d$ is independently $C_1$-$C_4$ alkyl, or —OH; and p is 0, 1 or 2.

9. The compound of claim 1, wherein R is H;
or a stereoisomer or pharmaceutically acceptable salt thereof.

10. The compound of claim 1, wherein $NR_{11}R_{12}$ has the following structure:

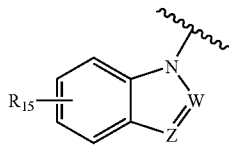

wherein,
W and Z are each independently N or $CR_{16}$; and
$R_{15}$ and $R_{16}$ are each independently H, $C_1$-$C_6$ alkyl, $C_1$-$C_6$ alkoxy, $C_6$-$C_{10}$ aryl or $C_3$-$C_6$ cycloalkyl;
with the proviso that W and Z are not both N;
or a stereoisomer or pharmaceutically acceptable salt thereof.

11. The compound of claim 10, wherein W is $CR_{16}$ and Z is N;
or a stereoisomer or pharmaceutically acceptable salt thereof.

12. The compound of claim 11, wherein $R_{16}$ is H and $R_{15}$ is H;
or a stereoisomer or pharmaceutically acceptable salt thereof.

13. The compound of claim 10, wherein W is N and Z is $CR_{16}$;
or a stereoisomer or pharmaceutically acceptable salt thereof.

14. The compound of claim 10, wherein both W and Z are independently $CR_{16}$;
or a stereoisomer or pharmaceutically acceptable salt thereof.

15. The compound of claim 10, wherein $R_{15}$ is selected from the group consisting of H, 5-$OCH_3$, 6-$OCH_3$, 5-$CH_3$ and 6-$CH_3$.

16. The compound of claim 10, wherein $R_{16}$ is phenyl, H or $CH_3$.

17. The compound of claim 1, wherein $NR_1R_2$ has the following structure:

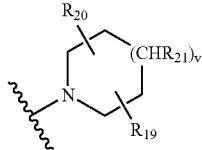

v is 0, 1 or 2;
$R_{19}$, $R_{20}$ and $R_{21}$ are each independently H, halo, nitro, cyano, hydroxy, $S(O)_qR^d$, —$N(R^a)_2$, or $C_1$-$C_6$ alkyl, $C_1$-$C_4$ acyl, $C_1$-$C_4$ alkoxy, $C_6$-$C_{10}$ aryl, 5-10 membered heteroaryl, 3-10 membered heterocyclyl, or $C_3$-$C_6$ cycloalkyl, each substituted with 0-4 substituents independently selected from the group consisting of $C_1$-$C_4$ alkyl, $C_3$-$C_6$ cycloalkyl, $C_2$-$C_6$ alkenyl, $C_2$-$C_6$ alkynyl, halo, nitro, cyano, hydroxy, phenyl, 3-10 membered heterocyclyl, —$N(R^a)_2$, —$C(O)R^b$, —$OR^c$ and —$S(O)_qR^d$;
each $R^a$ is independently H, $C_1$-$C_4$ alkyl optionally substituted with halo, —CHO, —C(O)($C_1$-$C_4$ alkyl) or —C(O)—O—($C_1$-$C_4$ alkyl);
each $R^b$ is independently H, —OH, —O($C_1$-$C_4$ alkyl), $C_1$-$C_4$ alkyl optionally substituted with halo, —$NH_2$, —NH($C_1$-$C_4$ alkyl) or —N($C_1$-$C_4$ alkyl)$_2$;
each $R^c$ is independently H, $C_1$-$C_4$ alkyl optionally substituted with halo, —CHO or —C(O)($C_1$-$C_4$ alkyl);
each $R^d$ is independently $C_1$-$C_4$ alkyl optionally substituted with halo, or —OH; and
each q is independently 0, 1 or 2;
or a stereoisomer or pharmaceutically acceptable salt thereof.

18. The compound of claim 17, wherein v is 0;
or a stereoisomer or pharmaceutically acceptable salt thereof.

19. The compound of claim 17, wherein v is 1 and $R_{21}$ is H;
or a stereoisomer or pharmaceutically acceptable salt thereof.

20. The compound of claim 17, wherein v is 2 and $R_{21}$ is H;
or a stereoisomer or pharmaceutically acceptable salt thereof.

21. The compound of claim 17, wherein $R_{19}$ and $R_{20}$ are independently H or methyl;
or a stereoisomer or pharmaceutically acceptable salt thereof.

22. The compound of claim 1, wherein —$NR_1R_2$ is selected from the group consisting of piperidinyl, dimethylamino, methylethylamino, morpholin-4-yl, 4-methylpiperazinyl, diethylamino, 2-methylpyrrolidinyl, azepanyl, 2-methylpiperidinyl, 3-methylpiperidinyl, 4-methylpiperidinyl, (R)-2-methylpyrrolidinyl, (S)-2-methylpyrrolidinyl, (R)-3-fluoropyrrolidinyl, (S)-3-fluoropyrrolidinyl, and pyrrolidinyl;
or a stereoisomer or pharmaceutically acceptable salt thereof.

23. The compound of claim 1, selected from the group consisting of:
1-{4-[4-(pyrrolidin-1-ylmethyl)-1,3-oxazol-2-yl]benzyl}-1H-benzimidazole;
1-{4-[4-(piperidin-1-ylmethyl)-1,3-oxazol-2-yl]benzyl}-1H-benzimidazole;
1-{2-[4-(1H-benzimidazol-1-ylmethyl)phenyl]-1,3-oxazol-4-yl}-N,N-dimethylmethanamine;
N-({2-[4-(1H-benzimidazol-1-ylmethyl)phenyl]-1,3-oxazol-4-yl}methyl)-N-methylethanamine;
1-{4-[4-(morpholin-4-ylmethyl)-1,3-oxazol-2-yl]benzyl}-1H-benzimidazole;
1-(4-{4-[(4-methylpiperazin-1-yl)methyl]-1,3-oxazol-2-yl}benzyl)-1H-benzimidazole;
N-({2-[4-(1H-benzimidazol-1-ylmethyl)phenyl]-1,3-oxazol-4-yl}methyl)-N-ethylethanamine;
1-(4-{4-[(2-methylpyrrolidin-1-yl)methyl]-1,3-oxazol-2-yl}benzyl)-1H-benzimidazole;
1-{4-[4-(azepan-1-ylmethyl)-1,3-oxazol-2-yl]benzyl}-1H-benzimidazole;
1-(4-{4-[(2-methylpiperidin-1-yl)methyl]-1,3-oxazol-2-yl}benzyl)-1H-benzimidazole;
1-(4-{4-[(3-methylpiperidin-1-yl)methyl]-1,3-oxazol-2-yl}benzyl)-1H-benzimidazole;
1-(4-{4-[(4-methylpiperidin-1-yl)methyl]-1,3-oxazol-2-yl}benzyl)-1H-benzimidazole;
1-[4-(4-{[(2R)-2-methylpyrrolidin-1-yl]methyl}-1,3-oxazol-2-yl)benzyl]-1H-benzimidazole;
1-[4-(4-{[(2S)-2-methylpyrrolidin-1-yl]methyl}-1,3-oxazol-2-yl)benzyl]-1H-benzimidazole;
1-[4-(4-{[(3R)-3-fluoropyrrolidin-1-yl]methyl}-1,3-oxazol-2-yl)benzyl]-1H-benzimidazole;
1-[4-(4-{[(3S)-3-fluoropyrrolidin-1-yl]methyl}-1,3-oxazol-2-yl)benzyl]-1H-benzimidazole;
1-{4-[5-methyl-4-(pyrrolidin-1-ylmethyl)-1,3-oxazol-2-yl]benzyl}-1H-benzimidazole;
1-{4-[5-bromo-4-(pyrrolidin-1-ylmethyl)-1,3-oxazol-2-yl]benzyl}-1H-benzimidazole;
1-{4-[4-(pyrrolidin-1-ylmethyl)-1,3-oxazol-2-yl]phenyl}-1H-benzimidazole;

1-{4-[4-(piperidin-1-ylmethyl)-1,3-oxazol-2-yl]benzyl}-1H-benzimidazole;
1-{2-[4-(1H-benzimidazol-1-yl)phenyl]-1,3-oxazol-4-yl}-N,N-dimethylmethanamine;
N-({2-[4-(1H-benzimidazol-1-yl)phenyl]-1,3-oxazol-4-yl}methyl)-N-methylethanamine;
1-{4-[4-(morpholin-4-ylmethyl)-1,3-oxazol-2-yl]phenyl}-1H-benzimidazole;
1-(4-{4-[(4-methylpiperidin-1-yl)methyl]-1,3-oxazol-2-yl}phenyl)-1H-benzimidazole;
N-({2-[4-(1H-benzimidazol-1-yl)phenyl]-1,3-oxazol-4-yl}methyl)-N-ethylethanamine;
1-(4-{4-[(2-methylpyrrolidin-1-yl)methyl]-1,3-oxazol-2-yl}phenyl)-1H-benzimidazole;
1-{4-[4-(azepan-1-ylmethyl)-1,3-oxazol-2-yl]phenyl}-1H-benzimidazole;
1-(4-{4-[(2-methylpiperidin-1-yl)methyl]-1,3-oxazol-2-yl}phenyl)-1H-benzimidazole;
1-(4-{4-[(3-methylpiperidin-1-yl)methyl]-1,3-oxazol-2-yl}phenyl)-1H-benzimidazole;
1-(4-{4-[(4-methylpiperazin-1-yl)methyl]-1,3-oxazol-2-yl}phenyl)-1H-benzimidazole;
1-{4-[4-(pyrrolidin-1-ylmethyl)-1,3-oxazol-2-yl]benzyl}-1H-indole;
6-fluoro-1-[4-(4-{[(2S)-2-methylpyrrolidin-1-yl]methyl}-1,3-oxazol-2-yl)benzyl]-1H-indazole;
1-{4-[4-(pyrrolidin-1-ylmethyl)-1,3-oxazol-2-yl]benzyl}-1H-indazole;
1-[4-(4-{[(2R)-2-methylpyrrolidin-1-yl]methyl}-1,3-oxazol-2-yl)benzyl]-1H-indazole;
5-fluoro-1-[4-(4-{[(2R)-2-methylpyrrolidin-1-yl]methyl}-1,3-oxazol-2-yl)benzyl]-1H-indazole;
6-fluoro-1-[4-(4-{[(2R)-2-methylpyrrolidin-1-yl]methyl}-1,3-oxazol-2-yl)benzyl]-1H-indazole;
5-fluoro-1-{4-[4-(pyrrolidin-1-ylmethyl)-1,3-oxazol-2-yl]benzyl}-1H-indazole;
6-fluoro-1-{4-[4-(pyrrolidin-1-ylmethyl)-1,3-oxazol-2-yl]benzyl}-1H-indazole;
1-[4-(4-{[(2S)-2-methylpyrrolidin-1-yl]methyl}-1,3-oxazol-2-yl)benzyl]-1H-indazole;
1-(1-{4-[4-(pyrrolidin-1-ylmethyl)-1,3-oxazol-2-yl]benzyl}-1H-indazol-5-yl)methanamine;
5-fluoro-1-[4-(4-{[(2S)-2-methylpyrrolidin-1-yl]methyl}-1,3-oxazol-2-yl)benzyl]-1H-indazole;
2-phenyl-1-{4-[4-(pyrrolidin-1-ylmethyl)-1,3-oxazol-2-yl]benzyl}-1H-benzimidazole;
1-[4-(4-{[(2R)-2-methylpyrrolidin-1-yl]methyl}-1,3-oxazol-2-yl)benzyl]-2-(trifluoromethyl)-1H-benzimidazole;
1-[4-(4-{[(2S)-2-methylpyrrolidin-1-yl]methyl}-1,3-oxazol-2-yl)benzyl]-2-(trifluoromethyl)-1H-benzimidazole;
1-[4-(4-{[(2R)-2-methylpyrrolidin-1-yl]methyl}-1,3-oxazol-2-yl)benzyl]-2-phenyl-1H-benzimidazole;
1-[4-(4-{[(2S)-2-methylpyrrolidin-1-yl]methyl}-1,3-oxazol-2-yl)benzyl]-2-phenyl-1H-benzimidazole;
1-{4-[4-(azepan-1-ylmethyl)-1,3-oxazol-2-yl]benzyl}-2-(trifluoromethyl)-1H-benzimidazole;
1-{4-[4-(azepan-1-ylmethyl)-1,3-oxazol-2-yl]benzyl}-2-phenyl-1H-benzimidazole;
1-{4-[4-(azepan-1-ylmethyl)-1,3-oxazol-2-yl]benzyl}-5-methoxy-1H-benzimidazole;
1-{4-[4-(azepan-1-ylmethyl)-1,3-oxazol-2-yl]benzyl}-6-methoxy-1H-benzimidazole;
1-{4-[4-(azepan-1-ylmethyl)-1,3-oxazol-2-yl]benzyl}-5-methyl-1H-benzimidazole;
1-{4-[4-(azepan-1-ylmethyl)-1,3-oxazol-2-yl]benzyl}-6-methyl-1H-benzimidazole;
2-phenyl-1-{4-[4-(piperidin-1-ylmethyl)-1,3-oxazol-2-yl]benzyl}-1H-benzimidazole;
1-{4-[4-(piperidin-1-ylmethyl)-1,3-oxazol-2-yl]benzyl}-2-(trifluoromethyl)-1H-benzimidazole;
1-{4-[4-(azepan-1-ylmethyl)-1,3-oxazol-2-yl]benzyl}-2,5-dimethyl-1H-benzimidazole;
1-{4-[4-(azepan-1-ylmethyl)-1,3-oxazol-2-yl]benzyl}-2,6-dimethyl-1H-benzimidazole;
2,5-dimethyl-1-[4-(4-{[(2S)-2-methylpyrrolidin-1-yl]methyl}-1,3-oxazol-2-yl)benzyl]-1H-benzimidazole;
2,6-dimethyl-1-[4-(4-{[(2S)-2-methylpyrrolidin-1-yl]methyl}-1,3-oxazol-2-yl)benzyl]-1H-benzimidazole;
2,5-dimethyl-1-{4-[4-(pyrrolidin-1-ylmethyl)-1,3-oxazol-2-yl]benzyl}-1H-benzimidazole;
2,6-dimethyl-1-{4-[4-(pyrrolidin-1-ylmethyl)-1,3-oxazol-2-yl]benzyl}-1H-benzimidazole;
5-methoxy-1-{4-[4-(pyrrolidin-1-ylmethyl)-1,3-oxazol-2-yl]benzyl}-1H-benzimidazole;
6-methoxy-1-{4-[4-(pyrrolidin-1-ylmethyl)-1,3-oxazol-2-yl]benzyl}-1H-benzimidazole;
5-methyl-1-{4-[4-(pyrrolidin-1-ylmethyl)-1,3-oxazol-2-yl]benzyl}-1H-benzimidazole;
6-methyl-1-{4-[4-(pyrrolidin-1-ylmethyl)-1,3-oxazol-2-yl]benzyl}-1H-benzimidazole;
5-methoxy-1-[4-(4-{[(2S)-2-methylpyrrolidin-1-yl]methyl}-1,3-oxazol-2-yl)benzyl]-1H-benzimidazole;
6-methoxy-1-[4-(4-{[(2S)-2-methylpyrrolidin-1-yl]methyl}-1,3-oxazol-2-yl)benzyl]-1H-benzimidazole;
5-methyl-1-[4-(4-{[(2S)-2-methylpyrrolidin-1-yl]methyl}-1,3-oxazol-2-yl)benzyl]-1H-benzimidazole;
6-methyl-1-[4-(4-{[(2S)-2-methylpyrrolidin-1-yl]methyl}-1,3-oxazol-2-yl)benzyl]-1H-benzimidazole;
5-methoxy-1-[4-(4-{[(2R)-2-methylpyrrolidin-1-yl]methyl}-1,3-oxazol-2-yl)benzyl]-1H-benzimidazole; and
6-methoxy-1-[4-(4-{[(2R)-2-methylpyrrolidin-1-yl]methyl}-1,3-oxazol-2-yl)benzyl]-1H-benzimidazole; or
a pharmaceutically acceptable salt thereof.

24. A pharmaceutical composition which comprises a pharmaceutically acceptable carrier and a compound of formula (Ia) according to claim 1; or a stereoisomer or a pharmaceutically acceptable salt thereof.

25. The compound of claim 1 having the structure:

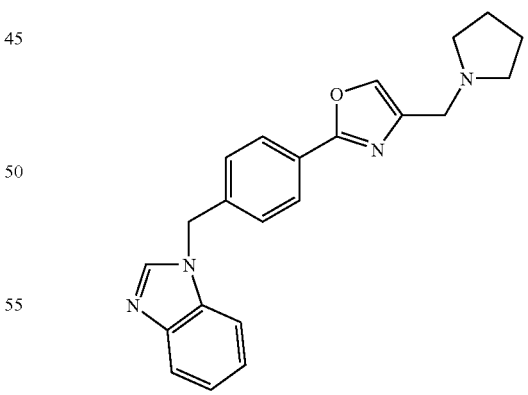

or a pharmaceutically acceptable salt thereof.

26. The compound of claim 25, wherein the pharmaceutically acceptable salt is HCl.

* * * * *